US012673934B2

(12) United States Patent
Groarke et al.

(10) Patent No.: US 12,673,934 B2
(45) Date of Patent: Jul. 7, 2026

(54) COMPOUND, MATERIAL FOR AN ORGANIC ELECTROLUMINESCENCE DEVICE AND AN ORGANIC ELECTROLUMINESCENCE DEVICE COMPRISING THE COMPOUND

(71) Applicant: IDEMITSU KOSAN CO., LTD., Tokyo (JP)

(72) Inventors: Michelle Groarke, Binningen (CH); Hiroaki Toyoshima, Chiyoda-ku (JP); Masatoshi Saito, Sodegaura (JP); Natalia Chebotareva, Hagenthal le bas (FR)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1014 days.

(21) Appl. No.: 17/815,835

(22) Filed: Jul. 28, 2022

(65) Prior Publication Data

US 2023/0120308 A1 Apr. 20, 2023

(30) Foreign Application Priority Data

Jul. 29, 2021 (EP) ..................................... 21188578

(51) Int. Cl.
*C07D 401/14* (2006.01)
*C07D 403/10* (2006.01)
(Continued)

(52) U.S. Cl.
CPC ......... *C07D 401/14* (2013.01); *C07D 403/10* (2013.01); *H10K 50/16* (2023.02);
(Continued)

(58) Field of Classification Search
CPC ................ C07D 401/14; C07D 403/10; H10K 885/654; H10K 885/6572; H10K 50/16;
(Continued)

(56) References Cited

FOREIGN PATENT DOCUMENTS

KR 10-2017-0058618 A 5/2017
KR 10-2017-0058619 A 5/2017
(Continued)

OTHER PUBLICATIONS

Espacenet translation of KR20170058619A_Description_Sep. 10, 2025_2023 (Year: 2025).*
(Continued)

*Primary Examiner* — Michael M Dollinger
(74) *Attorney, Agent, or Firm* — Oblon, McClelland, Maier & Neustadt, L.L.P.

(57) ABSTRACT

Specific compounds represented by formula (I), a material for an organic electroluminescence device comprising said specific compound, an organic electroluminescence device comprising said specific compound, an electronic equipment comprising said organic electroluminescence device and the use of said compounds in an organic electroluminescence device.

(I)

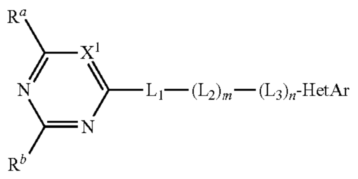

20 Claims, 1 Drawing Sheet

(51) Int. Cl.
*H10K 50/16* (2023.01)
*H10K 85/60* (2023.01)

(52) U.S. Cl.
CPC ......... *H10K 85/615* (2023.02); *H10K 85/654* (2023.02); *H10K 85/6572* (2023.02)

(58) Field of Classification Search
CPC . H10K 85/615; H10K 85/654; H10K 85/6572
See application file for complete search history.

(56) References Cited

FOREIGN PATENT DOCUMENTS

| | | | | | |
|---|---|---|---|---|---|
| KR | 20170058619 | A | * | 5/2017 | ........... C07D 239/24 |
| KR | 10-2017-0103574 | A | | 9/2017 | |
| WO | WO 2010/126270 | A1 | | 11/2010 | |
| WO | WO-2017105063 | A1 | * | 6/2017 | ........... H10K 85/111 |
| WO | WO 2017/156698 | A1 | | 9/2017 | |
| WO | WO 2020/199996 | A1 | | 10/2020 | |
| WO | WO-2021049840 | A1 | * | 3/2021 | ......... H10K 85/6572 |

OTHER PUBLICATIONS

Espacenet translation of WO2021049840A1_Description_Sep. 10, 2025_2002 (Year: 2025).*
Jia et al (Dalton Trans., 2006, 1721â1728). (Year: 2006).*
Partial European Search Report issued Jan. 18, 2022 in European Patent Application No. 21188578.5, 12 pages.
Extended European Search Report issued Apr. 21, 2022 in European Patent Application No. 21188578.5, 11 pages.

* cited by examiner

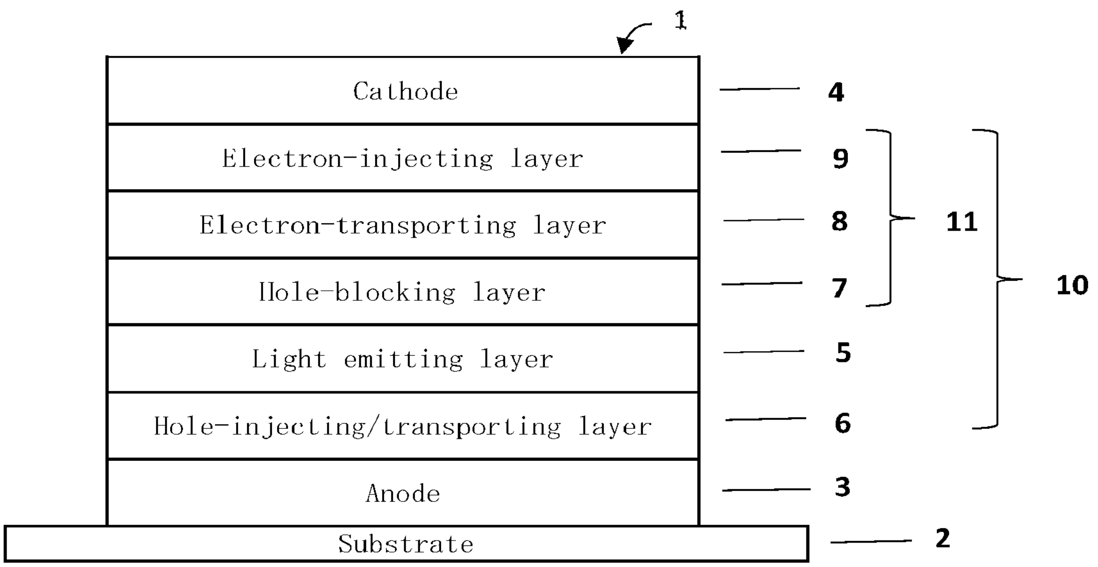
1
Cathode
4
Electron-injecting layer
9
Electron-transporting layer
8
11
Hole-blocking layer
7
10
Light emitting layer
5
Hole-injecting/transporting layer
6
Anode
3
Substrate
2

COMPOUND, MATERIAL FOR AN ORGANIC ELECTROLUMINESCENCE DEVICE AND AN ORGANIC ELECTROLUMINESCENCE DEVICE COMPRISING THE COMPOUND

CROSS-REFERENCE TO RELATED APPLICATION

This application is based upon and claims the benefit of priority from the prior European Patent Application No. 21188578.5, filed on Jul. 29, 2021; the entire contents of which are incorporated herein by reference.

BACKGROUND OF THE INVENTION

Field of the Invention

The present invention relates to specific compounds, a material for an organic electroluminescence device comprising said specific compound, an organic electroluminescence device comprising said specific compound, an electronic equipment comprising said organic electroluminescence device and the use of said compounds in an organic electroluminescence device.

Description of the Background

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

An organic EL device comprises an emitting layer between the anode and the cathode. Further, there may be a case where it has a stacked layer structure comprising an organic layer such as a hole-injecting layer, a hole-transporting layer, an electron-blocking layer, an electron-injecting layer, an electron-transporting layer, a hole-blocking layer etc.

WO2020/199996 A1 relates to a substituted 1,3,5-triazine compound of formula I

I

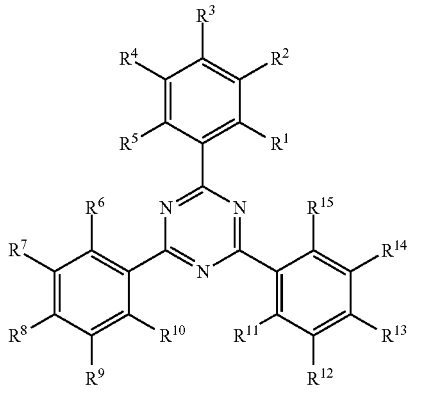

wherein one or two of $R^1$, $R^2$, $R^3$, $R^4$, and $R^5$ are independently R, and R represents

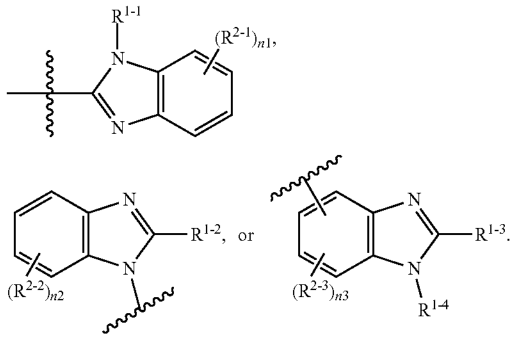

The 1,3,5-triazine compound can be used as an electron transport material or as an electron acceptor material. An electroluminescent device comprising said compound has advantages such as high efficiency and long service life.

Examples mentioned in WO2020/199996 A1 are:

9

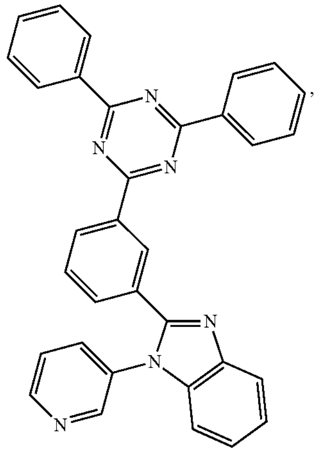

10

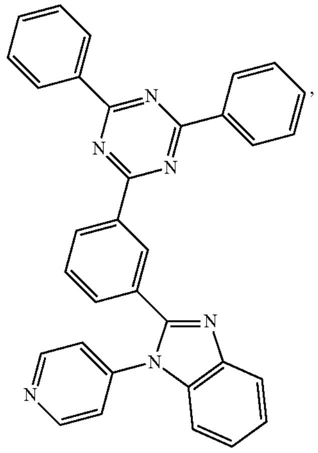

-continued

11

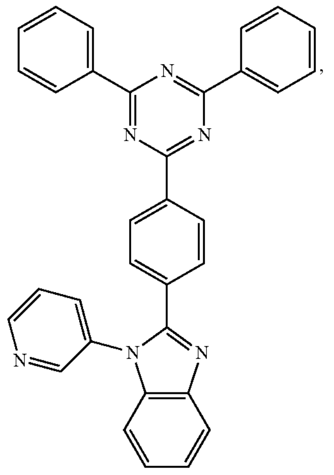

12

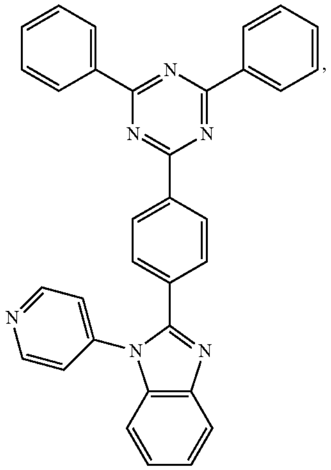

13

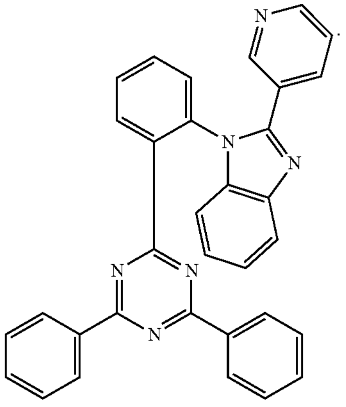

WO 2010/126270 A1 relates to organic electroluminescent compounds and organic electroluminescent devices employing said compounds. The organic electroluminescent compounds of the invention are substituted triazine compounds defined by chemical formula (1). The compounds, when used in an electron transport layer of an organic electroluminescent device, reduce power consumption and operation voltage of said device.

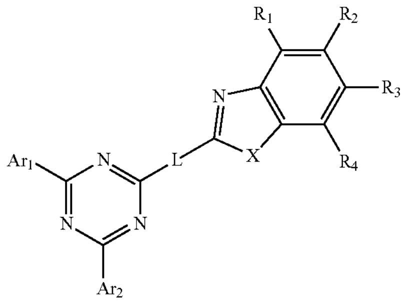

An example for a compound of formula (1) is shown in the following:

70

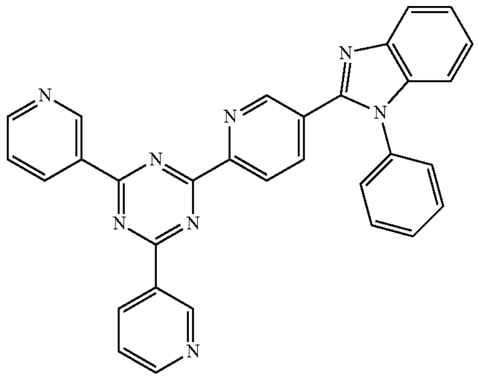

WO 2017/156698 A1 relates to an electron buffer material of formula (1), an organic EL device comprising an electron buffer material, and a first electrode, a second electrode opposing the first electrode, a light-emitting layer disposed between the two electrodes, and an electron transport zone and an electron buffer layer disposed between the light-emitting layer and the second electrode. The organic EL device comprising the electron buffering material of the present disclosure has a low driving voltage, high luminous efficiency and excellent lifespan.

(1)

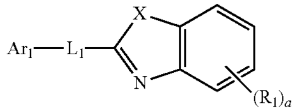

wherein $Ar_1$ represents a substituted or unsubstituted (C6 to C30) aryl group, or a substituted or unsubstituted 5- to 30-membered heteroaryl group.

In one embodiment, the compound of formula (1) is represented by formula (4)

(4)

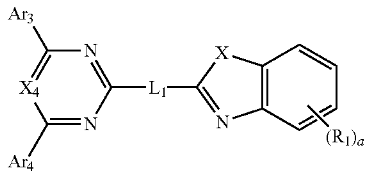

Specific examples of the compound mentioned above are shown in the following:

B-105

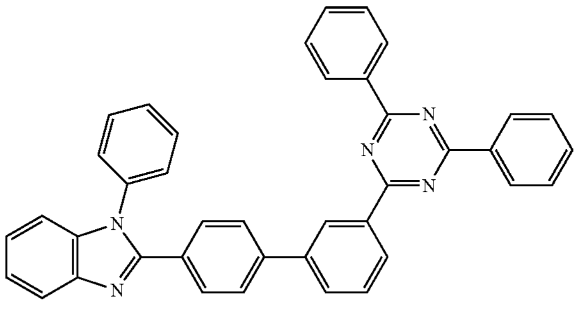

B-106

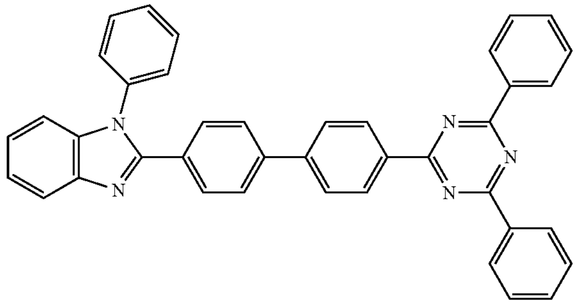

KR 1020170058618A relates to a pyrimidine derivative bonded with a pyridyl group represented by formula (1).

(1)

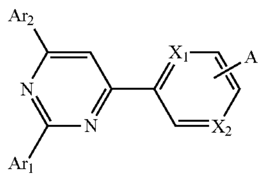

wherein $Ar_1$ and $Ar_2$ are each independently an aryl having 6-30 carbon atoms, or a heteroaryl having 5-30 carbon atoms; $X_1$ and $X_2$ are each independently CH or N, while at least one of $X_1$ and $X_2$ is N; and A has a structure represented by formula (2).

(2)

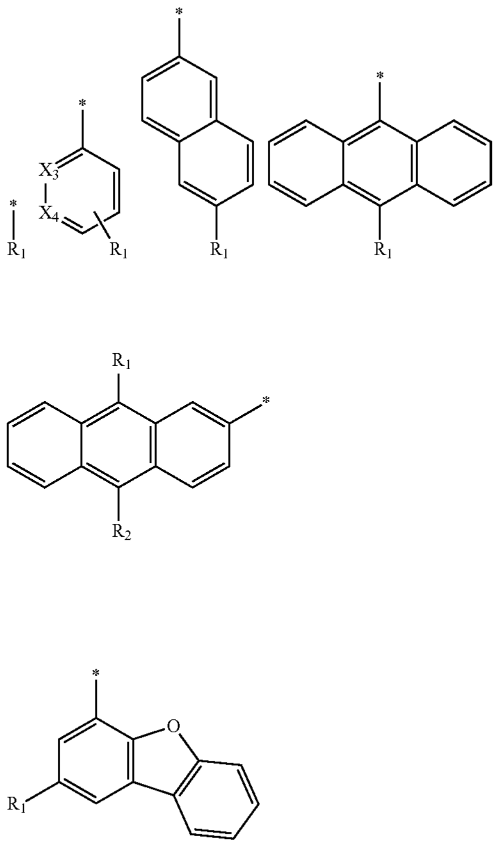

An exemplified compound is as follows:

4-84

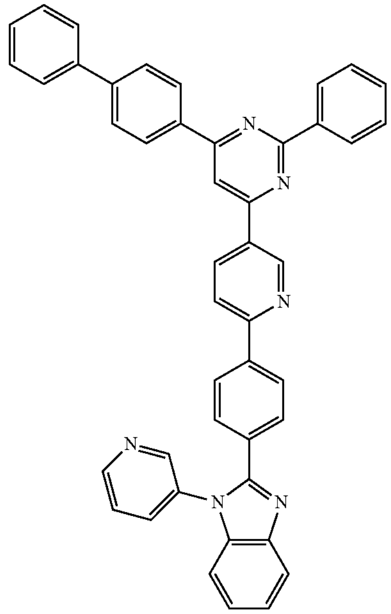

KR 1020170103574A relates to a pyrimidine derivative coupled with aryl- or heteroaryl-substituted fluorene represented by formula (1).

(1)

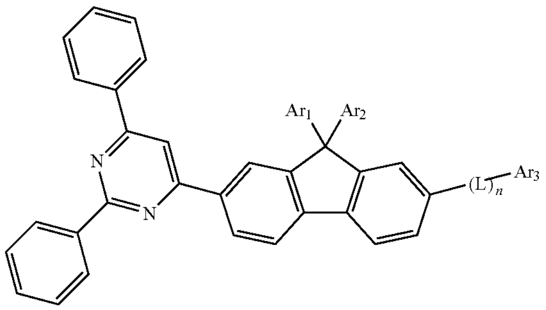

In the formula (1), $Ar_1$ and $Ar_2$ are respectively and independently hydrogen, methyl or phenyl; L is $C_6$-$C_{24}$ aryl or $C_3$-$C_{24}$ heteroaryl; n is an integer of 0 or 1; and $Ar_3$ is $C_6$-$C_{30}$ aryl or $C_3$-$C_{30}$ heteroaryl.

Exemplified compounds are shown in the following:

4-35

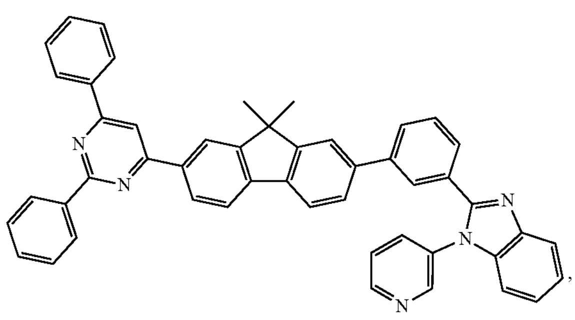

, 4-62

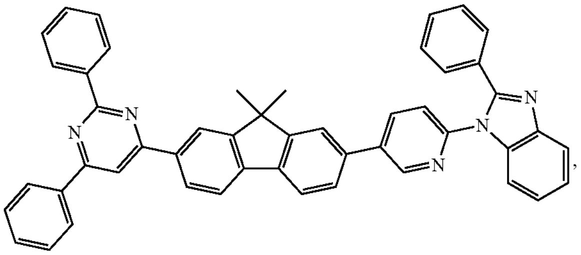

, 4-75

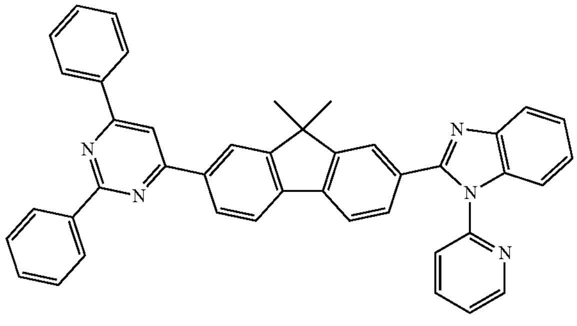

KR 1020170058619A relates to a pyrimidine derivative bonded with a phenyl group represented by formula (1).

(1)

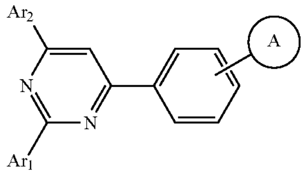

In the chemical formula 1, $Ar_1$ and $Ar_2$ are each independently an aryl having 6-30 carbon atoms, or a heteroaryl having 5-30 carbon atoms; and A has a structure represented by chemical formula 2.

(2)

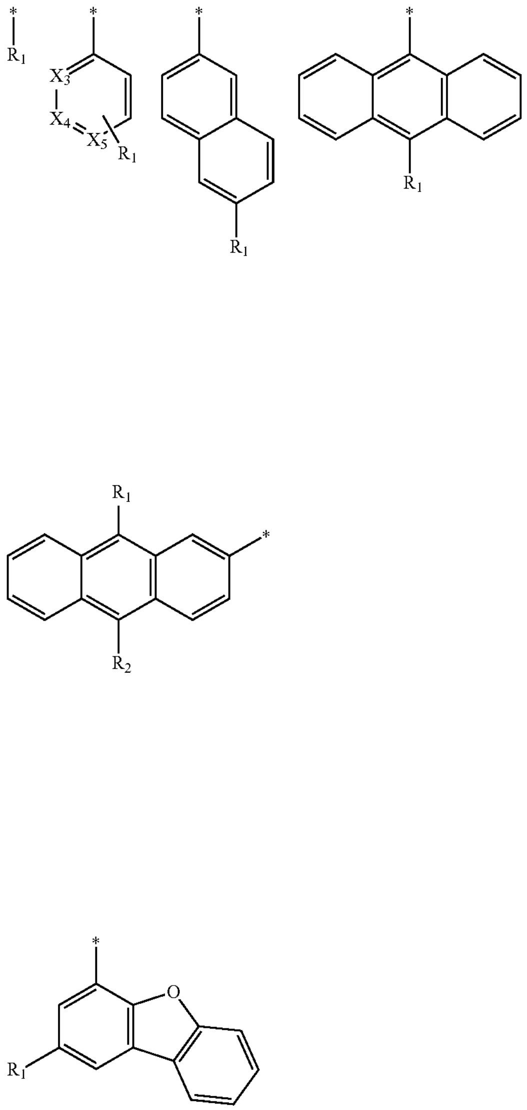

Exemplified compounds are shown in the following:

4-38

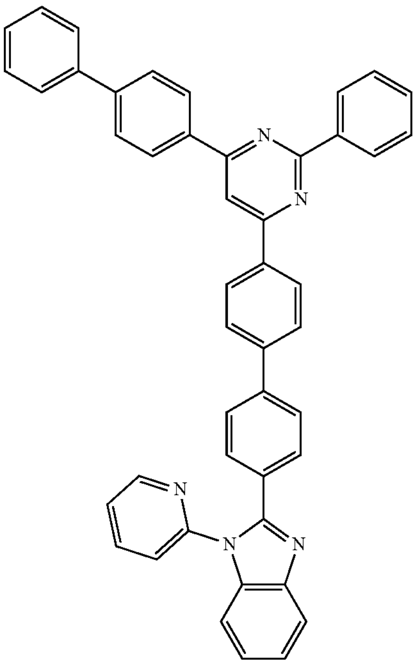

4-39

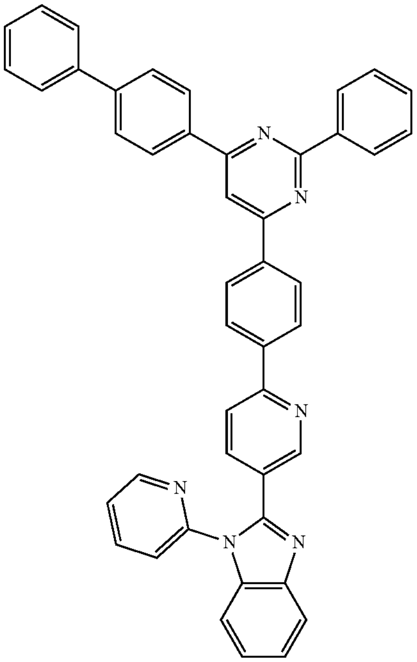

-continued 4-40

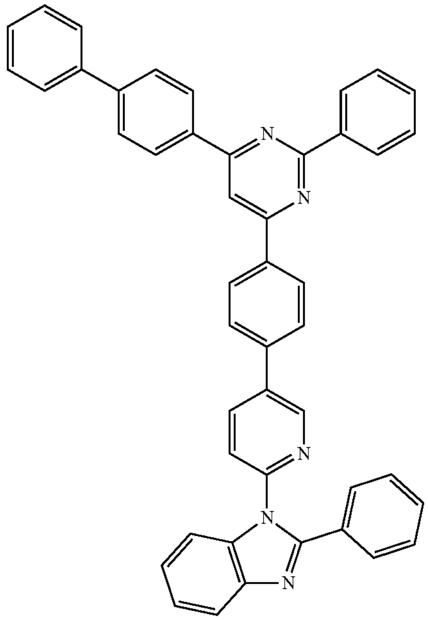

4-41

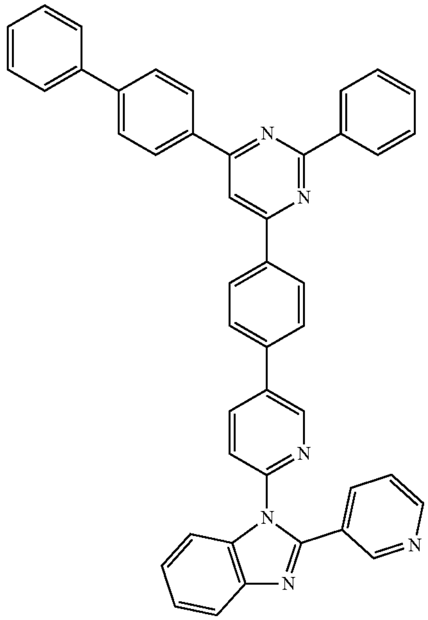

The specific structure and substitution pattern of the compounds in organic electronic devices have a significant impact on the performance of the organic electronic devices.

Therefore, notwithstanding the developments described above, there remains a need for organic electroluminescence devices comprising new materials, especially charge-transporting materials, e.g. electron-transporting materials, charge-blocking materials, e.g. hole-blocking materials and/or dopant materials, more especially electron-transporting materials to provide improved performance of electroluminescence devices.

Accordingly, it is an object of the present invention, with respect to the aforementioned related art, to provide further materials suitable for use in organic electroluminescence devices and further applications in organic electronics. More particularly, it should be possible to provide charge-transporting materials, e.g. electron-transporting materials, and/or charge-blocking materials, e.g. hole-blocking materials, and/or dopant materials for use in organic electroluminescence devices. The materials should be suitable especially for organic electroluminescence devices which comprise at least one emitter, which is a phosphorescence emitter and/or a fluorescence emitter.

Furthermore, the materials should be suitable for providing organic electroluminescence devices which ensure good overall performance of the organic electroluminescence devices, especially a long lifetime, high efficiency and/or a low driving voltage.

BRIEF SUMMARY OF THE INVENTION

Said object is solved by a compound represented by formula (I):

(I)

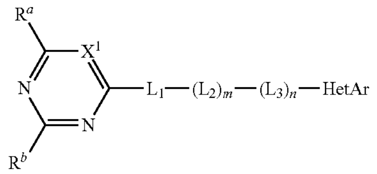

wherein $L_1$ represents a divalent aromatic hydrocarbon group of the following formula

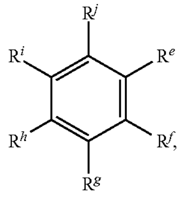

wherein $R^e$, $R^f$, $R^g$, $R^h$, $R^i$ and $R^j$ each independently represents hydrogen, an unsubstituted or substituted aromatic hydrocarbon group containing 6 to 30 ring atoms or, an unsubstituted or substituted alkyl group having 1 to 25 carbon atoms; preferably, $R^e$, $R^f$, $R^g$, $R^h$, $R^i$ and $R^j$ each independently represents hydrogen, unsubstituted or substituted phenyl, or an unsubstituted or substituted alkyl group having 1 to 4 carbon atoms; more preferably hydrogen, unsubstituted phenyl, or an unsubstituted alkyl group having 1 to 4 carbon atoms, more preferably hydrogen; or at least two adjacent residues $R^e$, $R^f$, $R^g$, $R^h$, $R^i$ and $R^j$ form together a 6-membered aromatic ring, which may in turn be fused by at least one further 6-membered aromatic or heteroaromatic ring; or an unsubstituted divalent heteroaromatic group containing 3 to 30 ring atoms, which may in turn be fused by at least one further 6-membered aromatic or heteroaromatic ring;

$L_2$ represents an unsubstituted or substituted divalent aromatic hydrocarbon group containing 6 to 30 ring atoms or an unsubstituted or substituted divalent heteroaromatic group containing 3 to 30 ring atoms;

$L_3$ represents a group of the following formula

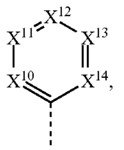

wherein $X^{10}$ represents N or $CR^{10}$;

$X^{11}$ represents N or $CR^{11}$;

$X^{12}$ represents N or $CR^{12}$;

$X^{13}$ represents N or $CR^{13}$;

$X^{14}$ represents N or $CR^{14}$;

wherein at least one of $X^{10}$, $X^{11}$, $X^{12}$, $X^{13}$ and $X^{14}$ is N, preferably exactly one of $X^{10}$, $X^{11}$, $X^{12}$, $X^{13}$ and $X^{14}$ is N; and one of $X^{10}$, $X^{11}$, $X^{12}$, $X^{13}$ and $X^{14}$ is

C----, wherein ---- is a bonding site;

$R^a$ and $R^b$ each independently represents an unsubstituted or substituted aromatic hydrocarbon group containing 6 to 30 ring atoms or an unsubstituted or substituted heteroaromatic group containing 3 to 30 ring atoms;

m represents 0, 1, 2 or 3, preferably 0, 1 or 2, more preferably 1 or 2; wherein the groups $L_2$ may be the same or different in the case that m is 2 or 3;

n represents 0 or 1;

wherein the sum of m and n is at least 1 and—in the case that $X^1$ is $CR^1$—the sum of m and n is at least 2;

$X^1$ is N or $CR^1$, preferably N;

HetAr is represented by one of formula (II) or (III)

(II)

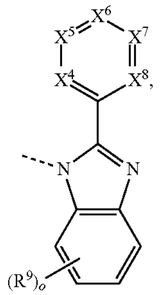

(III)

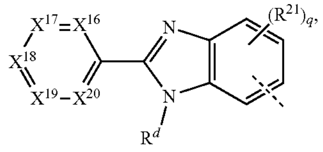

or—in the case that n is 1—HetAr is represented by one of formula (II), (III) or (IV)

(IV)

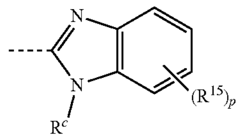

$X^4$ represents N or $CR^4$;
$X^5$ represents N or $CR^5$;
$X^6$ represents N or $CR^6$;
$X^7$ represents N or $CR^7$;
$X^8$ represents N or $CR^8$;
wherein at least one of $X^4$, $X^5$, $X^6$, $X^7$ and $X^8$ is N, preferably exactly one of $X^4$, $X^5$, $X^6$, $X^7$ and $X^8$ is N;
$X^{16}$ represents N or $CR^{16}$;
$X^{17}$ represents N or $CR^{17}$;
$X^{18}$ represents N or $CR^{18}$;
$X^{19}$ represents N or $CR^{19}$;
$X^{20}$ represents N or $CR^{20}$;
wherein at least one of $X^{16}$, $X^{17}$, $X^{18}$, $X^{19}$ and $X^{20}$ is N, preferably exactly one of $X^{16}$, $X^{17}$, $X^{18}$, $X^{19}$ and $X^{20}$ is N;
o and p each independently represents 0, 1, 2, 3 or 4, preferably 0, 1 or 2, more preferably 0;
q represents 0, 1, 2 or 3, preferably 0, 1 or 2, more preferably 0; and
$R^1$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ each independently represents hydrogen, an unsubstituted or substituted aromatic hydrocarbon group containing 6 to 30 ring atoms or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms or CN, or
two adjacent groups $R^9$, two adjacent groups $R^{15}$ or two adjacent groups $R^{21}$ and/or two adjacent groups selected from $R^4$, $R^5$, $R^6$, $R^7$, $R^8$, $R^{10}$, $R^{11}$, $R^{12}$, $R^{13}$, $R^{14}$, $R^{16}$, $R^{17}$, $R^{18}$, $R^{19}$, $R^{20}$ can form together a substituted or unsubstituted carbocyclic or heterocyclic ring;
$R^c$ and $R^d$ each independently represents an unsubstituted or substituted aromatic hydrocarbon group containing 6 to 30 ring atoms or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms;
the dotted line is a bonding site.

BRIEF DESCRIPTION OF THE DRAWINGS

The FIGURE shows a schematic configuration of one example of the organic EL device of the invention.

DETAILED DESCRIPTION OF THE INVENTION

The specific compounds of the present invention according to formula (I) may be used as a material, especially host, charge-transporting or charge-blocking material, preferably as a electron transporting material, that is highly suitable in organic electroluminescence devices. Moreover, thermally stable compounds are provided, especially resulting in organic electroluminescence devices having a good overall performance, especially a long lifetime, high efficiency and/or a low driving voltage.

The compounds of the present invention may also be used in further organic electronic devices than organic electroluminescence devices such as electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors and dye lasers.

Accordingly, a further subject of the present invention is directed to an organic electronic device, comprising a compound according to the present invention. The organic electronic device is preferably an organic electroluminescence device (EL device). The term organic EL device (organic electroluminescence device) is used interchangeably with the term organic light-emitting diode (OLED) in the present application.

The compounds of formula (I) can in principal be used in any layer of an EL device, but are preferably used as charge-transporting, especially electron-transporting, charge-blocking, especially hole-blocking, material. Particularly, the compounds of formula (I) are used as electron-transporting material and/or hole-blocking material for phosphorescence or fluorescence emitters.

Hence, a further subject of the present invention is directed to a material for an organic electroluminescence device comprising at least one compound of formula (I) according to the present invention.

A further subject of the present invention is directed to an organic electroluminescence device which comprises an organic thin film layer between a cathode and an anode, wherein the organic thin film layer comprises one or more layers and comprises a light emitting layer, and at least one layer of the organic thin film layer comprises at least one compound of formula (I) according to the present invention.

A further subject of the present invention is directed to an electronic equipment comprising the organic electroluminescence device according the present invention.

A further subject of the present invention is directed to the use of a compound of formula (I) according to the present invention in an organic electroluminescence device. In said embodiment the compound of formula (I) is preferably used in an electron-transporting zone of the organic electroluminescence device. In the meaning of the present invention, the electron-transporting zone includes at least an electron-transporting layer and preferably also an electron-injection layer and/or a hole-blocking layer.

A further subject of the present invention is directed to an emitting layer, comprising a compound of formula (I) according to the present invention.

A further subject of the present invention is directed to an electron-transporting layer comprising a compound of formula (I) according to the present invention. Preferably, the electron-transporting layer is provided between the cathode and the light emitting layer of an EL device such as an OLED.

A further subject of the present invention is directed to a hole-blocking layer comprising a compound of formula (I) according to the present invention. Preferably, the hole-blocking layer is provided between the electron-transporting layer and the light emitting layer of an EL device such as an OLED.

The terms unsubstituted or substituted divalent aromatic hydrocarbon group containing 6 to 30 ring atoms, an unsubstituted or substituted divalent heteroaromatic group containing 3 to 30 ring atoms, unsubstituted or substituted aromatic hydrocarbon group containing 6 to 30 ring atoms, an unsubstituted or substituted heteroaromatic group containing 3 to 30 ring atoms, unsubstituted or substituted heteroaromatic group containing 3 to 30 ring atoms containing at least one ring nitrogen, an unsubstituted or substituted alkyl group having 1 to 25 carbon atoms, an unsubstituted or substituted cycloalkyl group having 3 to 18 ring carbon atoms, are known in the art and generally have the following meaning, if said groups are not further specified in specific embodiments mentioned below:

The unsubstituted or substituted aromatic hydrocarbon group containing 6 to 30 ring atoms, preferably 6 to 24 ring atoms, more preferably 6 to 18 ring atoms may be a non-condensed aryl group or a condensed aryl group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, anthracenyl, chrysenyl, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, benzo[a]fluoranthenyl group, benzo[j]fluoranthenyl group, benzo[k]fluoranthenyl group and benzo[b]fluoranthenyl group, with phenyl group, naphthyl group, biphenyl group, terphenyl group, phenanthryl group, triphenylenyl group, fluorenyl group, spirobifluorenyl group anthracenyl, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, 9,9-dimethylfluorene-4-yl group, 9,9-diphenylfluorene-2-yl group, 9,9-diphenylfluorene-4-yl group, fluoranthene-3-yl group, fluoranthene-2-yl group, fluoranthene-8-yl, anthracen-3-yl and anthracen-9-yl group being most preferred.

The unsubstituted or substituted heteroaromatic group containing 3 to 30 ring atoms, preferably 5 to 18 ring atoms, may be a non-condensed heteroaromatic group or a condensed heteroaromatic group. Specific examples thereof include the residues of pyrrole ring, isoindole ring, imidazopyridine ring, imidazopyrimidine ring, imidazopyrazin ring, benzofuran ring, isobenzofuran ring, benzothiophene, dibenzothiophene ring, isoquinoline ring, quinoxaline ring, quinazoline, phenanthridine ring, phenanthroline ring, pyridine ring, pyrazine ring, pyrimidine ring, pyridazine ring, indole ring, quinoline ring, acridine ring, carbazole ring, furan ring, thiophene ring, benzoxazole ring, benzothiazole ring, benzimidazole ring, dibenzofuran ring, triazine ring, oxazole ring, oxadiazole ring, thiazole ring, thiadiazole ring, triazole ring, and imidazole ring with the residues of dibenzofuran ring, carbazole ring, and dibenzothiophene ring being preferred, and the residues of imidazo[1,2-a]pyridine, imidazo[1,5-a]pyridine, dibenzofuran-1-yl group, dibenzofuran-3-yl group, dibenzofuran-2-yl group, dibenzofuran-4-yl group, 9-phenylcarbazole-3-yl group, 9-phenylcarbazole-2-yl group, 9-phenylcarbazole-4-yl group, dibenzothiophene-2-yl group, and dibenzothiophene-4-yl, dibenzothiophene-1-yl group, and dibenzothiophene-3-yl group being more preferred.

Examples of the unsubstituted or substituted alkyl group having 1 to 25 carbon atoms, preferably 1 to 8 carbon atoms, are methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group and 1-methylpentyl group.

Further preferred are alkyl groups having 1 to 6 carbon atoms. Examples of the alkyl group having 1 to 6 carbon atoms are methyl group, ethyl group, n-propyl group, isopropyl group, n-butyl group, s-butyl group, isobutyl group, t-butyl group, n-pentyl group, n-hexyl group, neopentyl group and 1-methylpentyl group, with methyl group, ethyl group, n-propyl group, isopropyl group, n-butyl group, s-butyl group, isobutyl group and t-butyl group being preferred.

Examples of the unsubstituted or substituted cycloalkyl group having 3 to 18 ring carbon atoms, preferably 3 to 12 ring carbon atoms include cyclopropyl group, cyclobutyl group, cyclopentyl group, cyclohexyl group, cyclooctyl group, and adamantyl group. Most preferred are cycloalkyl groups having 3 to 6 ring carbon atoms, i.e. a cyclopropyl group, a cyclobutyl group, a cyclopentyl group or a cyclohexyl group.

The term “unsubstituted or substituted divalent aromatic hydrocarbon group” has according to the present invention the following meaning:

An unsubstituted divalent aromatic hydrocarbon group, is an aromatic hydrocarbon group comprising two bonding sites to neighbouring groups, but no further substituents, i.e. all other possible bonding sites in said group are substituted by hydrogen.

A substituted divalent aromatic hydrocarbon group, is an aromatic hydrocarbon group comprising two bonding sites to neighbouring groups, but additionally at least one further substituent, i.e. at least one of the other possible bonding sites in said group is substituted by a residue different from hydrogen. Suitable substituents are mentioned below.

The unsubstituted or substituted divalent aromatic hydrocarbon group containing 6 to 30 ring atoms, preferably 6 to 18 ring atoms, more preferably 6 to 14 ring atoms, may be a non-condensed or a condensed divalent aromatic hydrocarbon group. Specific examples thereof include phenylene group, naphthylene group, biphenylene group, terphenylene group, quaterphenylene group, fluoranthene-diyl group, triphenylene-diyl group, phenanthrene-diyl group, fluorene-diyl group, anthracene-diyl, chrysene-diyl, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylene-diyl group, dibenzo[a,c]triphenylene-diyl group, benzo[a]fluoranthene-diyl group, benzo[j]fluoranthene-diyl group, benzo[k]fluoranthene-diyl group and benzo[b]fluoranthene-diyl group, with phenylene group, naphthylene group, biphenylene group, terphenylene group, phenanthrene-diyl group, triphenylene-diyl group, fluorene-diyl group, spirobifluorene-diyl group, anthracene-diyl and fluoranthene-diyl group being preferred.

The term “unsubstituted or substituted divalent heteroaromatic group” has according to the present invention the following meaning:

An unsubstituted divalent heteroaromatic group, is a heteroaromatic group comprising two bonding sites to neighbouring groups, but no further substituents, i.e. all other possible bonding sites in said group are substituted by hydrogen.

A substituted divalent heteroaromatic group, is a heteroaromatic group comprising two bonding sites to neighbouring groups, but additionally at least one further substituent, i.e. at least one of the other possible bonding sites in said group is substituted by a residue different from hydrogen. Suitable substituents are mentioned below.

The unsubstituted or substituted divalent heteroaromatic group containing 3 to 30 ring atoms, preferably 5 to 18 ring atoms, may be a non-condensed heteroaromatic group or a condensed heteroaromatic group. Specific examples thereof include pyrrole-diyl, isoindole-diyl, benzofuran-diyl, isobenzofuran-diyl, benzothiophene-diyl, dibenzothiophene-diyl, isoquinoline-diyl, quinoxaline-diyl, quinazoline-diyl, phenanthridine-diyl, phenanthroline-diyl, pyridine-diyl, pyrazine-diyl, pyrimidine-diyl, pyridazine-diyl, indole-diyl, quinoline-diyl, acridine-diyl, carbazole-diyl, furan-diyl, thiophene-diyl, benzoxazole-diyl, benzothiazole-diyl, benzimidazole-diyl, dibenzofuran-diyl, triazine-diyl, oxazole-diyl, oxadiazole-diyl, thiazole-diyl, thiadiazole-diyl, triazole-diyl, and imidazole-diyl with the residues of dibenzofuran-diyl, carbazole-diyl, and dibenzothiophene-diyl being preferred.

Examples of the optional substituent(s) indicated by "substituted or unsubstituted" and "may be substituted" referred to above or hereinafter include a halogen atom, a cyano group, an alkyl group having 1 to 25, preferably 1 to 8 carbon atoms, a cycloalkyl group having 3 to 18, preferably 3 to 12 ring carbon atoms, an alkoxy group having 1 to 25, preferably 1 to 8 carbon atoms, an alkylamino group having 1 to 25 carbon atoms, preferably 1 to 5 carbon atoms, a carboxyalkyl group having 1 to 25 carbon atoms, preferably 1 to 5 carbon atoms, a carboxamidalkyl group having 1 to 25 carbon atoms, preferably 1 to 5 carbon atoms, a silyl group, a $C_6$ to $C_{24}$ aryl group, preferably a $C_6$ to $C_{18}$ aryl group, an aryloxy group having 6 to 24, preferably 6 to 18 ring carbon atoms, an aralkyl group having 7 to 24, preferably 7 to 20 carbon atoms, an alkylthio group having 1 to 25, preferably 1 to 5 carbon atoms, an arylthio group having 6 to 24, preferably 6 to 18 ring carbon atoms, an arylamino group having 6 to 30 carbon atoms, preferably 6 to 18 carbon atoms, a carboxyaryl group having 6 to 24 carbon atoms, preferably 6 to 18 carbon atoms, a carboxamidaryl group having 6 to 24 carbon atoms, preferably 6 to 18 carbon atoms in its aryl group, a diaryl phosphine oxide group having 6 to 24 carbon atoms, preferably 6 to 18 carbon atoms in each aryl group, and a heteroaromatic group having 3 to 30 ring atoms, preferably 5 to 18 ring atoms. The substituents may in turn be unsubstituted or substituted, preferably unsubstituted.

The alkyl group having 1 to 25, preferably 1 to 8 carbon atoms, the $C_6$ to $C_{24}$ aryl group, preferably $C_6$ to $C_{18}$ aryl group, and cycloalkyl group having 3 to 18 ring carbon atoms, preferably 3 to 12 ring carbon atoms, are defined above.

Examples of the alkenyl group having 2 to 25 carbon atoms include those disclosed as alkyl groups having 2 to 25 carbon atoms but comprising at least one double bond, preferably one, or where possible, two or three double bonds.

Examples of the alkynyl group having 2 to 25 carbon atoms include those disclosed as alkyl groups having 2 to 25 carbon atoms but comprising at least one triple bond, preferably one, or where possible, two or three triple bonds.

The silyl group is an alkyl and/or aryl substituted silyl group. Examples of alkyl and/or aryl substituted silyl groups include alkylsilyl groups having 1 to 10 carbon atoms, preferably 1 to 5 carbon atoms, including trimethylsilyl group, triethylsilyl group, tributylsilyl group, dimethylethylsilyl group, t-butyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, alkylarylsilyl groups having 6 to 30 carbon atoms, preferably 6 to 18 carbon atoms in the aryl part and 1 to 10 carbon atoms, preferably 1 to 5 carbon atoms, in the alkyl part including phenyldimethylsilyl group, diphenylmethylsilyl group, diphenyltertiarybutylsilyl group, and arylsilyl groups having 6 to 30 carbon atoms, preferably 6 to 18 carbon atoms, including a triphenylsilyl group, with trimethylsilyl, triphenylsilyl, diphenyltertiarybutylsilyl group and t-butyldimethylsilyl group being preferred.

Examples of halogen atoms include fluorine, chlorine, bromine, and iodine.

Examples of an alkylamino group (alkyl substituted amino group), preferably an alkylamino group having 1 to 25 ring carbon atoms include those having an alkyl portion selected from the alkyl groups mentioned above.

Examples of an arylamino group (aryl substituted amino group), preferably an arylamino group having 6 to 24 ring carbon atoms include those having an aryl portion selected from the aromatic hydrocarbon groups mentioned above.

Examples of the optional aralkyl group having 6 to 30 ring carbon atoms include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

Examples of a carboxyalkyl group (alkyl substituted carboxyl group), preferably a carboxyalkyl group having 1 to 25 carbon atoms, preferably 1 to 5 carbon atoms, include those having an alkyl portion selected from the alkyl groups mentioned above.

Examples of a carboxyaryl group (aryl substituted carboxyl group), preferably a carboxyaryl group having 6 to 24 carbon atoms, preferably 6 to 18 carbon atoms, include those having an aryl portion selected from the aromatic hydrocarbon groups mentioned above.

Examples of a carboxamidalkyl group (alkyl substituted amide group), preferably a carboxamidalkyl group having 1 to 25 carbon atoms, preferably 1 to 5 carbon atoms include those having an alkyl portion selected from the alkyl groups mentioned above.

Examples of a carboxamidaryl group (aryl substituted amide group), preferably a carboxamidaryl group having 6 to 24 carbon atoms, preferably 6 to 18 carbon atoms, include those having an aryl portion selected from the aromatic hydrocarbon groups mentioned above.

Examples of a diaryl phosphine oxide group, preferably a diaryl phosphine oxide group having 6 to 24 carbon atoms, preferably 6 to 18 carbon atoms in each aryl group, include those having aryl portions selected from the aromatic hydrocarbon groups mentioned above.

The optional substituent is preferably a halogen atom, a cyano group, an alkyl group having 1 to 25 carbon atoms, an aryl group having 6 to 24 ring carbon atoms, preferably 6 to 18 ring carbon atoms, and an heterocyclic group having 3 to 30 ring atoms, preferably 5 to 18 ring atoms; more preferably a cyano group, a phenyl group, a naphthyl group, a biphenyl group, a terphenyl group, a phenanthryl group, a triphenylenyl group, a fluorenyl group, a spirobifluorenyl group, a fluoranthenyl group, a residue based on a dibenzofuran ring, a residue based on a carbazole ring, and a residue based on a dibenzothiophene ring, a methyl group, an ethyl group, a n-propyl group, an isopropyl group, a n-butyl group, a s-butyl group, an isobutyl group, a t-butyl group, a cyclopentyl group, and a cyclohexyl group.

The optional substituent mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The "carbon number of a to b" in the expression of "substituted or unsubstituted X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium.

The compounds of formula (I)

$L_3$ represents a group of the following formula

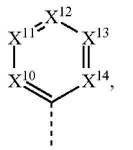

wherein $X^{10}$ represents N or $CR^{10}$;

$X^{11}$ represents N or $CR^{11}$;

$X^{12}$ represents N or $CR^{12}$;

$X^{13}$ represents N or $CR^{13}$;

$X^{14}$ represents N or $CR^{14}$;

wherein at least one of $X^{10}$, $X^{11}$, $X^{12}$, $X^{13}$ and $X^{14}$ is N, preferably exactly one of $X^{10}$, $X^{11}$, $X^{12}$, $X^{13}$ and $X^{14}$ is N; and one of $X^{10}$, $X^{11}$, $X^{12}$, $X^{13}$ and $X^{14}$ is

C----, wherein ---- is a bonding site.

More preferably, $L_3$ represents an unsubstituted divalent pyridine group.

n represents 0 or 1.

The compounds of formula (I) are therefore represented by formula (Ia), in the case that n is 0:

(Ia)

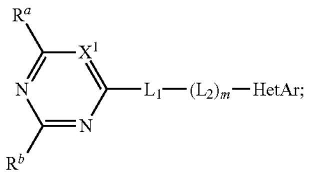

or by formula (Ib), in the case that n is 1:

(Ib)

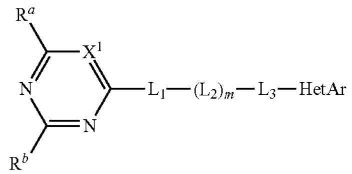

wherein the residues, groups and indices are described above and below.

In formula (Ia)—in the case that $X^1$ is $CR^1$—m is at least 2. In formula (Ib)—in the case that $X^1$ is $CR^1$—m is at least 1.

In formula (Ia)—in the case that $X^1$ is N—m is at least 1. In formula (Ib)—in the case that $X^1$ is N—m is 0, 1, 2 or 3.

HetAr is represented by one of formula (II) or (III)

(II)

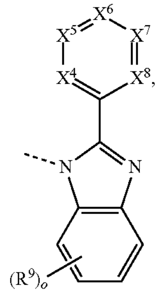

(III)

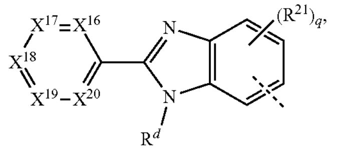

or—in the case that n is 1—HetAr is represented by one of formula (II), (III) or (IV)

(IV)

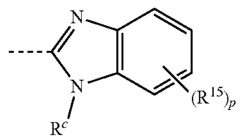

$X^4$ represents N or $CR^4$;

$X^5$ represents N or $CR^5$;

$X^6$ represents N or $CR^6$;

$X^7$ represents N or $CR^7$;

$X^8$ represents N or $CR^8$;

wherein at least one of $X^4$, $X^5$, $X^6$, $X^7$ and $X^8$ is N, preferably exactly one of $X^4$, $X^5$, $X^6$, $X^7$ and $X^8$ is N;

$X^{16}$ represents N or $CR^{16}$;

$X^{17}$ represents N or $CR^{17}$;

$X^{18}$ represents N or $CR^{18}$;

$X^{19}$ represents N or $CR^{19}$;

$X^{20}$ represents N or $CR^{20}$;

wherein at least one of $X^{16}$, $X^{17}$, $X^{18}$, $X^{19}$ and $X^{20}$ is N, preferably exactly one of $X^{16}$, $X^{17}$, $X^{18}$, $X^{19}$ and $X^{20}$ is N;

o and p each independently represents 0, 1, 2, 3 or 4, preferably 0, 1 or 2, more preferably 0;

q represents 0, 1, 2 or 3, preferably 0, 1 or 2, more preferably 0; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ each independently represents hydrogen, an unsubstituted or substituted aromatic hydrocarbon group containing 6 to 30 ring atoms or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms or CN; preferably, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ each independently represents hydrogen, unsubstituted or substituted phenyl, unsubstituted or substituted pyridyl, an unsubstituted or substituted alkyl group having 1 to 4 carbon atoms, an unsubstituted or substituted cycloalkyl group having 5 to 6 ring carbon atoms or CN; more preferably hydrogen, unsubstituted phenyl, unsubstituted pyridyl or an unsubstituted alkyl group having 1 to 4 carbon atoms; or two adjacent groups $R^9$, two adjacent groups $R^{15}$ or two adjacent groups $R^{21}$ and/or two adjacent groups selected from $R^4$, $R^5$, $R^6$, $R^7$, $R^8$, $R^{10}$, $R^{11}$, $R^{12}$, $R^{13}$, $R^{14}$, $R^{16}$, $R^{17}$, $R^{18}$, $R^{19}$, $R^{20}$ can form together a substituted or unsubstituted carbocyclic or heterocyclic ring.

Most preferably, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are hydrogen.

$R^c$ and $R^d$ each independently represents an unsubstituted or substituted aromatic hydrocarbon group containing 6 to 30 ring atoms or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms; preferably, $R^c$ and $R^d$ each independently represents an unsubstituted or substituted aromatic hydrocarbon group containing 6 to 18 ring atoms, more preferably unsubstituted or substituted phenyl, most preferably unsubstituted phenyl.

The dotted line is a bonding site.

In the case that n is 1 and the group $L_3$ is present, $-(L_3)_n$-HetAr is represented by one of formula (IIa), (IIb), (IIc), (IIIa), (IIIb), (IIIc), (IVa), (IVb) or (IVc)

(IIa)

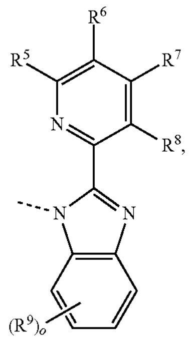

-continued (IIb)

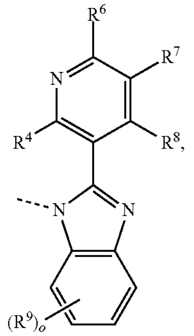

(IIc)

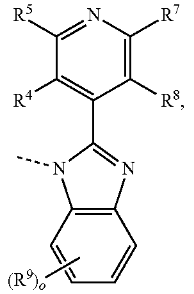

(IIIa)

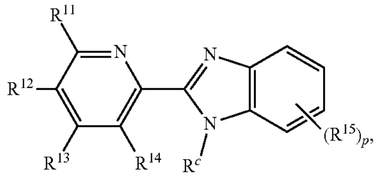

(IIIb)

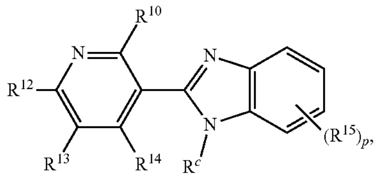

(IIIc)

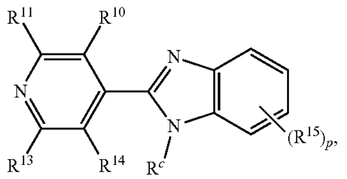

(IVa)

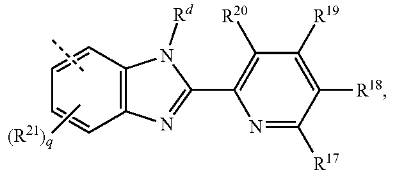

(IVb)

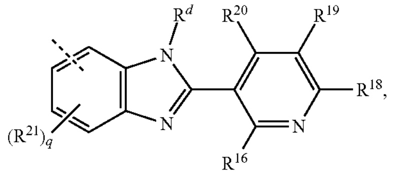

-continued (IVc)

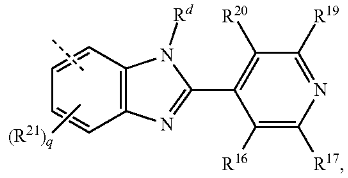

wherein one of one of $R^{11}$, $R^{12}$, $R^{13}$ and $R^{14}$ in formula (IIIa), one of one of $R^{10}$, $R^{12}$, $R^{13}$ and $R^{14}$ in formula (IIIb) and one of one of $R^{10}$, $R^{11}$, $R^{13}$ and $R^{14}$ in formula (IIIc) is a bonding site.

Preferably, in the case that n is 1 and the group $L_3$ is present, $-(L_3)_n$-HetAr is represented by one of formula (IIia), (IIib), (IIic), (IIIib), (IIIic), (IVia), (IVib) or (IVic)

(IIia)

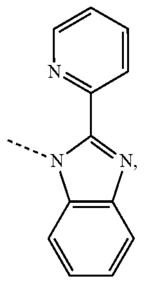

(IIib)

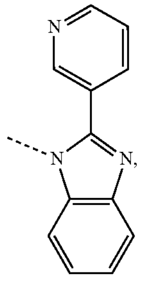

(IIic)

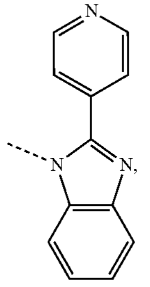

(IIIia)

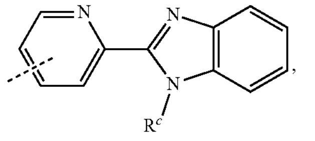

(IIIib)

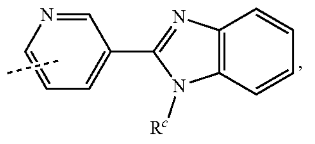

-continued (IIIic)

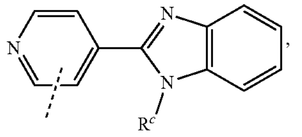

(IVia)

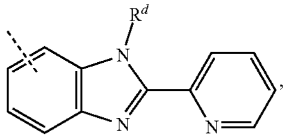

(IVib)

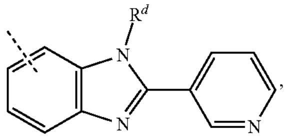

(IVic)

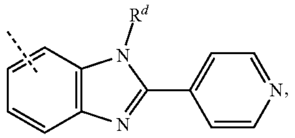

wherein the dotted line is a bonding site.

In the compounds of formula (I), $L_2$ represents an unsubstituted or substituted divalent aromatic hydrocarbon group containing 6 to 30 ring atoms or an unsubstituted or substituted divalent heteroaromatic group containing 3 to 30 ring atoms; preferably, $L_2$ represents an unsubstituted or substituted divalent aromatic hydrocarbon group containing 6 to 30 ring atoms, preferably 6 to 24 ring atoms, more preferably 6 to 18 ring atoms, more preferably $L_2$ represents an unsubstituted or substituted divalent phenyl group, an unsubstituted or substituted divalent naphthyl group, an unsubstituted or substituted divalent anthryl group, an unsubstituted or substituted phenythrenyl group, an unsubstituted or substituted triphenylenyl group, a 9,9-dimethyl fluorene group, or an unsubstituted or substituted 9,9-diphenyl fluorene group. Preferably, the groups $L_2$ are unsubstituted.

Most preferably, $L_2$ represents unsubstituted 1,4-phenylene, unsubstituted 1,3-phenylene, unsubstituted 1,4-naphthalene, unsubstituted 1,5-naphthalene, unsubstituted 1,6-naphthylene, unsubstituted 2,6-naphthylene, unsubstituted 2,7-9,9-diphenyl-fluorene, unsubstituted 2,5-9,9-diphenyl-fluorene, unsubstituted 2,7-tripenylene, or unsubstituted 9,10-anthryl.

Further most preferably, $L_2$ represents unsubstituted 1,4-phenylene, unsubstituted 1,3-phenylene, unsubstituted 1,4-naphthalene, unsubstituted 1,5-naphthalene, unsubstituted 1,6-naphthylene, unsubstituted 2,6-naphthylene, or unsubstituted 9,10-anthryl.

m represents 0, 1, 2 or 3, preferably 0, 1 or 2, more preferably 1 or 2; wherein the groups $L_2$ may be the same or different in the case that m is 2 or 3; wherein the sum of m and n is at least 1 and—in the case that $X^1$ is $CR^1$—the sum of m and n is at least 2.

Preferably, the sum of m and n in formula (I) is 1 or 2 and—in the case that $X^1$ is $CR^1$—the sum of m and n is preferably 2.

$L_1$ represents an unsubstituted divalent aromatic hydrocarbon group of the following formula

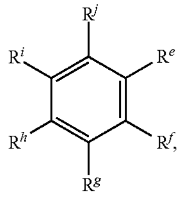

wherein $R^e$, $R^f$, $R^g$, $R^h$, $R^i$ and $R^j$ each independently represents hydrogen, an unsubstituted or substituted aromatic hydrocarbon group containing 6 to 30 ring atoms or, an unsubstituted or substituted alkyl group having 1 to 25 carbon atoms; preferably, $R^e$, $R^f$, $R^g$, $R^h$, $R^i$ and $R^j$ each independently represents hydrogen, unsubstituted or substituted phenyl, or an unsubstituted or substituted alkyl group having 1 to 4 carbon atoms; more preferably hydrogen, unsubstituted phenyl, or an unsubstituted alkyl group having 1 to 4 carbon atoms, more preferably hydrogen; or at least two adjacent residues $R^e$, $R^f$, $R^g$, $R^h$, $R^i$ and $R^j$ form together a 6-membered aromatic ring; or an unsubstituted divalent heteroaromatic group containing 3 to 30 ring atoms; wherein two of the residues $R^e$, $R^f$, $R^g$, $R^h$, $R^i$ and $R^j$ are bonding sites.

Preferably, $L_1$ represents an unsubstituted or substituted divalent phenyl group, an unsubstituted or substituted divalent naphthyl group, an unsubstituted or substituted divalent anthryl group, an unsubstituted or substituted phenythrenyl group, an unsubstituted or substituted triphenylenyl group, preferably unsubstituted 1,4-phenylene, unsubstituted 1,3-phenylene, unsubstituted 1,4-naphthalene, unsubstituted 1,5-naphthalene, unsubstituted 1,6-naphthylene, unsubstituted 2,6-naphthylene, unsubstituted 2,7-tripenylene, or unsubstituted 9,10-anthryl. Preferably, the groups $L_1$ are unsubstituted.

Most preferably, $L_1$ represents unsubstituted 1,4-phenylene, unsubstituted 1,3-phenylene, unsubstituted 1,4-naphthalene, unsubstituted 1,5-naphthalene, unsubstituted 1,6-naphthylene, unsubstituted 2,6-naphthylene or unsubstituted 9,10-anthryl.

The group $-L_1-(L_2)_m-$ is preferably represented by:

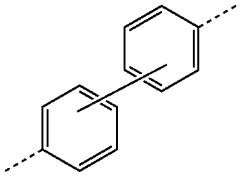

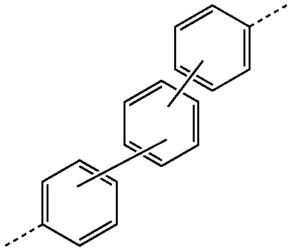

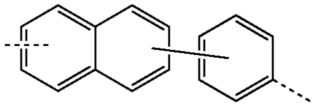

-continued

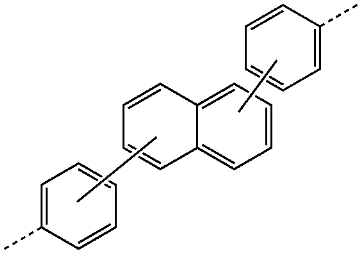

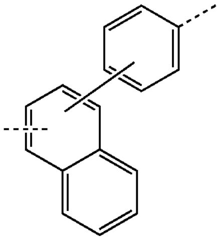

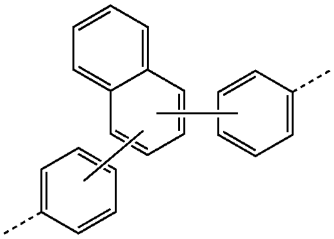

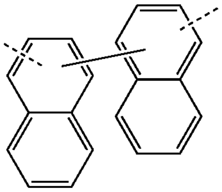

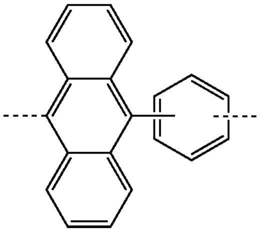

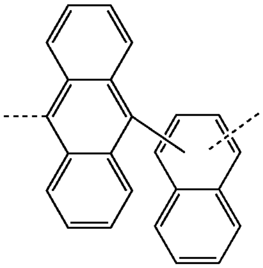

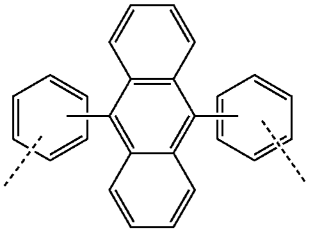

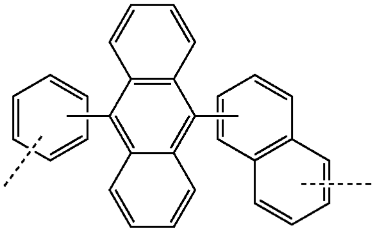

-continued
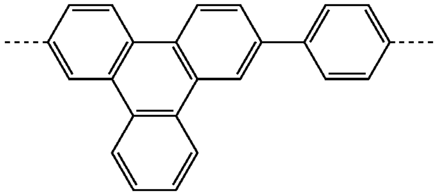
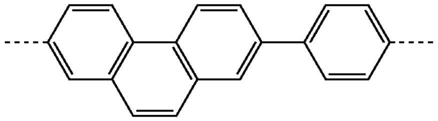
-continued
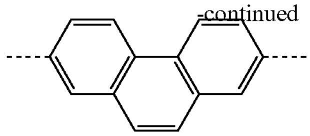
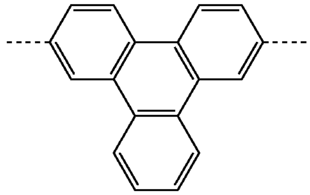
wherein the dotted lines are bonding sites.
Below, examples for compounds of formula (I) are given:
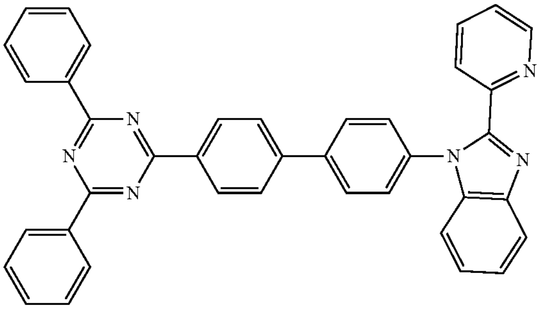
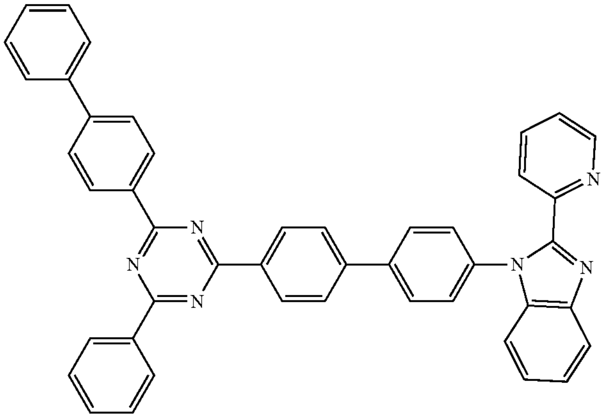
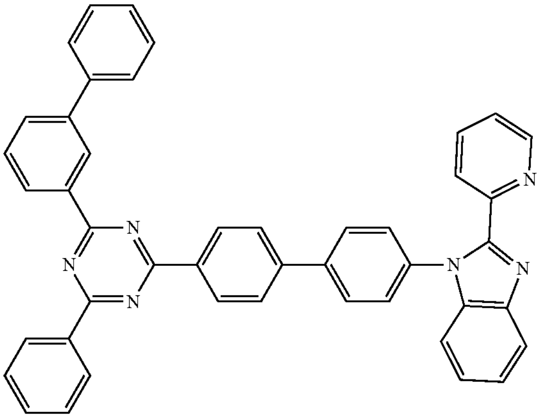
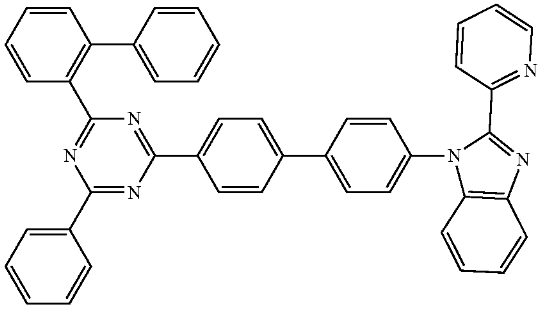

-continued
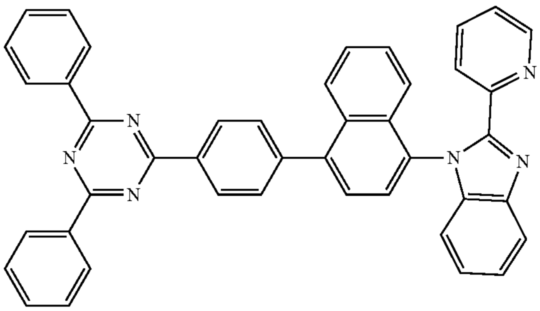
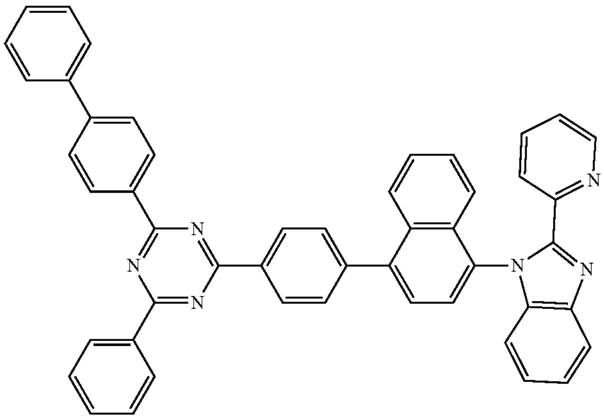
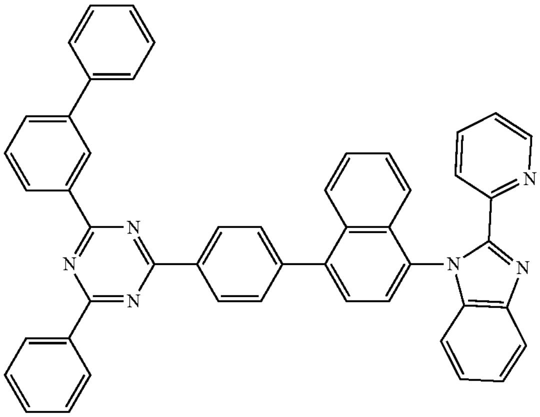
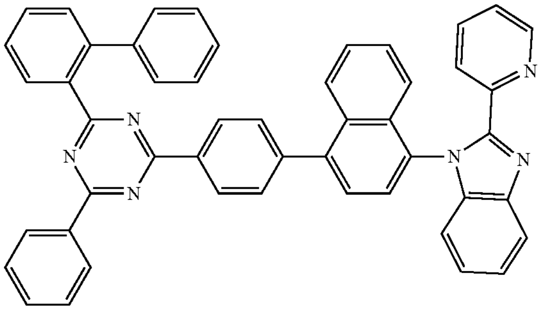
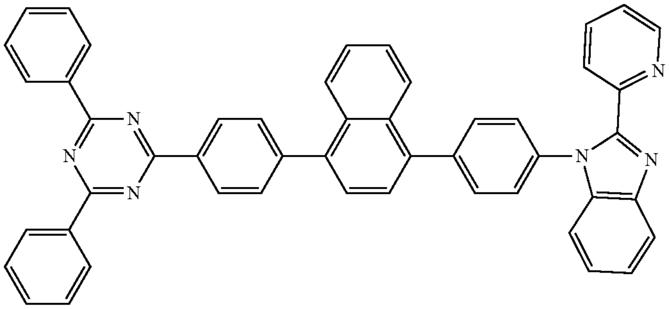
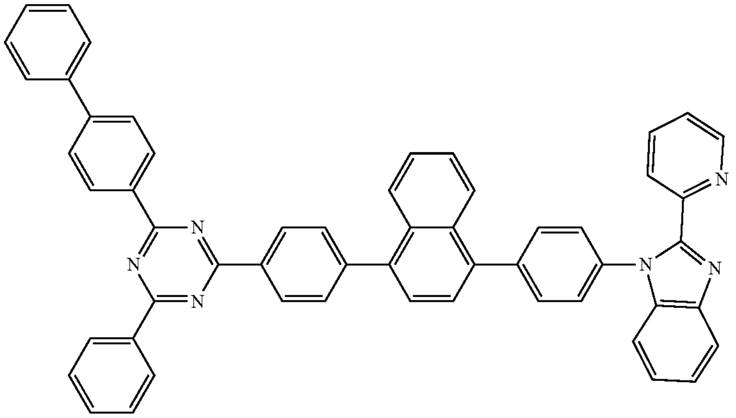

-continued
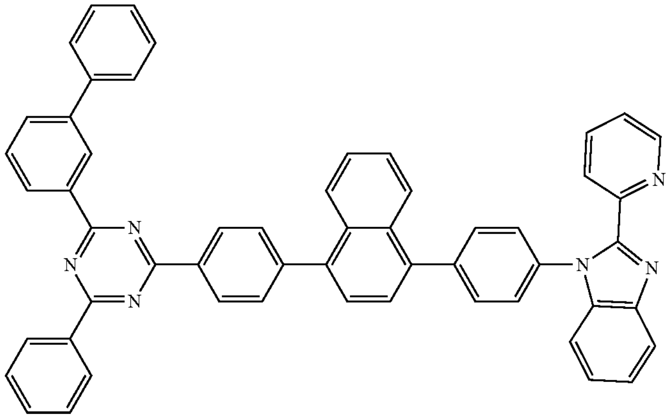
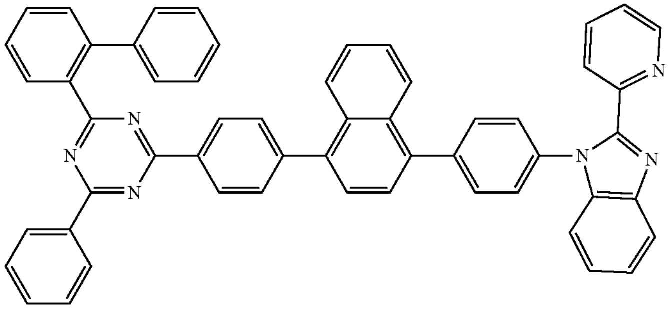
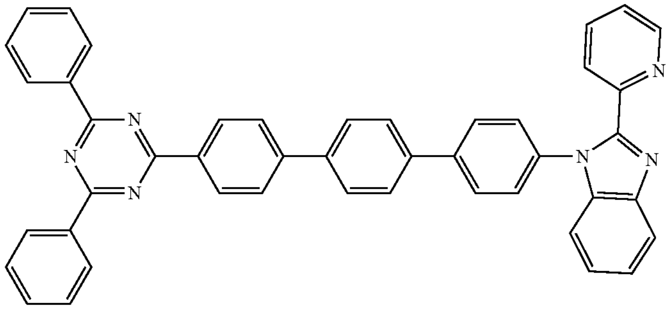
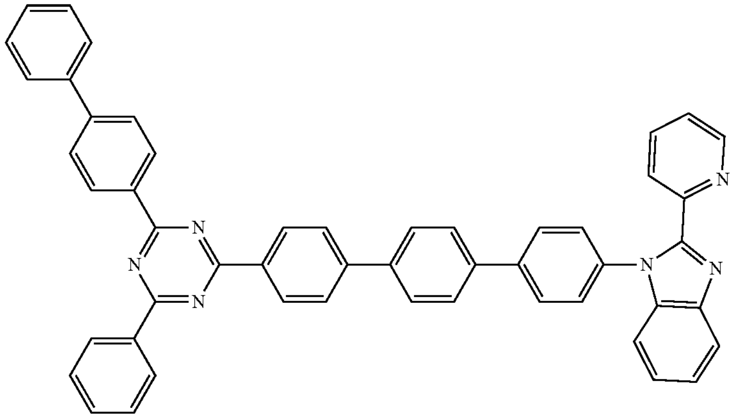

-continued
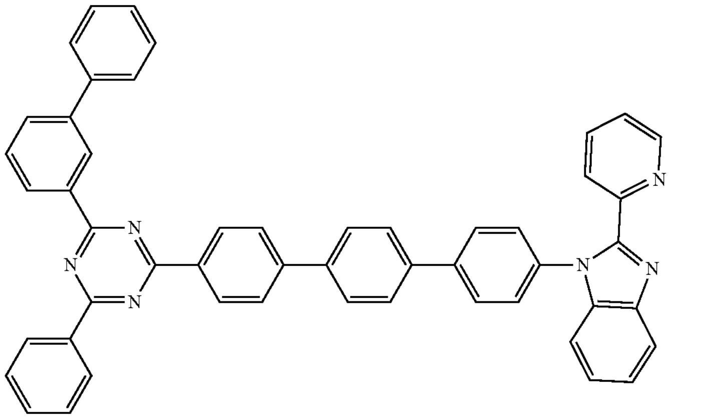
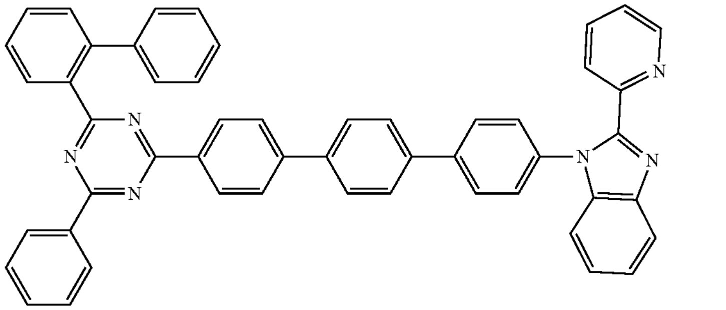
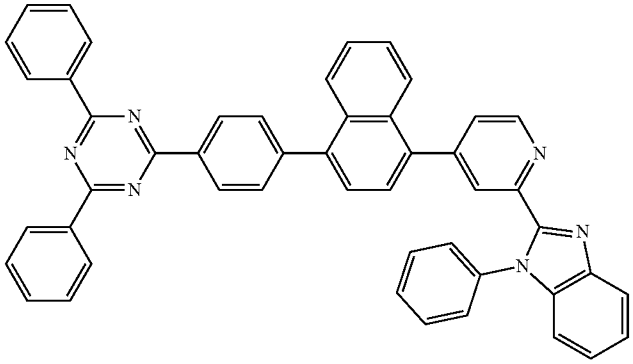
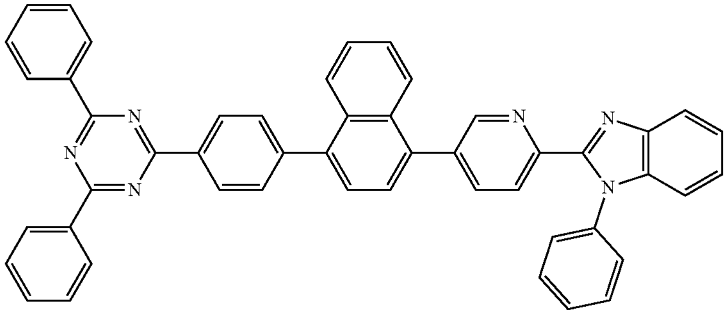
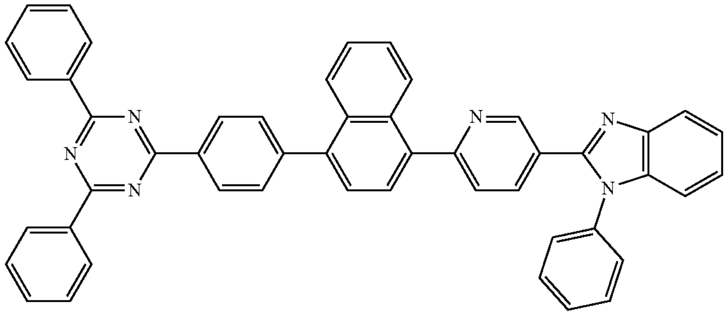

-continued
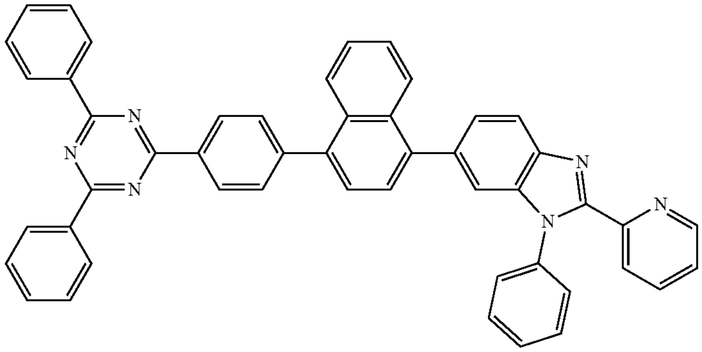
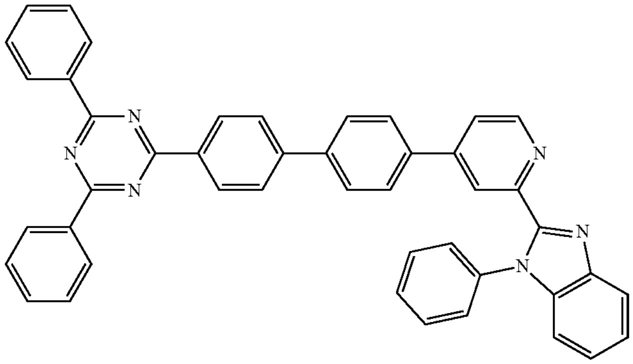
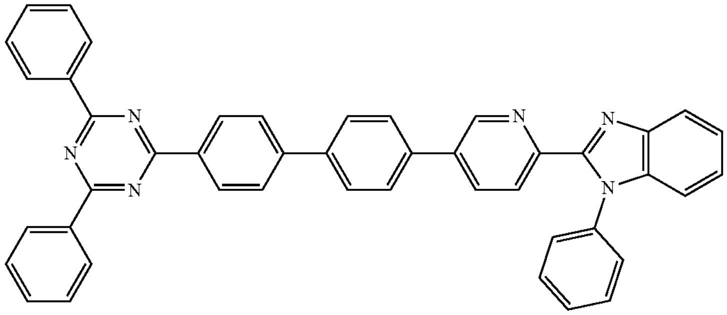
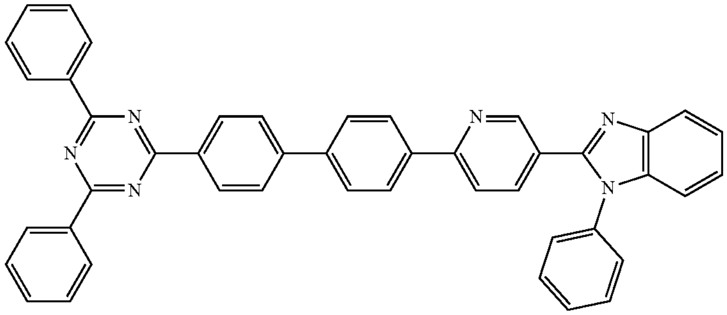
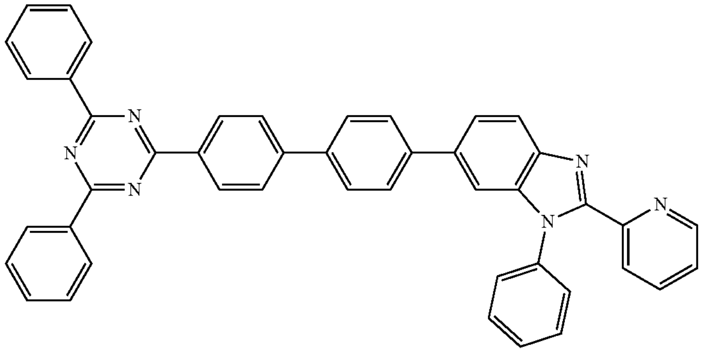

-continued
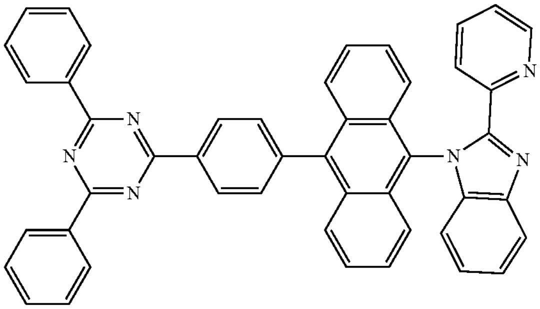
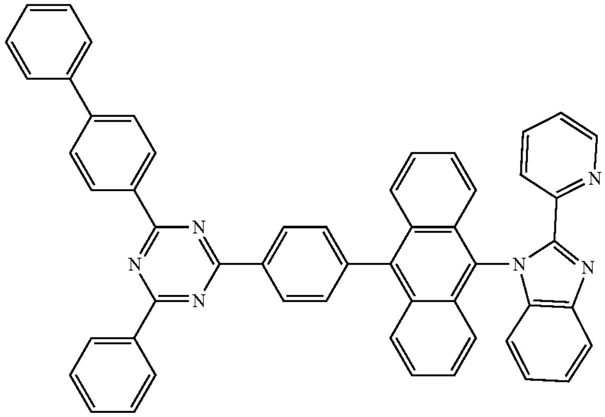
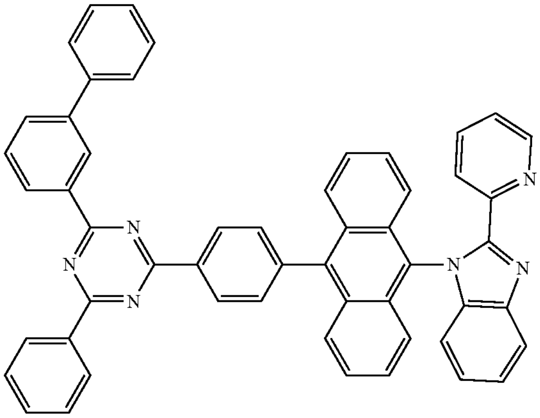
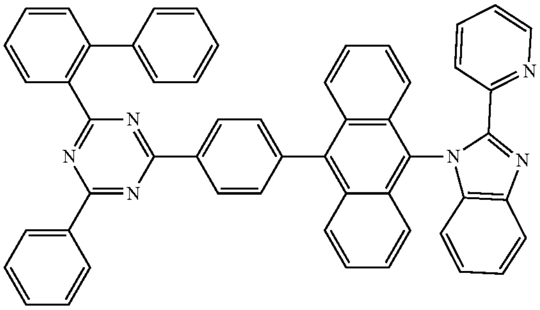
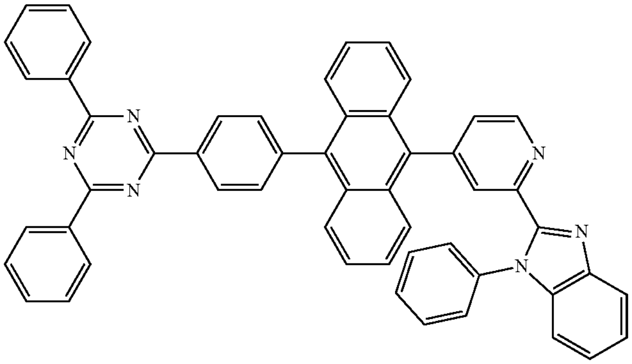
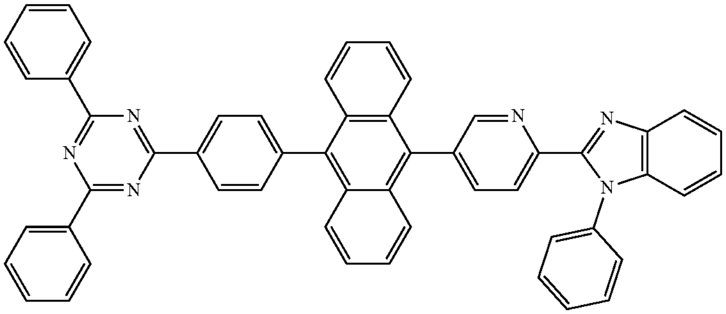

-continued
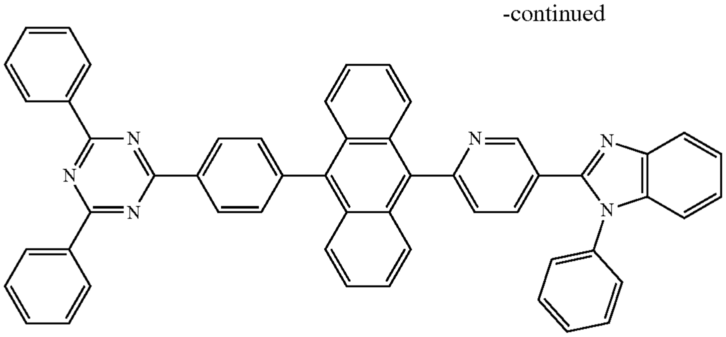
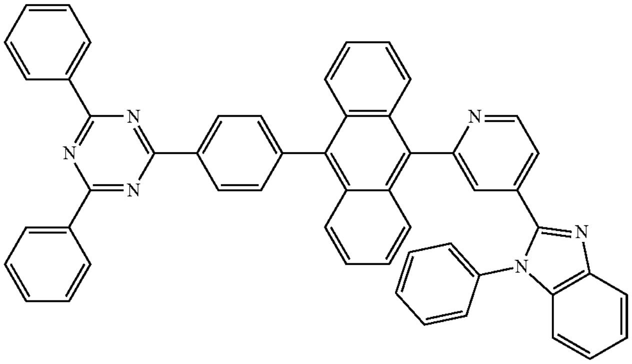
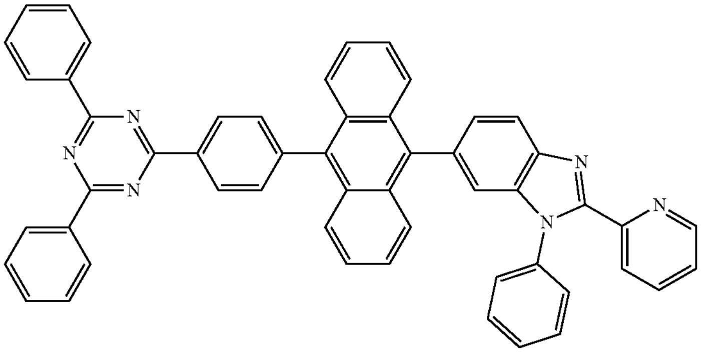
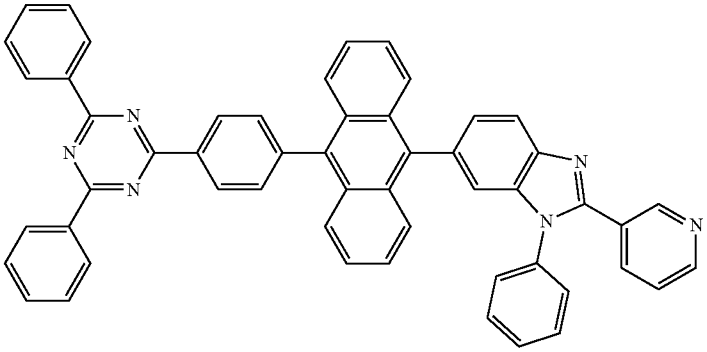
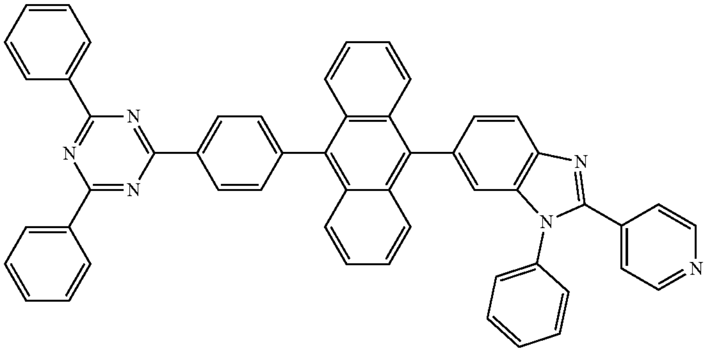

-continued
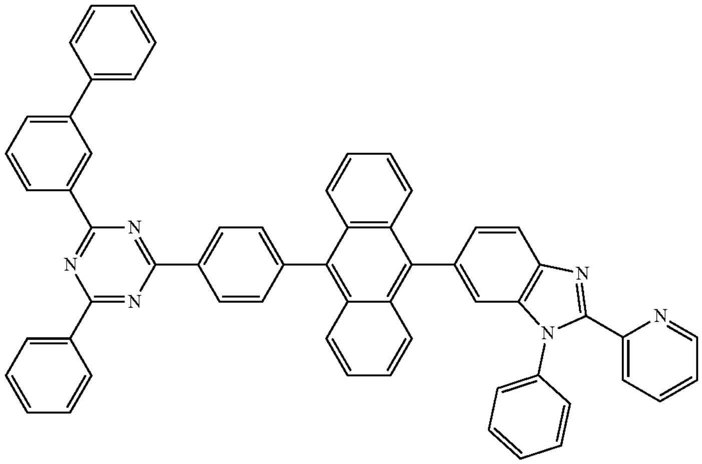
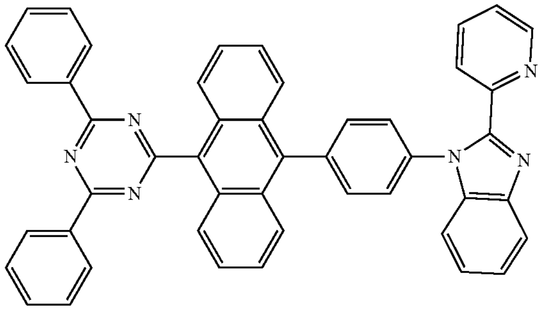
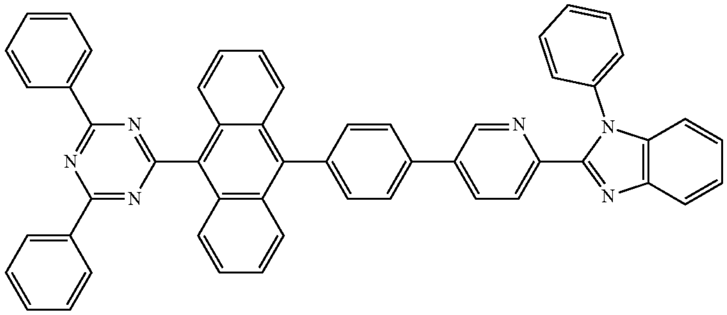
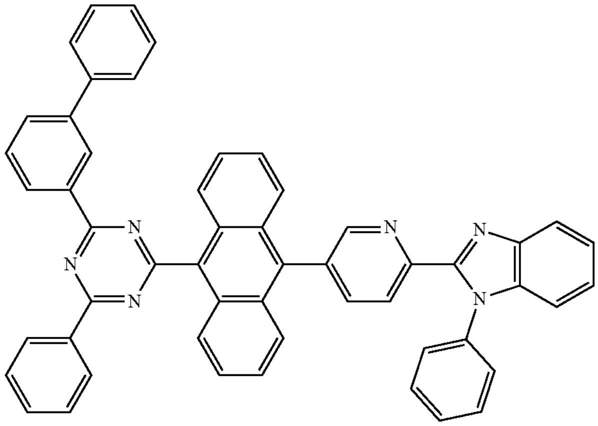

-continued
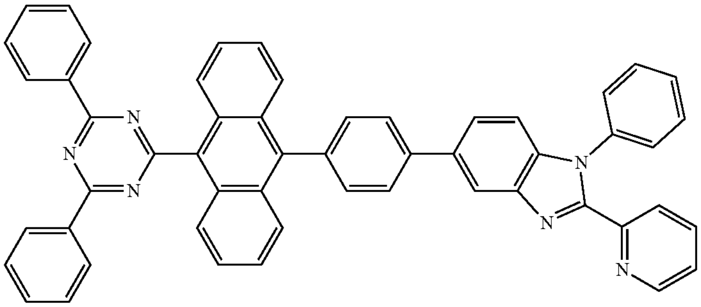
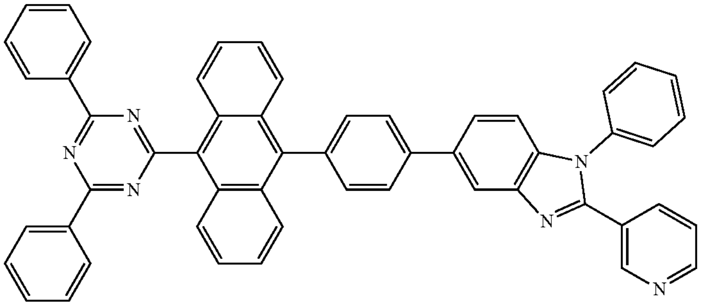
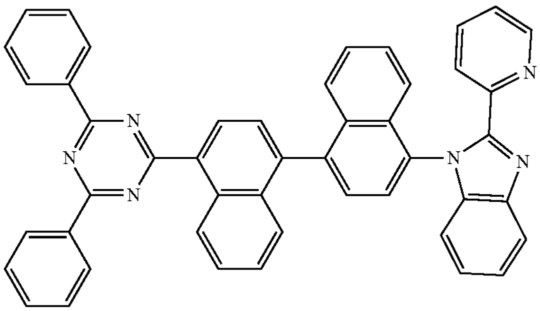
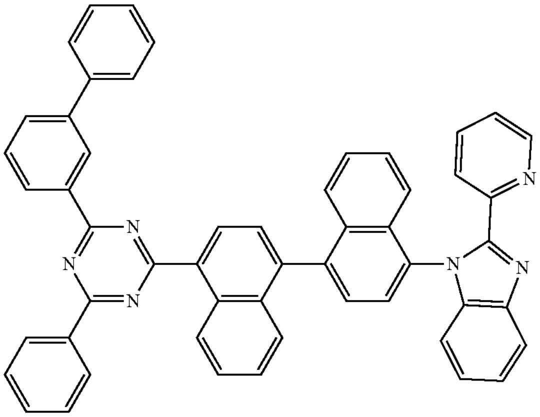
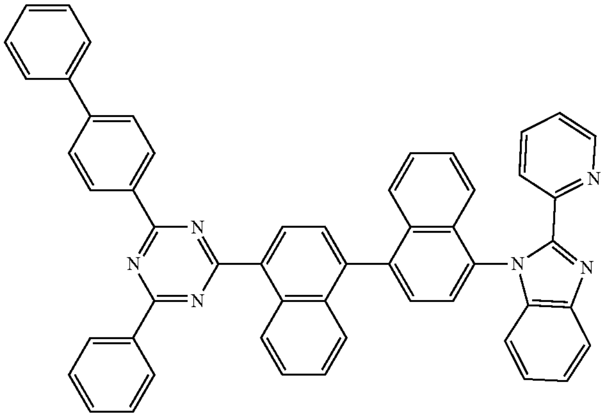
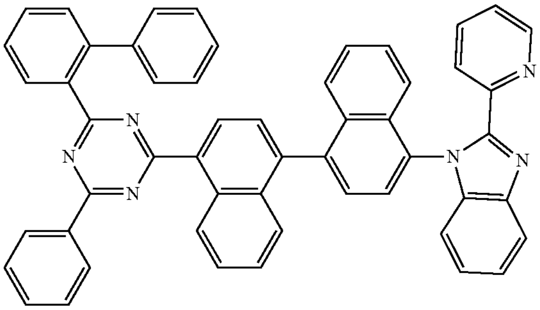

-continued
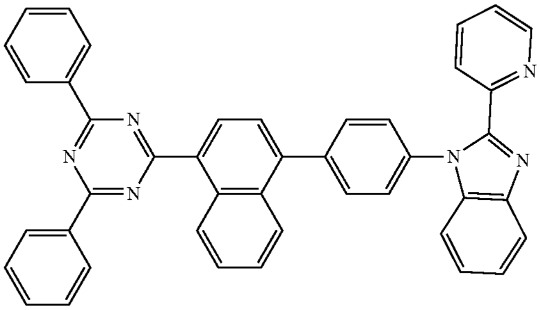
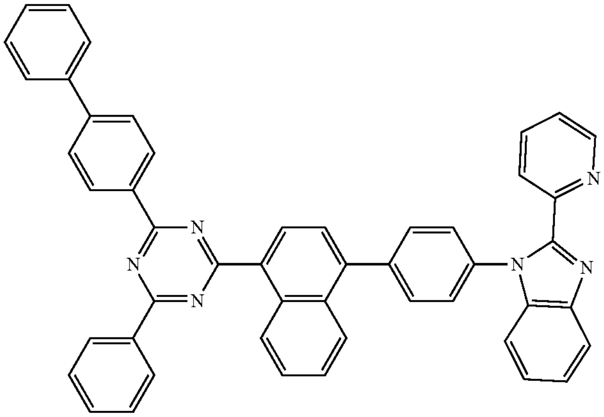
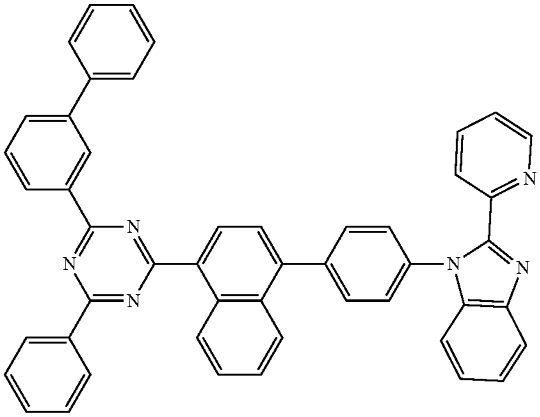
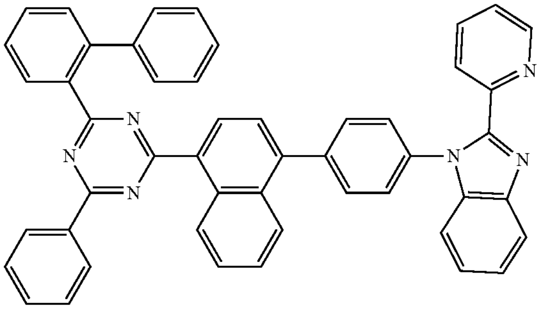
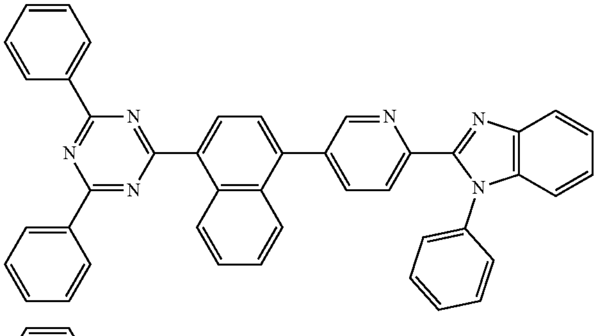
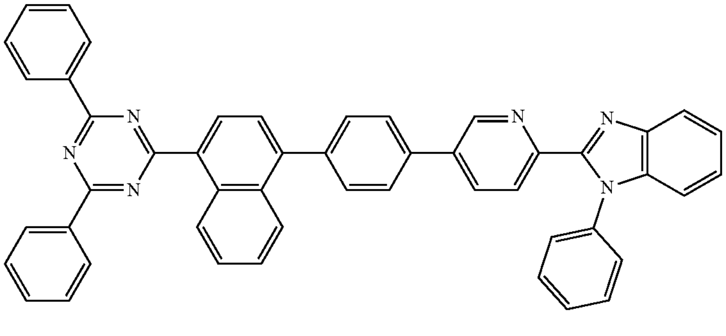

-continued
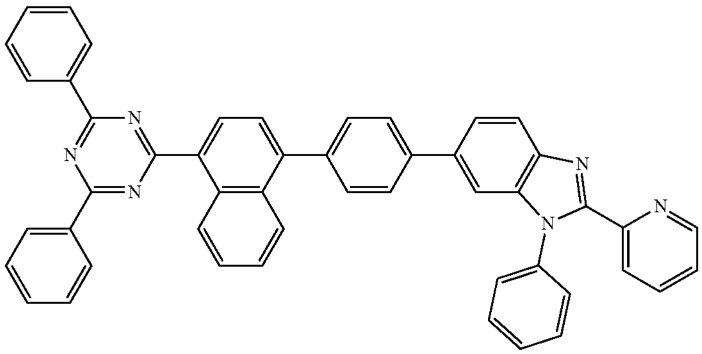
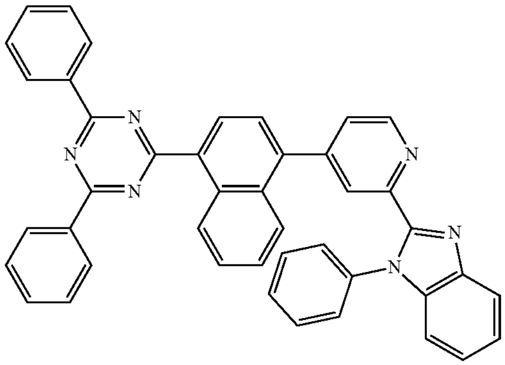
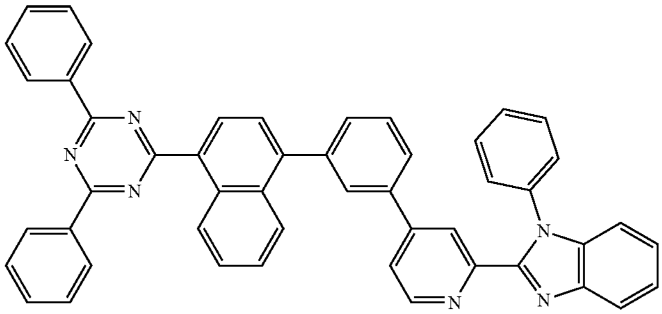
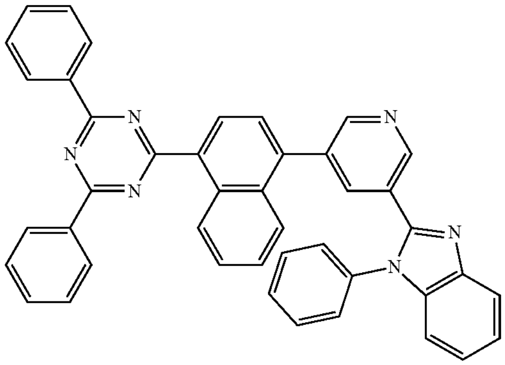
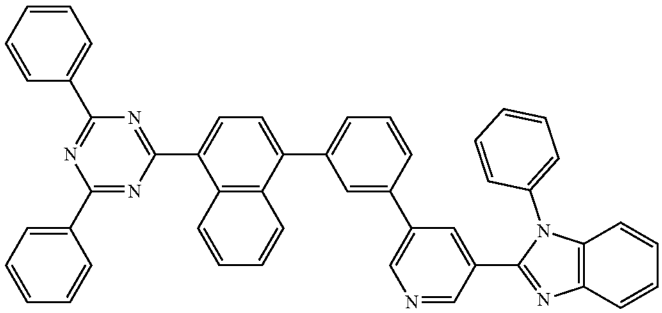

-continued
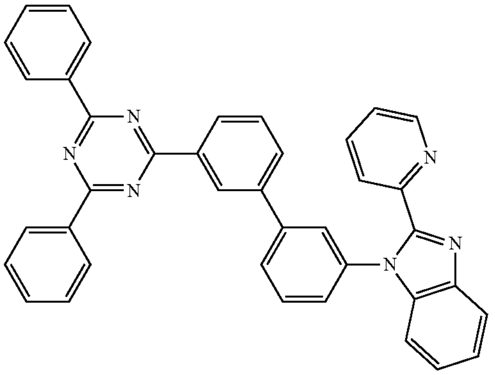
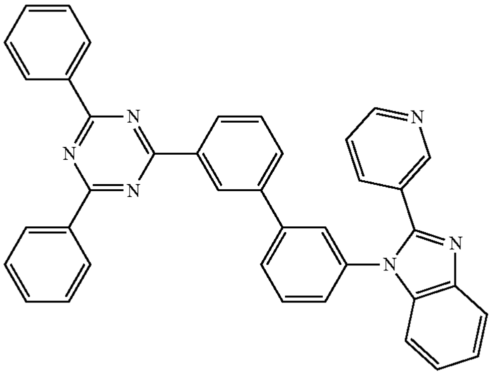
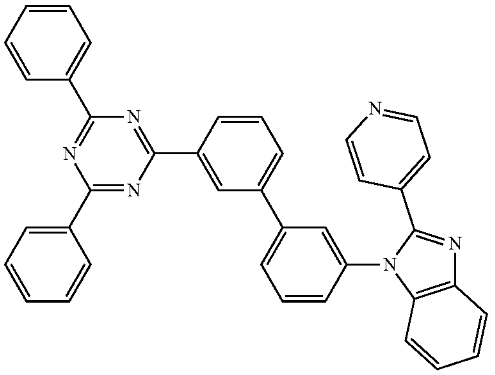
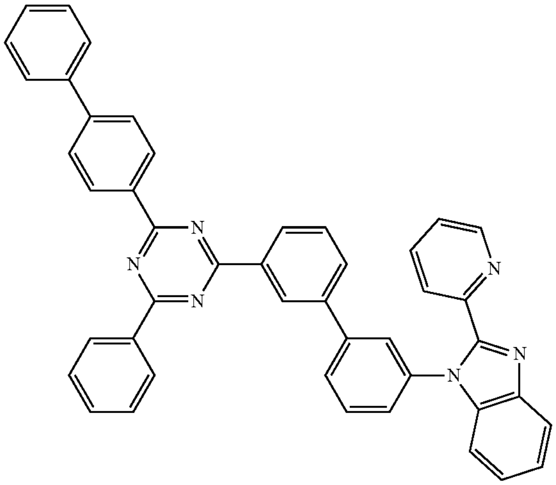
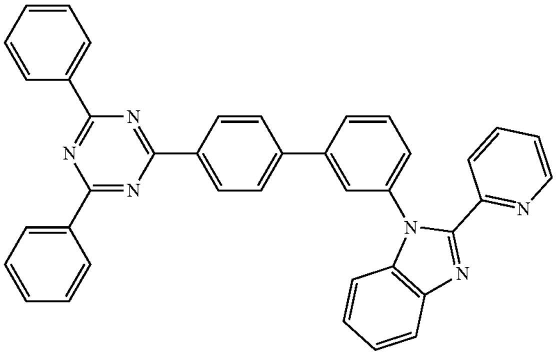
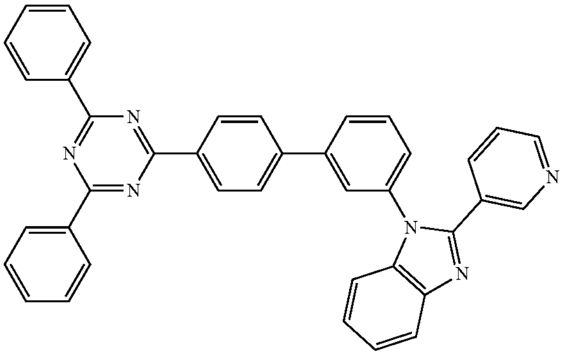
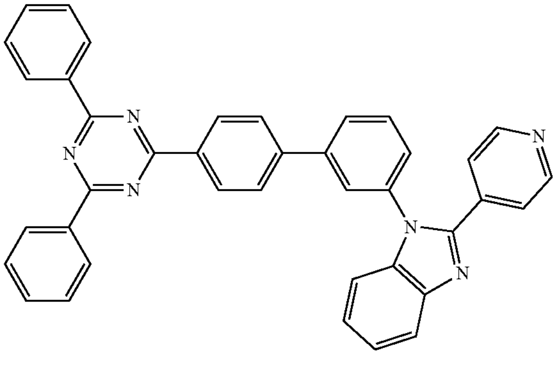

-continued
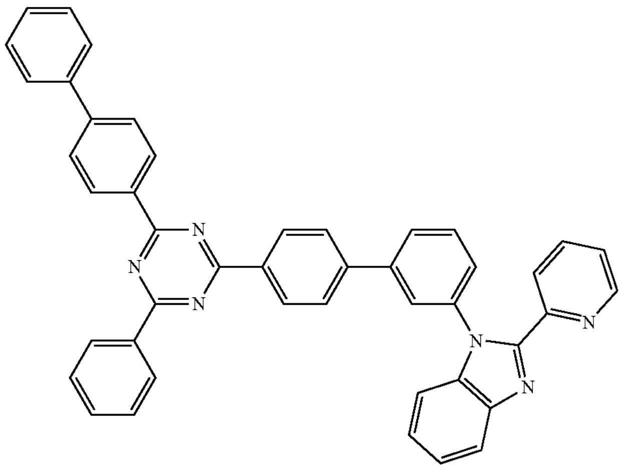
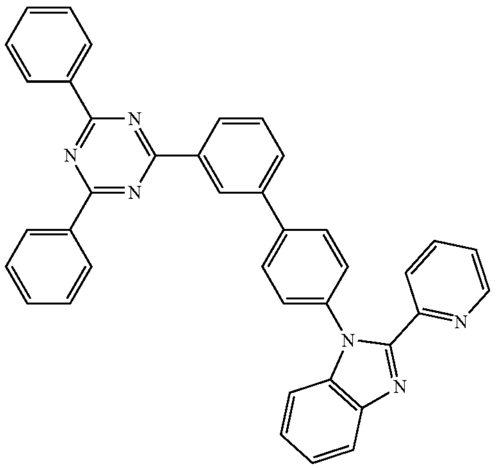
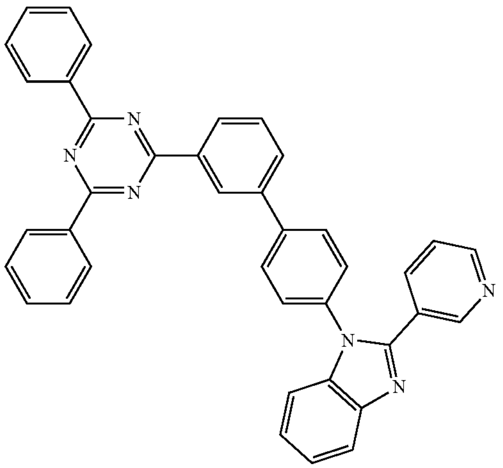
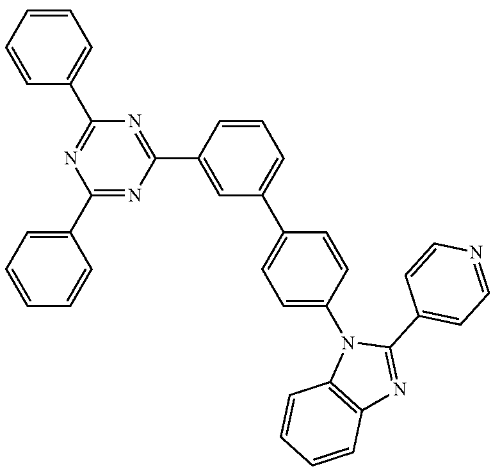
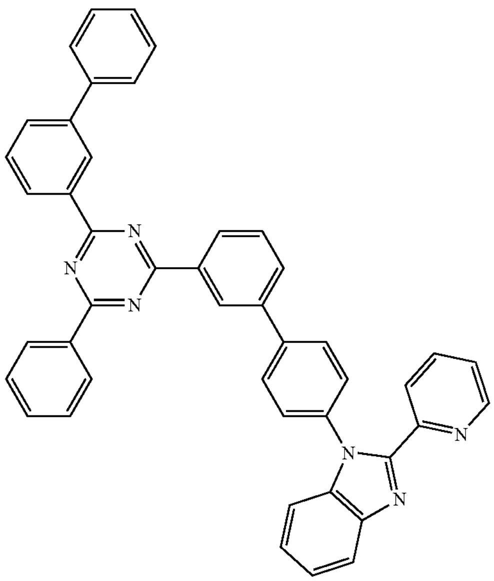

-continued
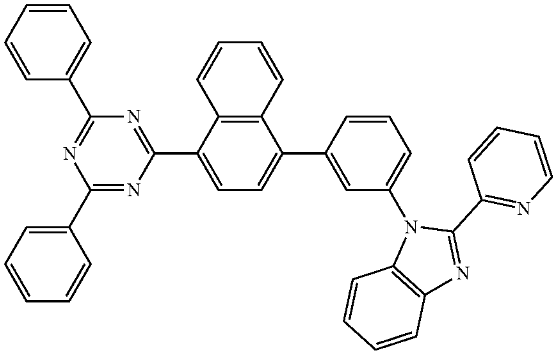
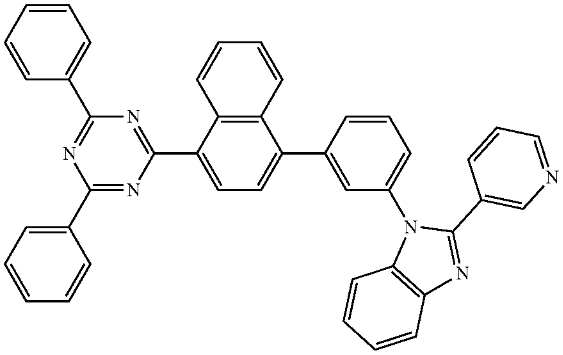
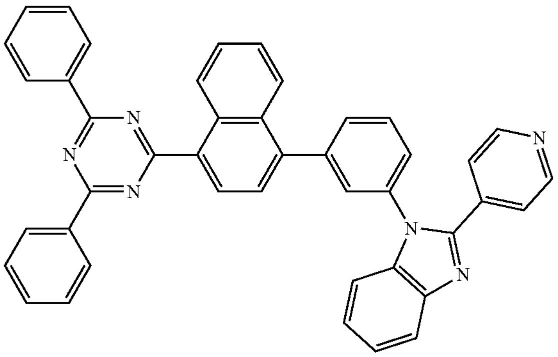
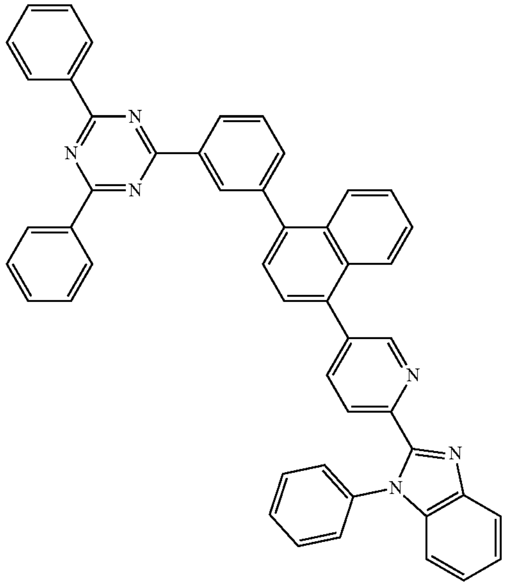
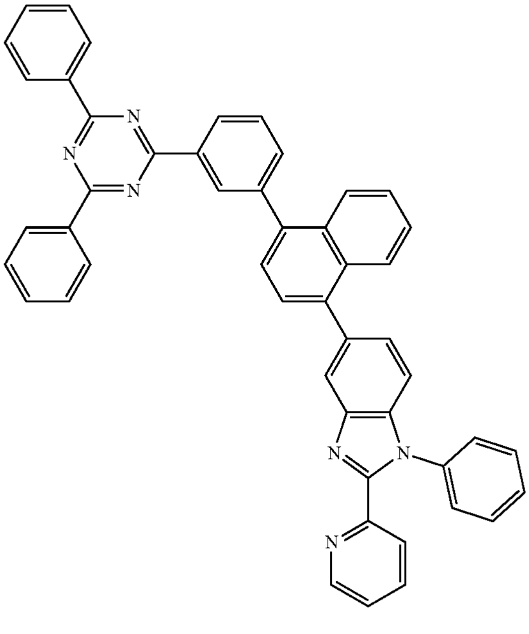
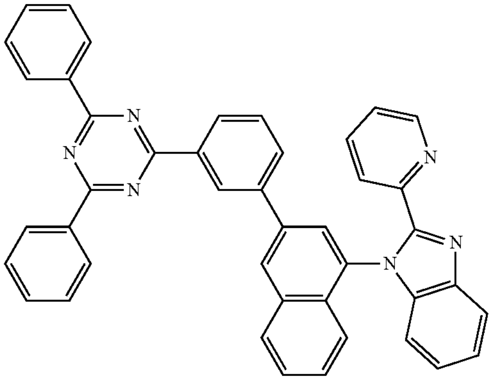

-continued
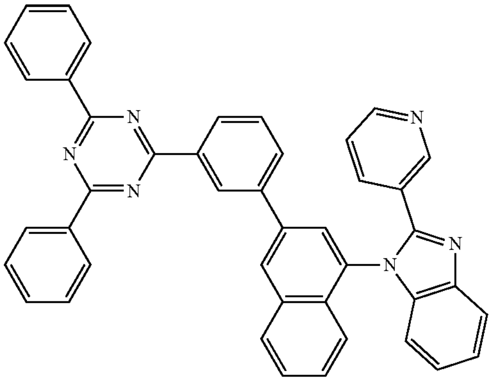
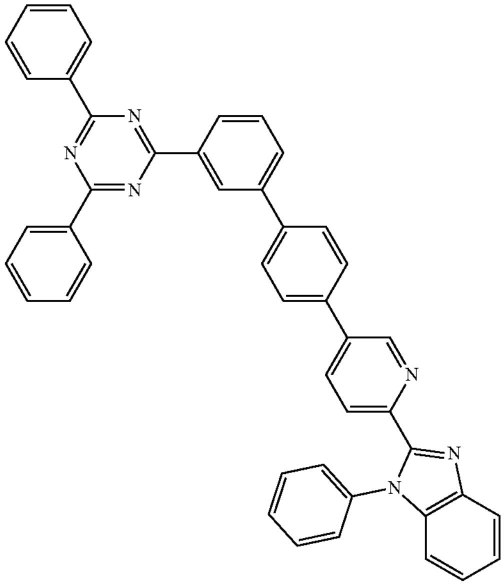
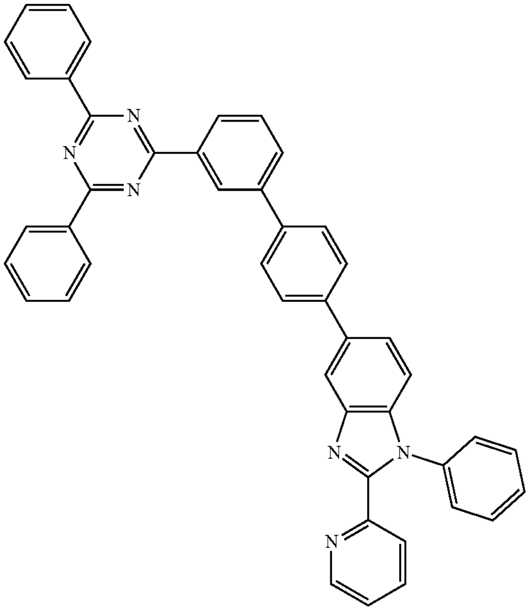
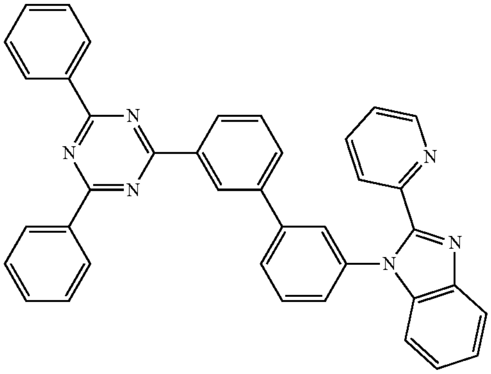

-continued
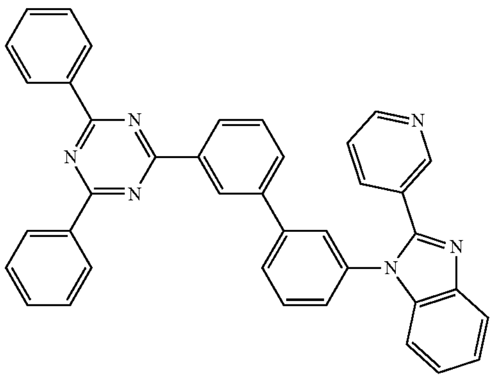
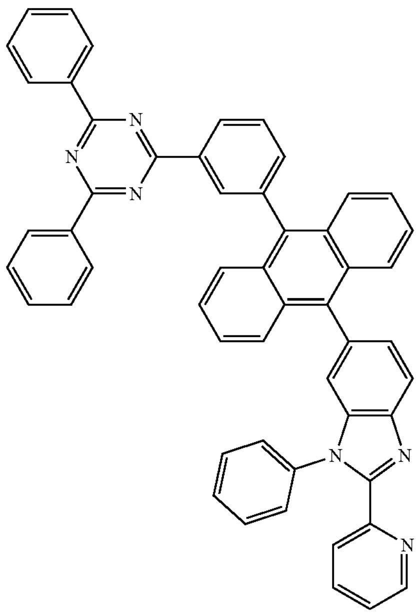
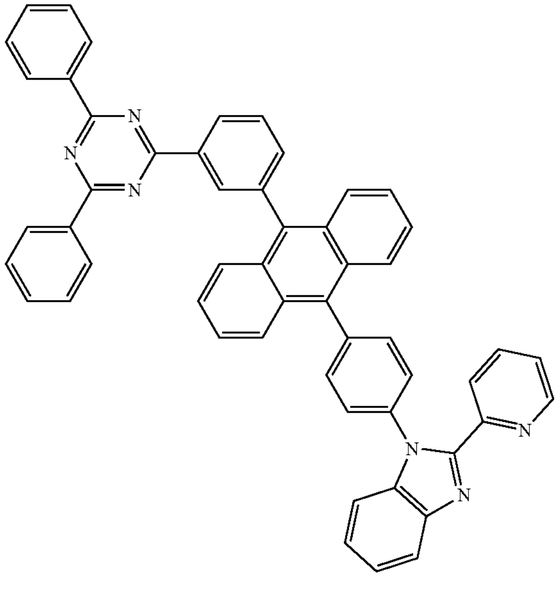

-continued
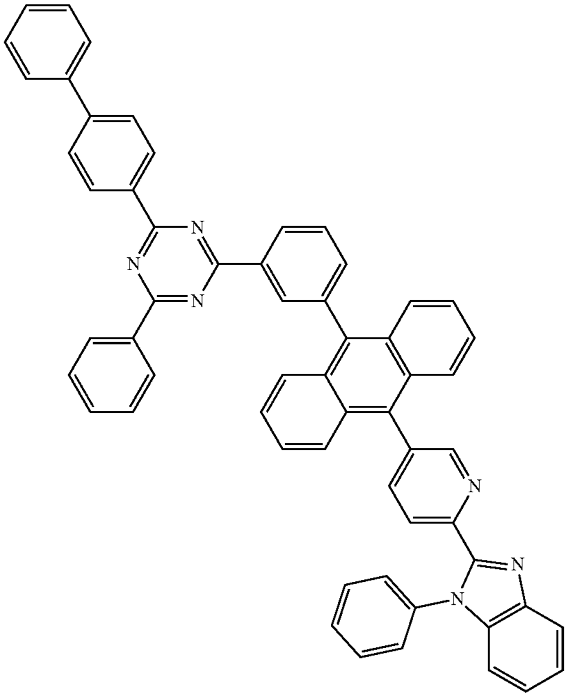
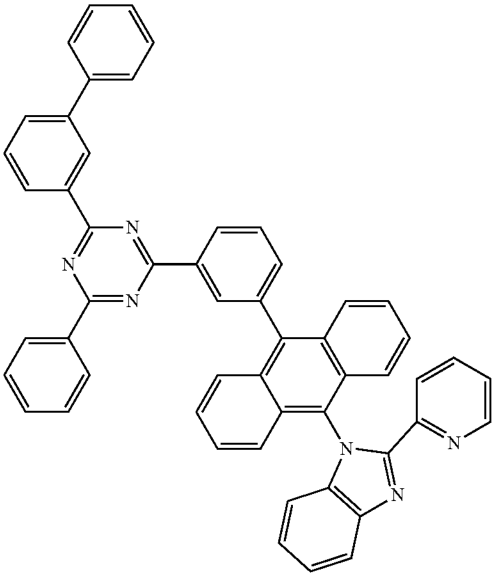
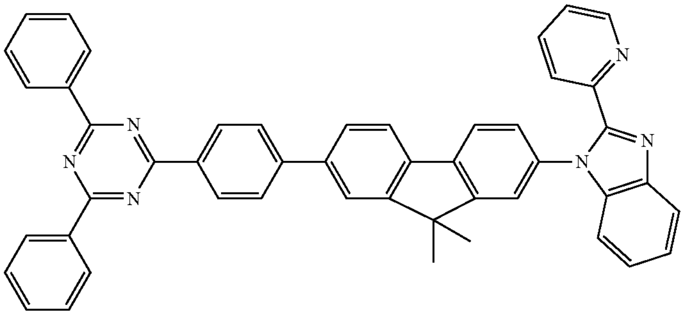
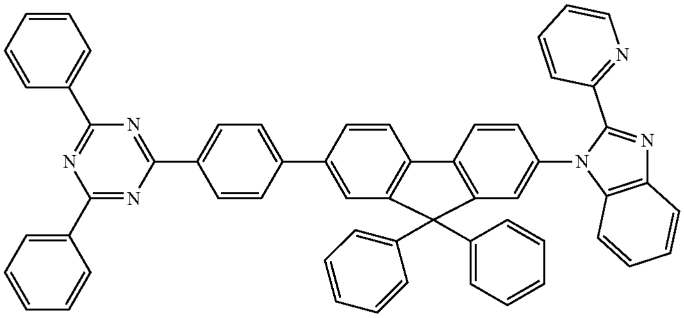
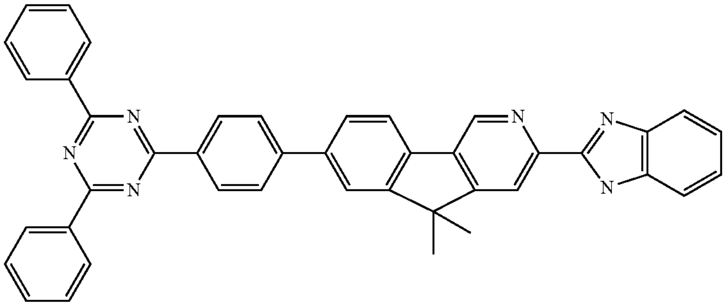

-continued
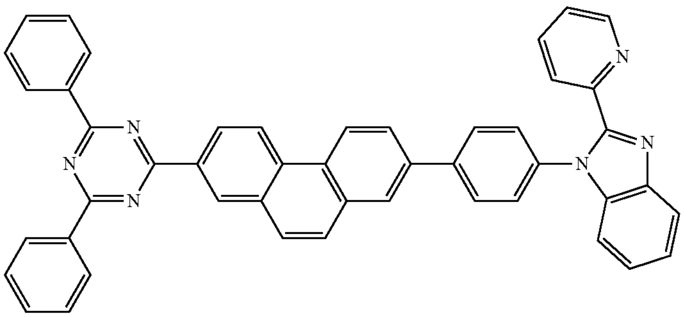
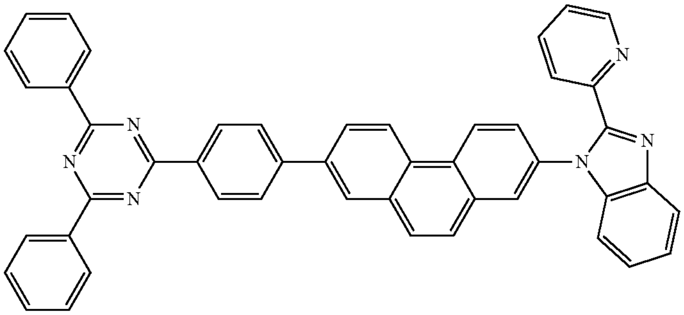
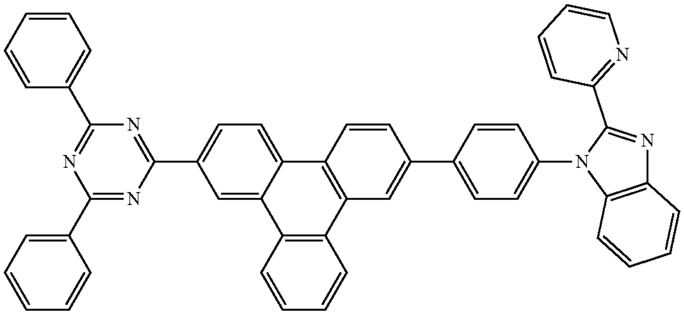
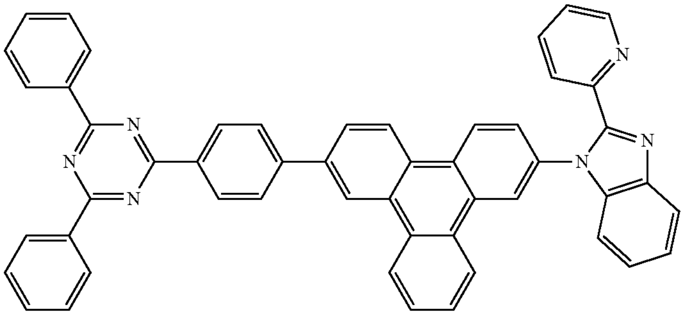
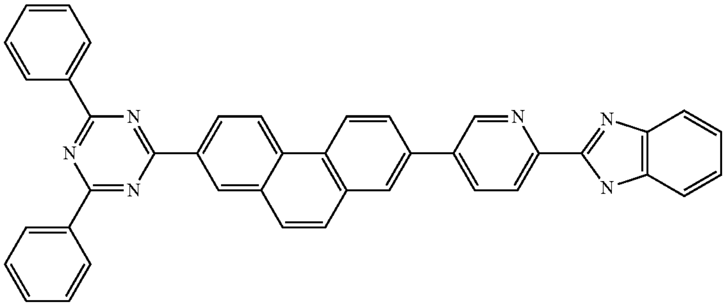

-continued
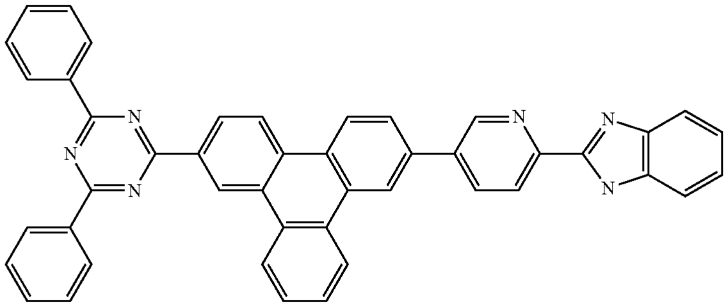
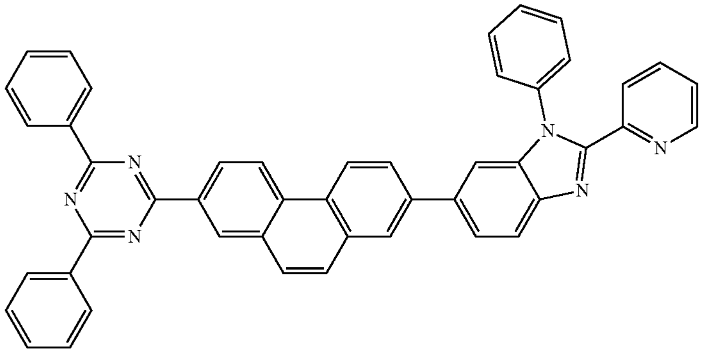
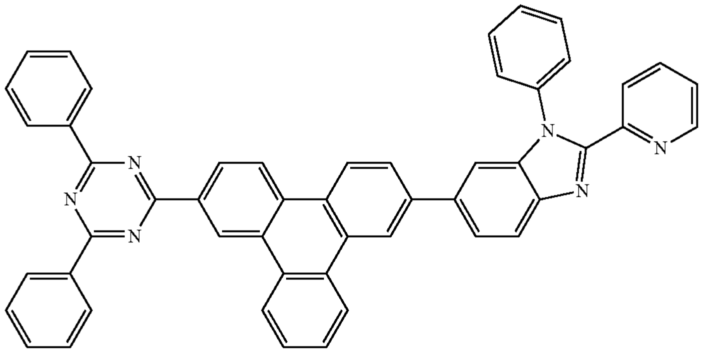
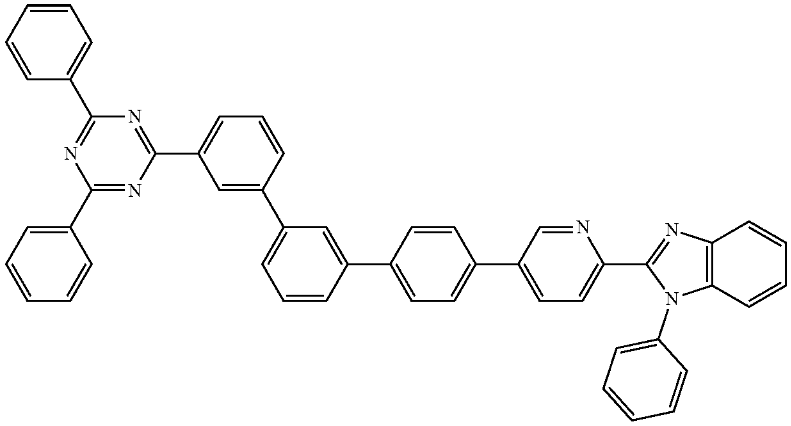

-continued
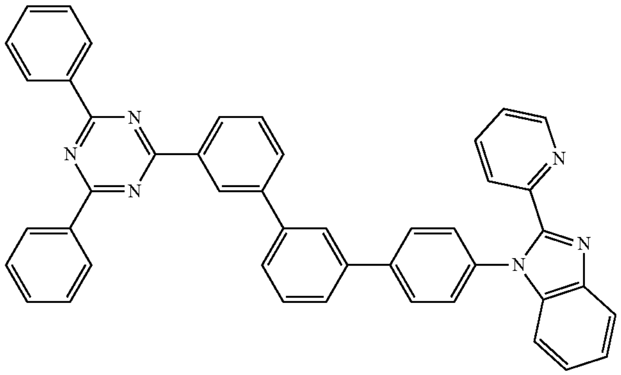
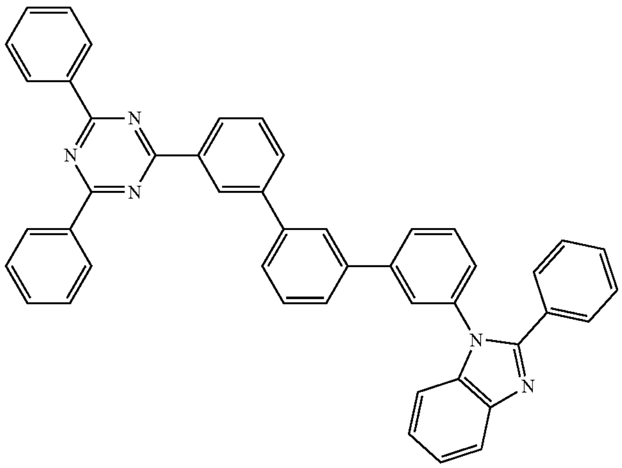
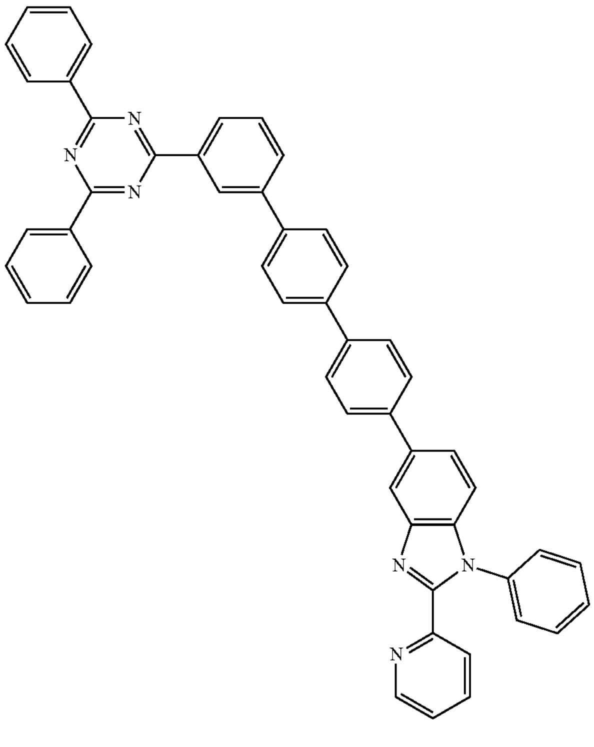

-continued
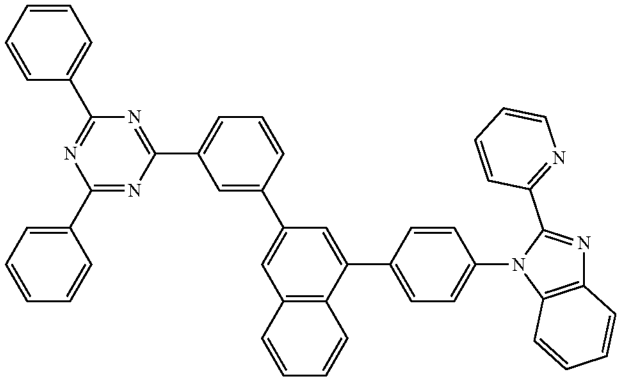
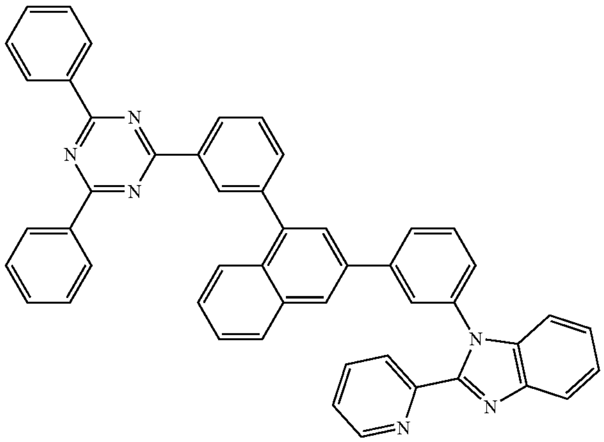
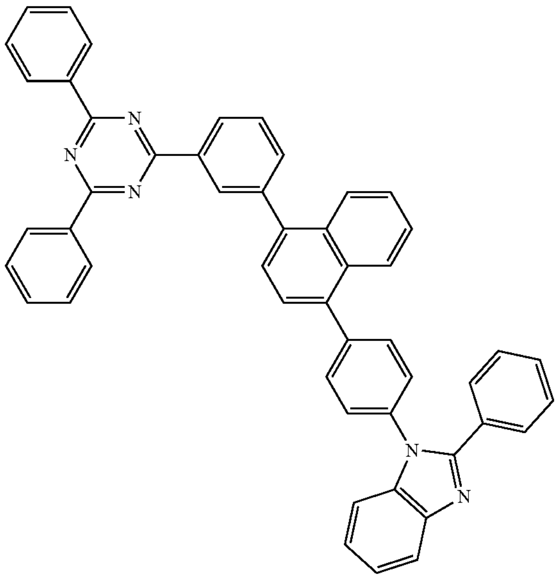
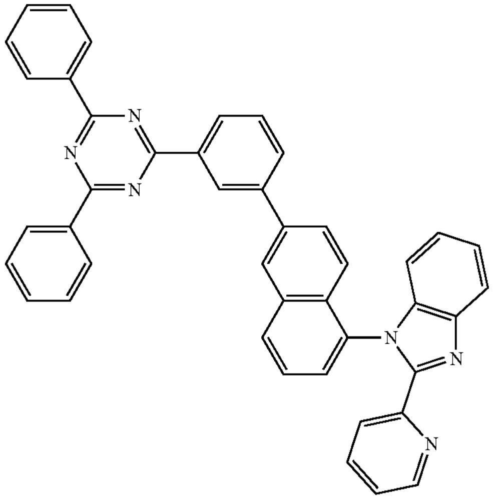

-continued
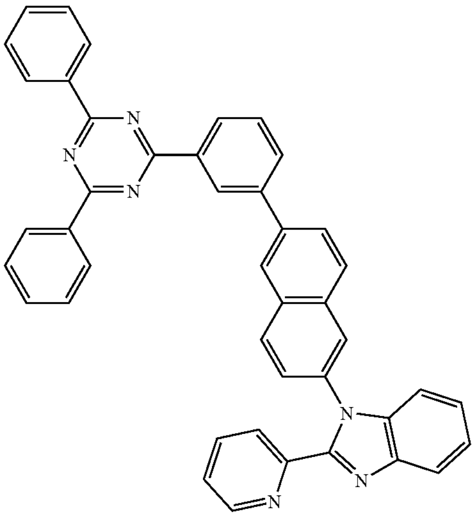
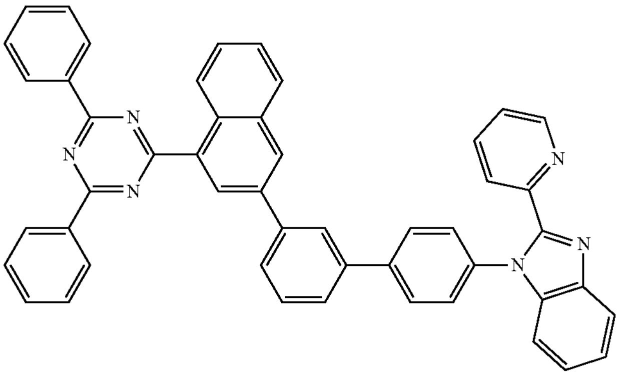
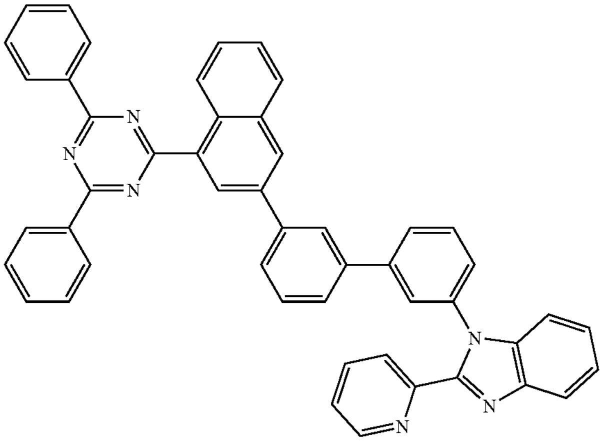
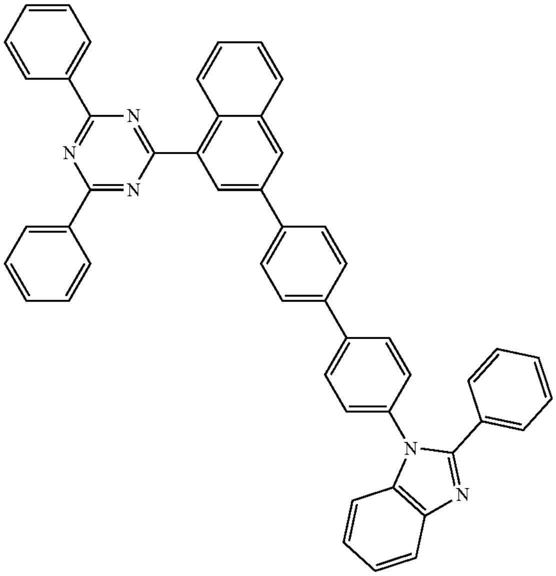

-continued
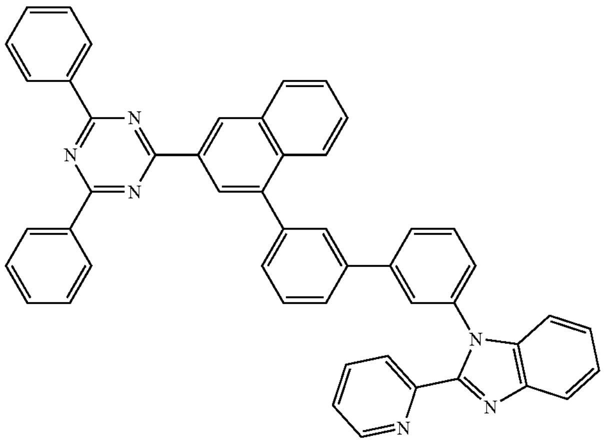
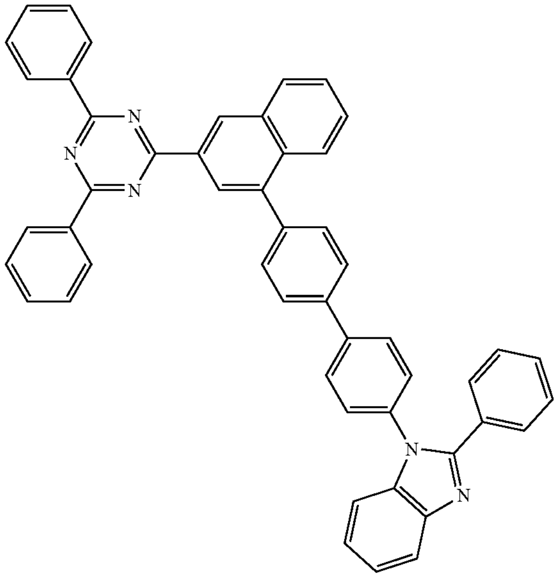
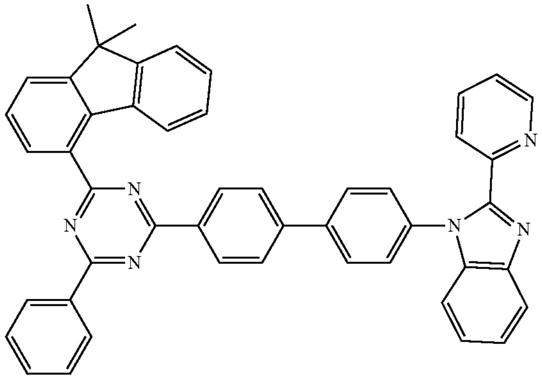
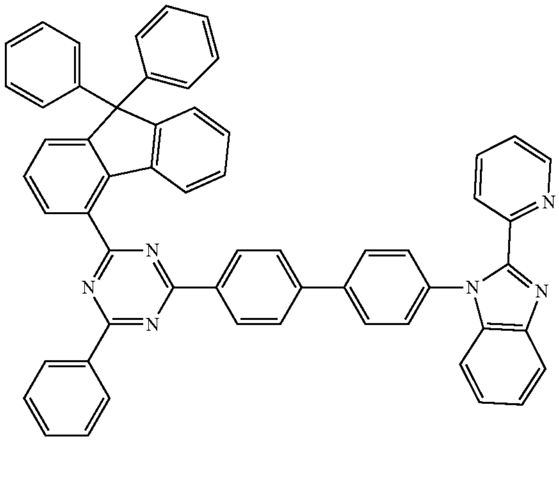
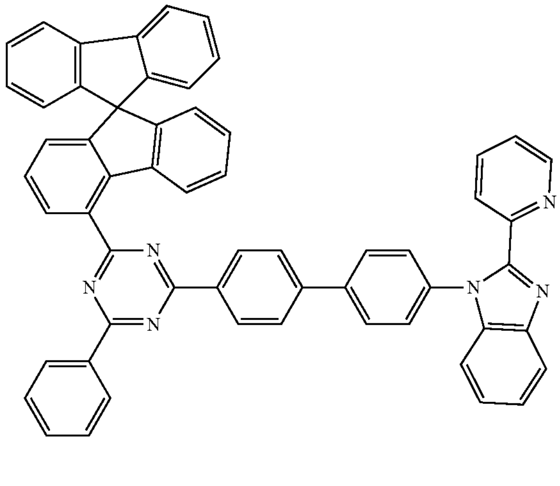

-continued
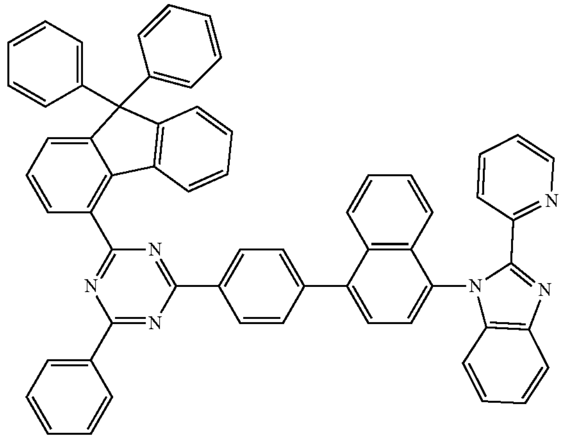
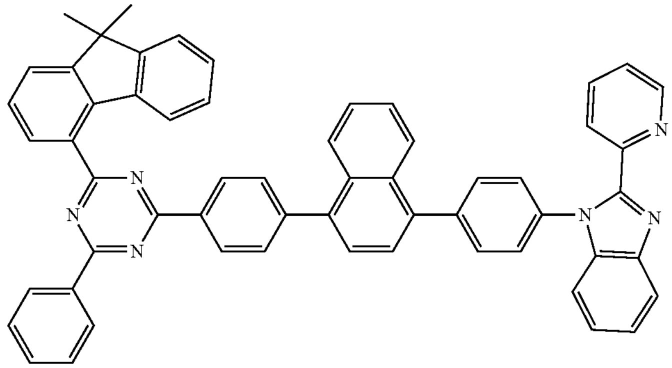
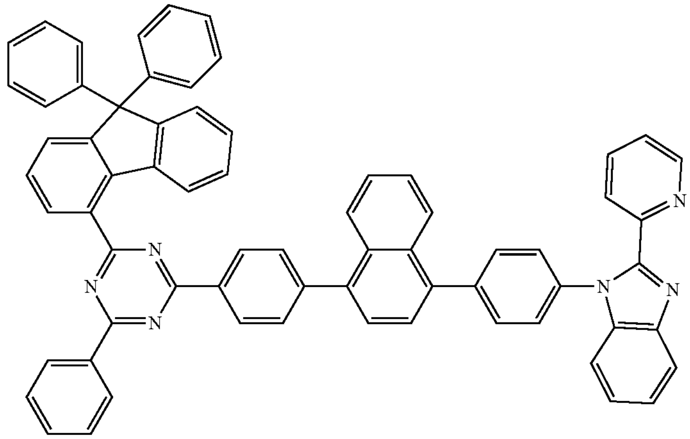
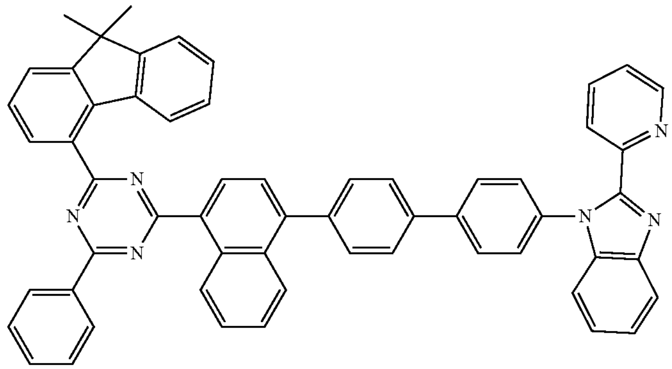

-continued
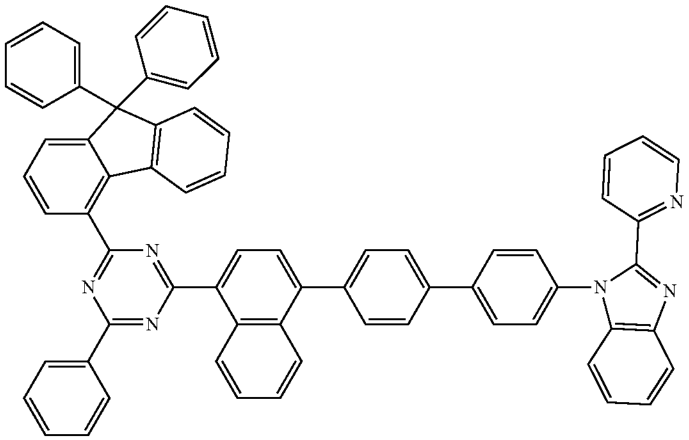
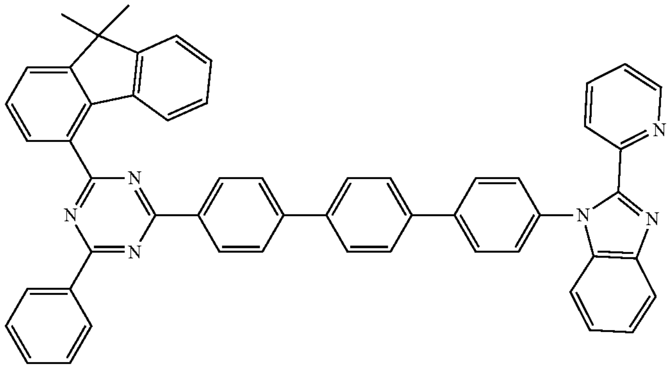
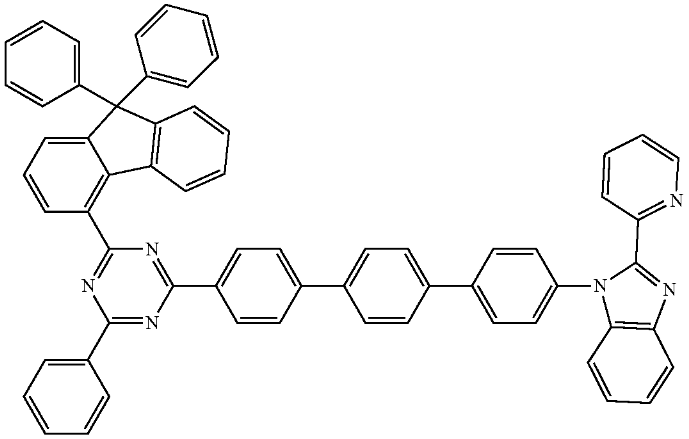
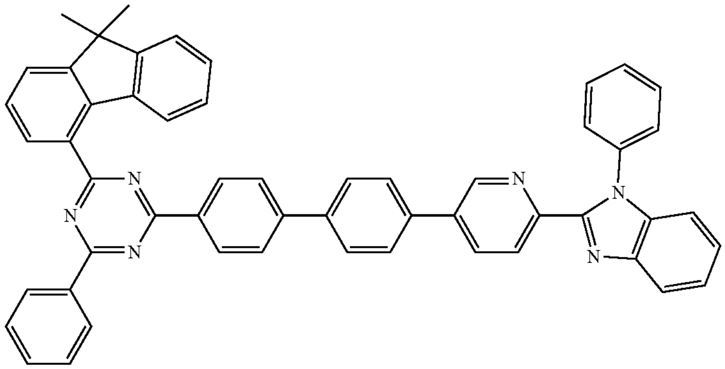

-continued
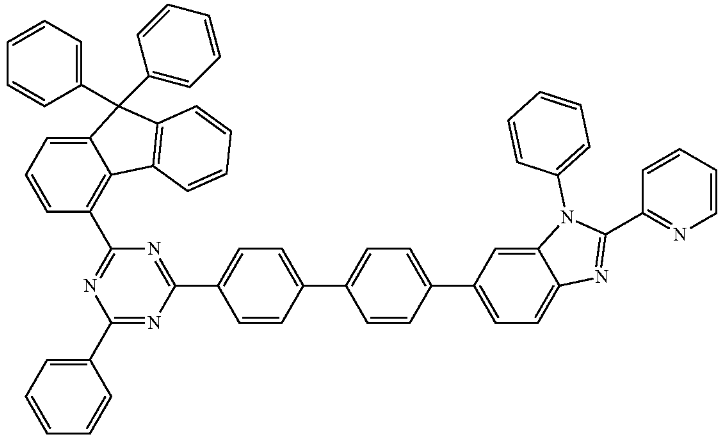
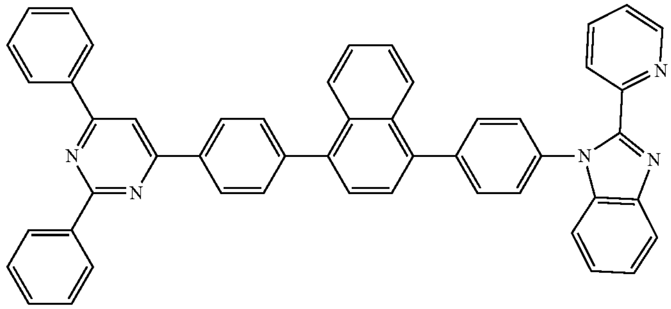
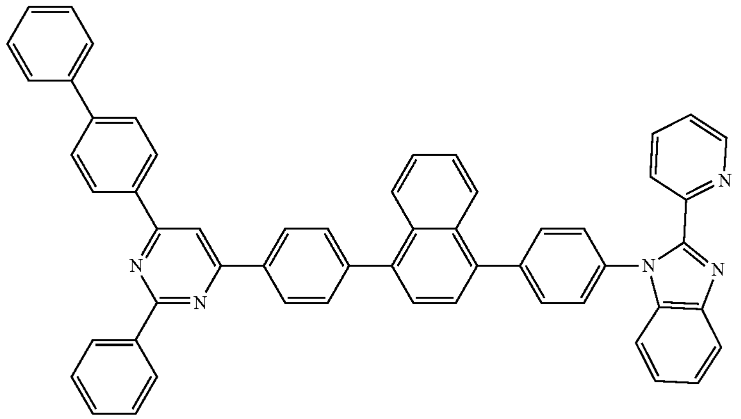
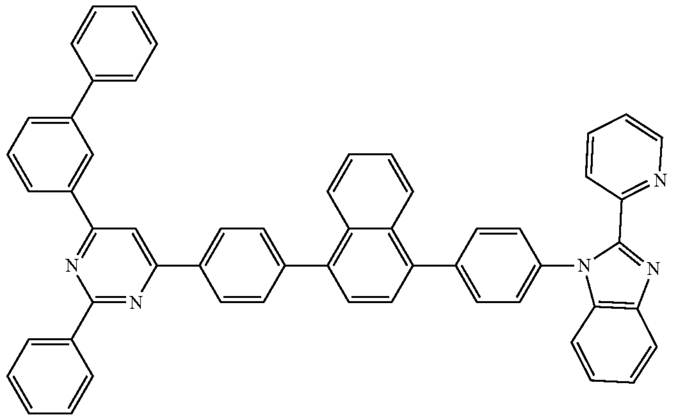

-continued
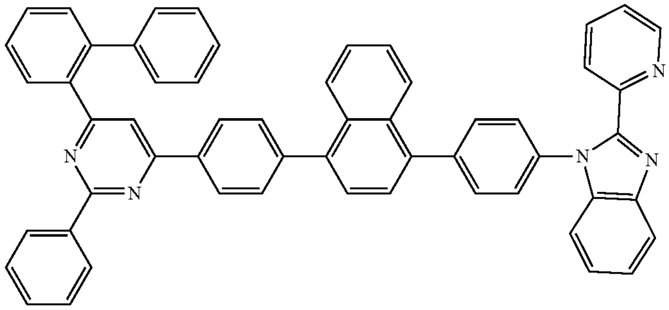
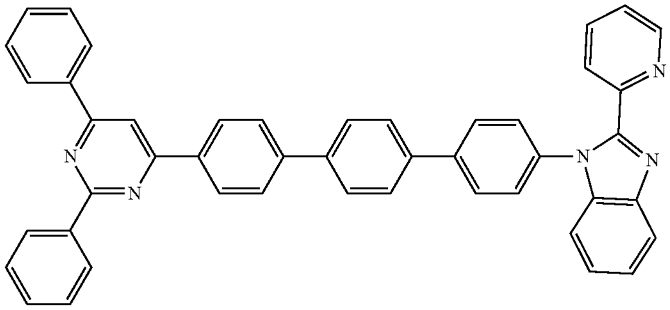
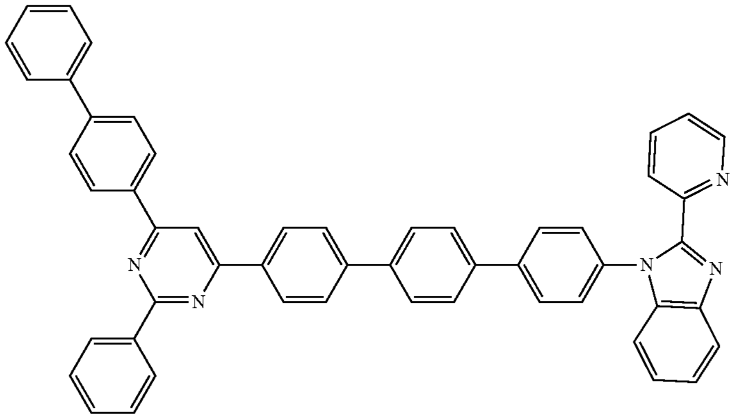
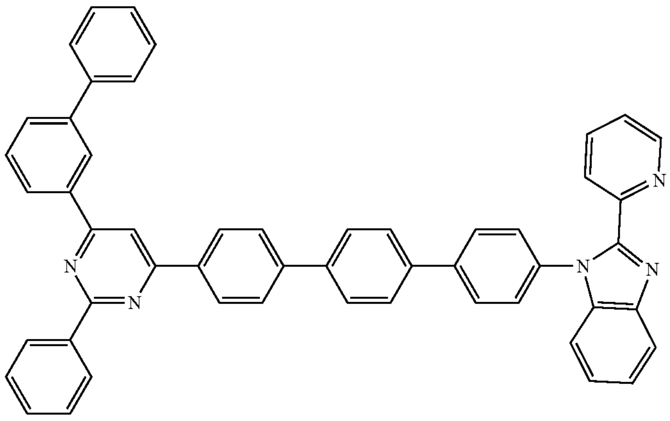

-continued
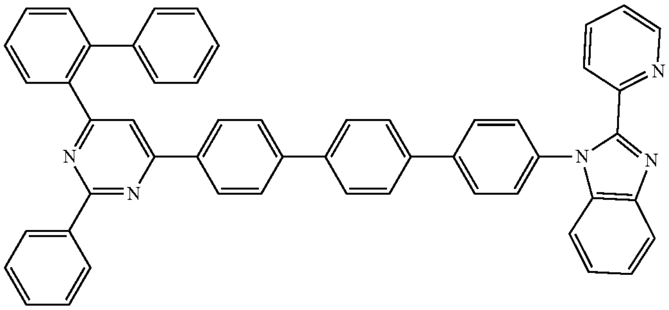
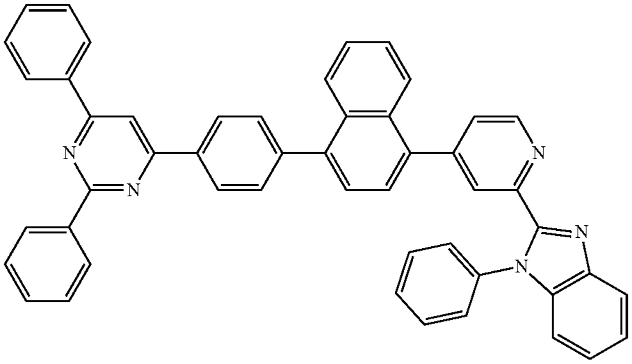
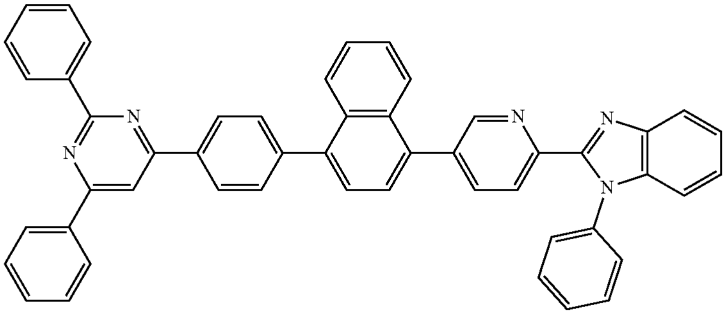
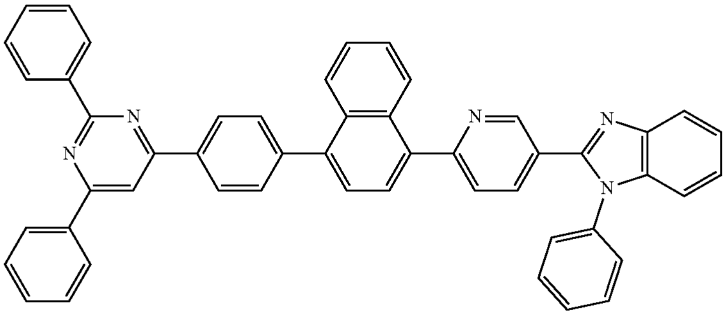
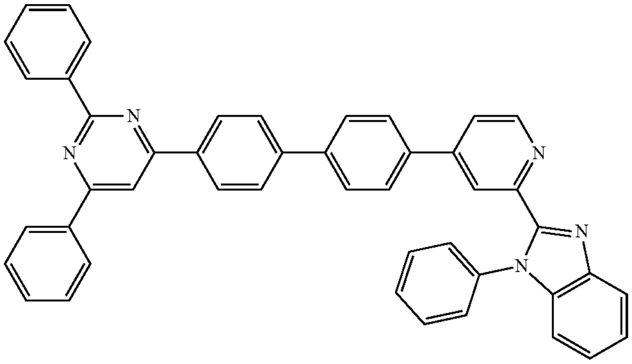

-continued
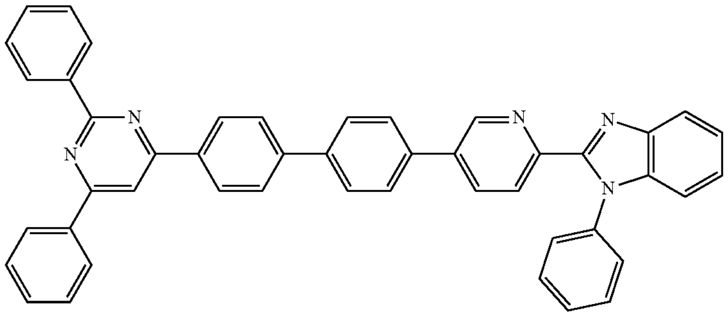
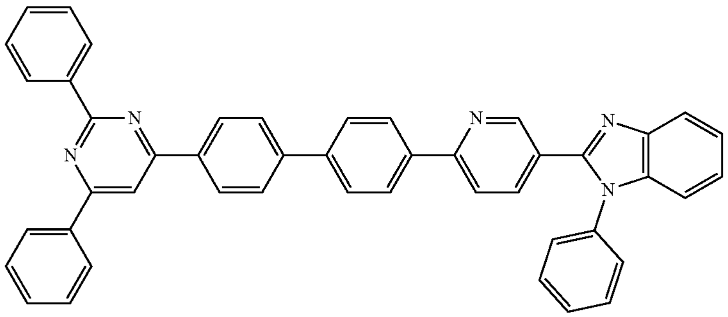
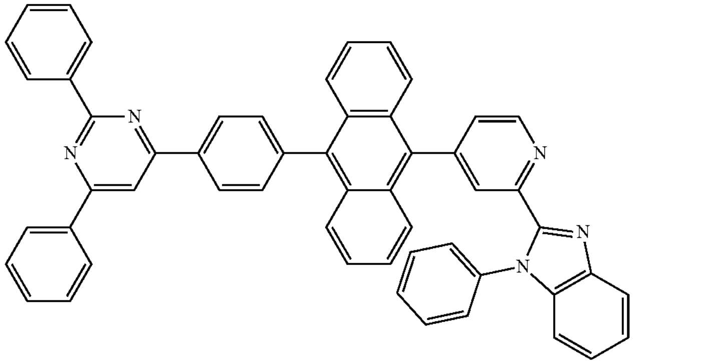
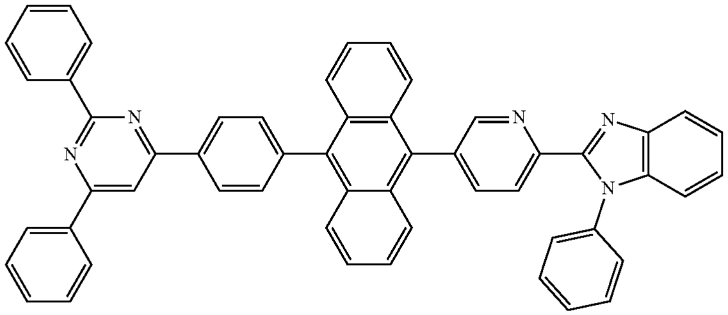
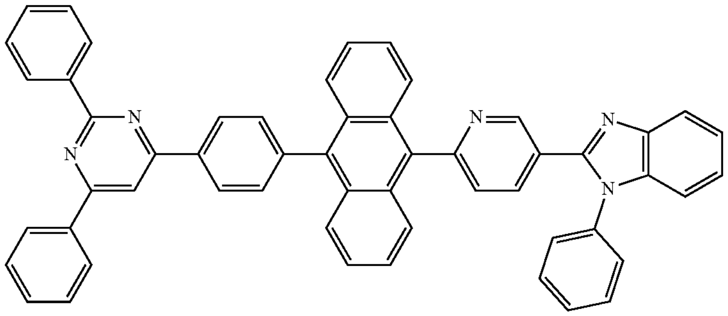

-continued
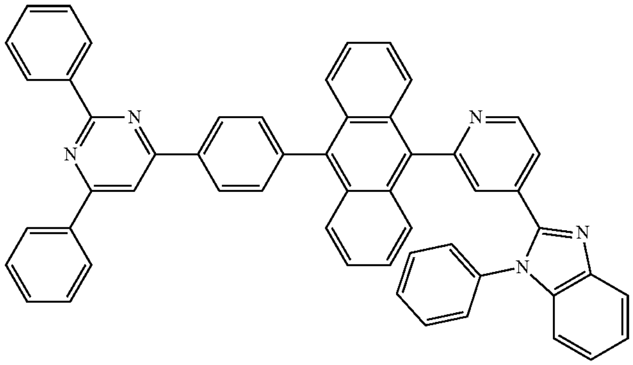
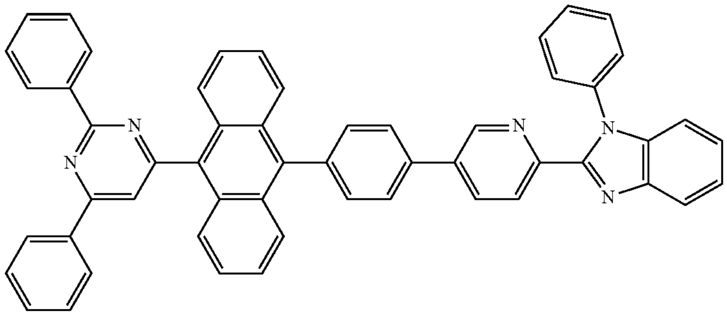
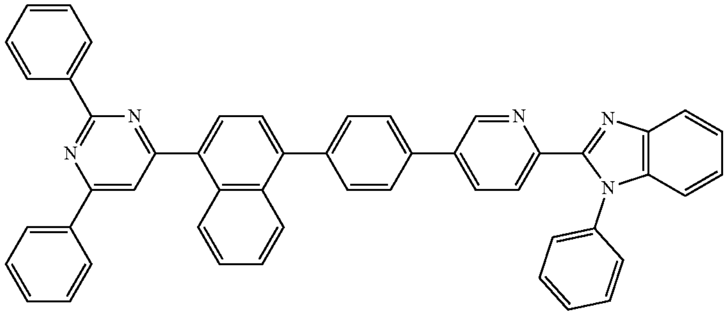
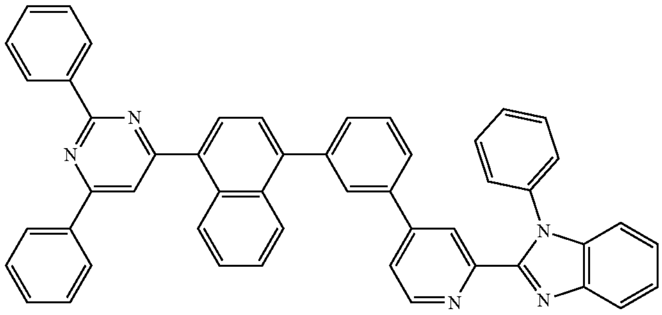

-continued
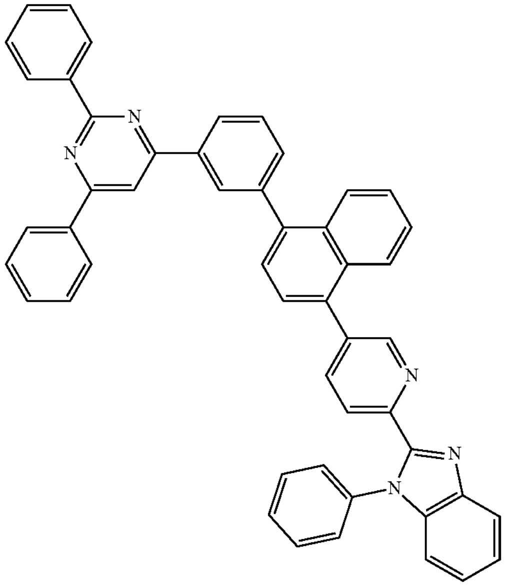
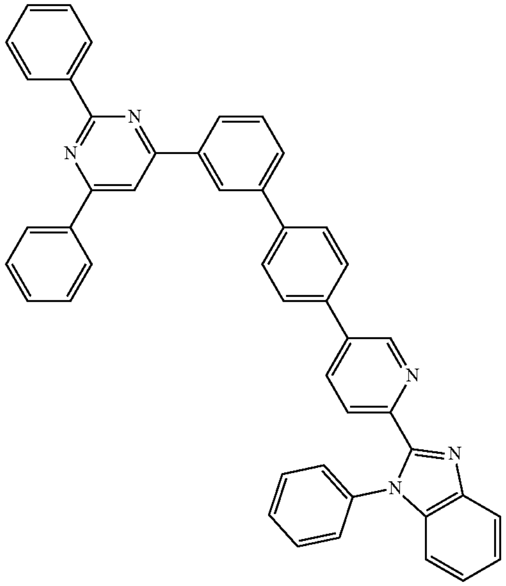
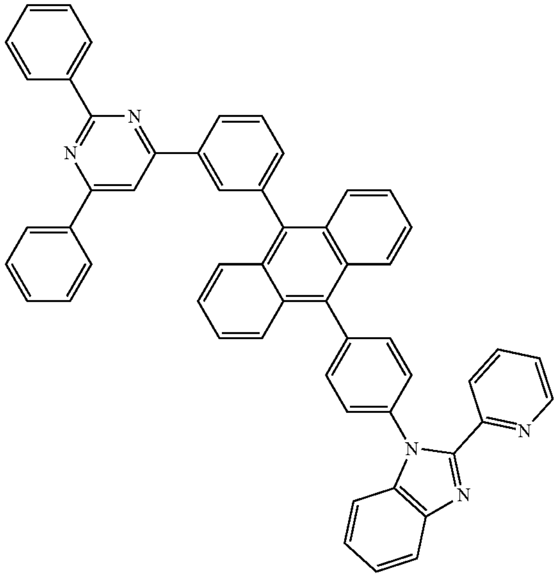
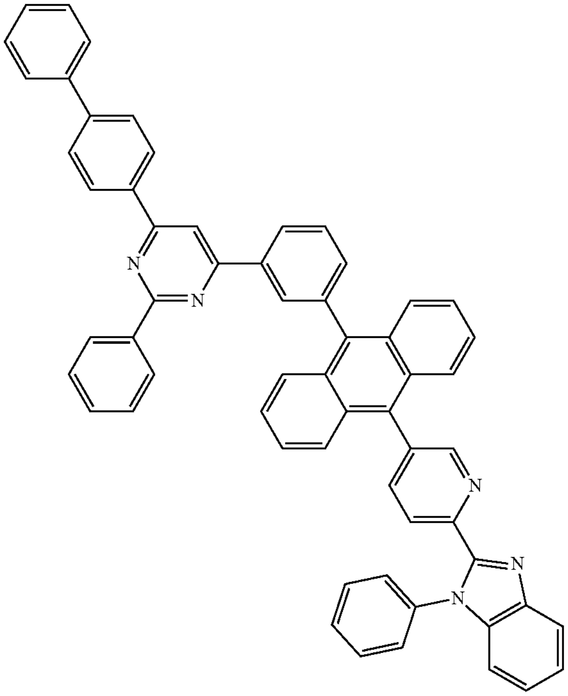
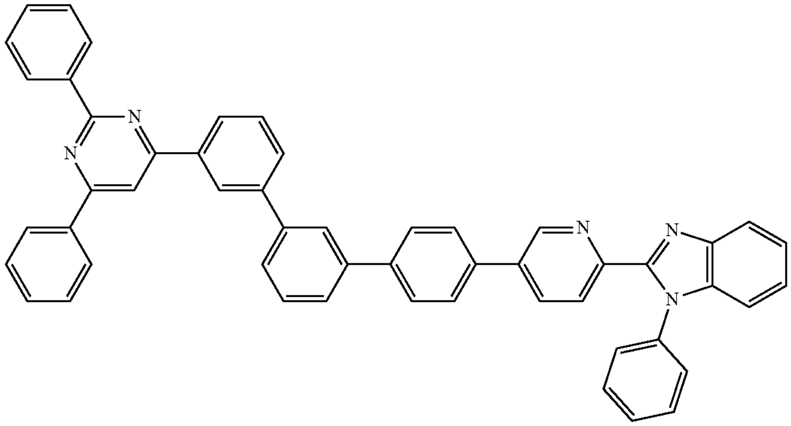

-continued
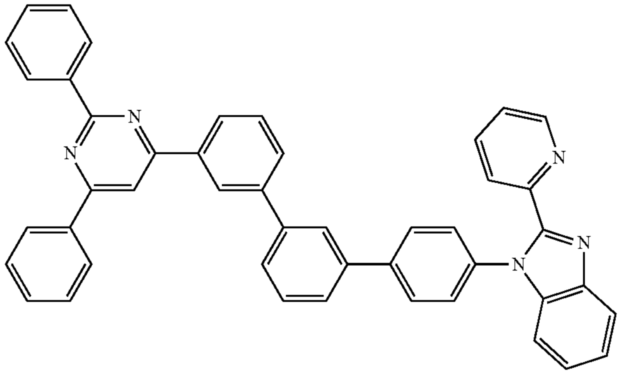
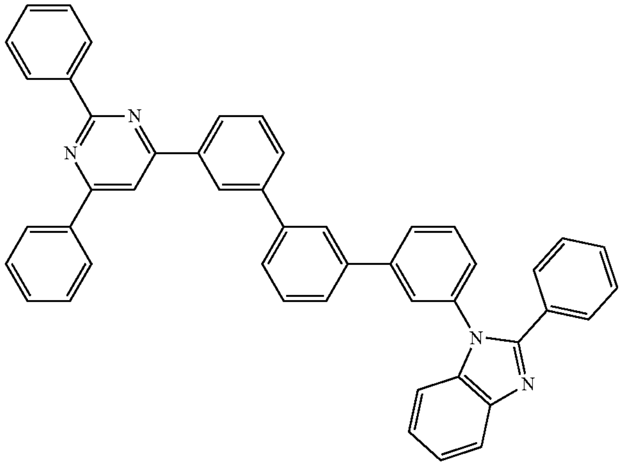
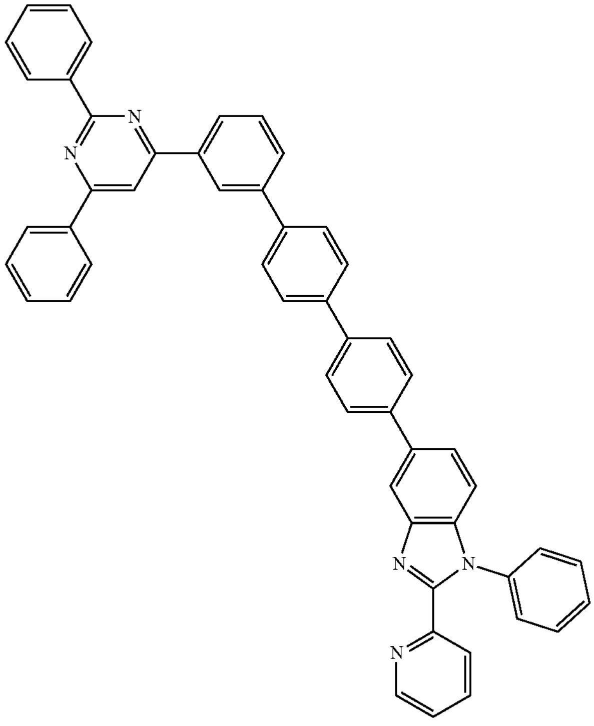

-continued
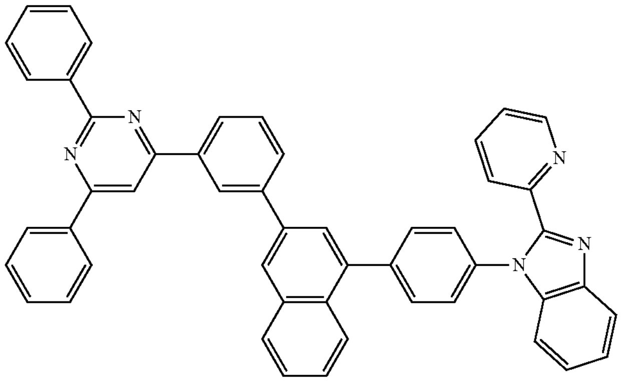
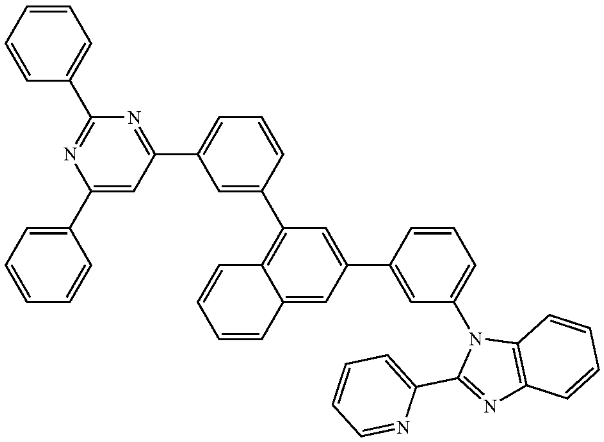
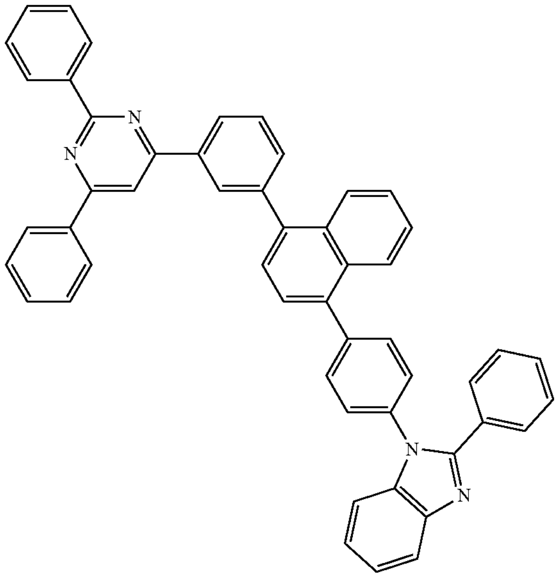

-continued
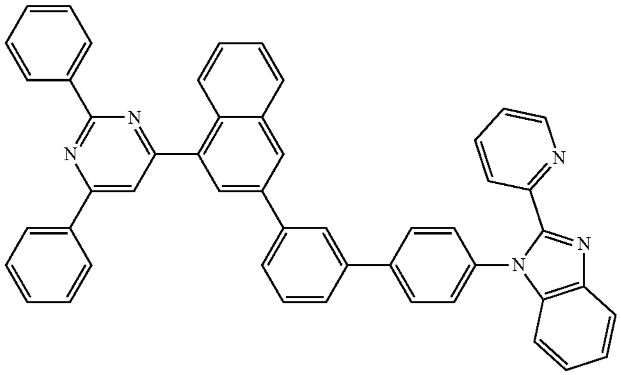
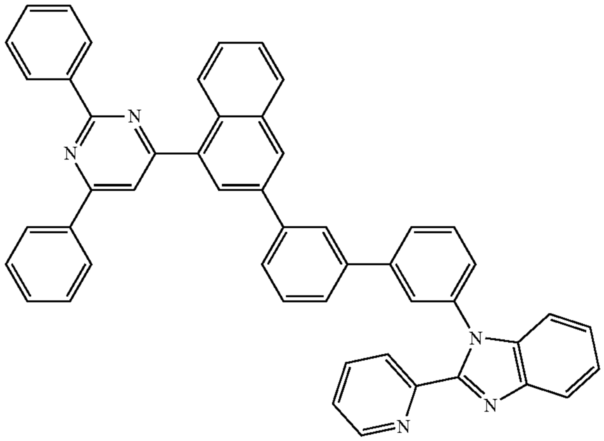
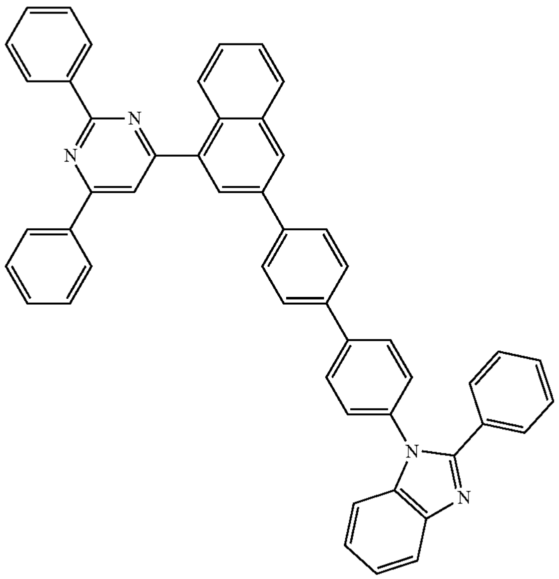

-continued
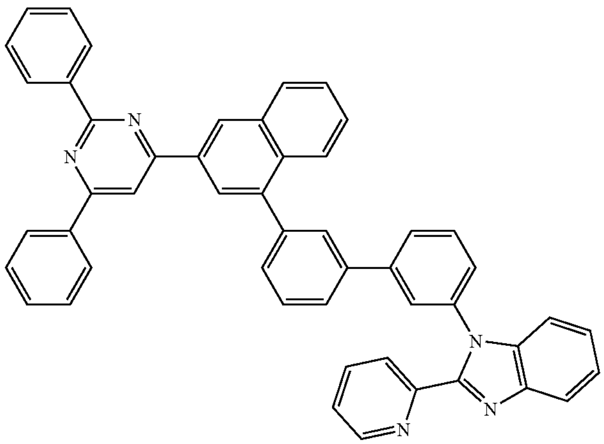
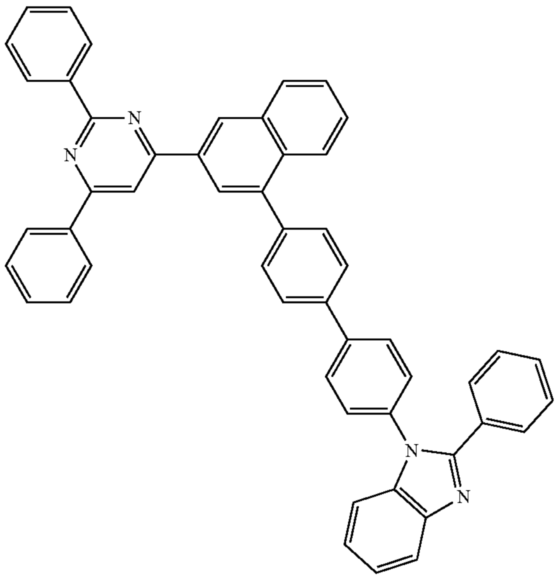
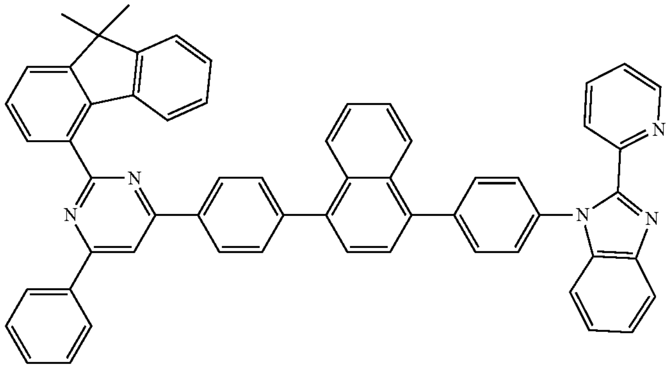

-continued
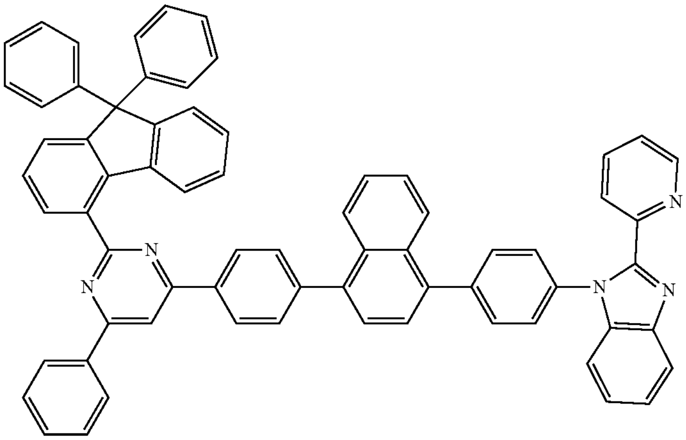
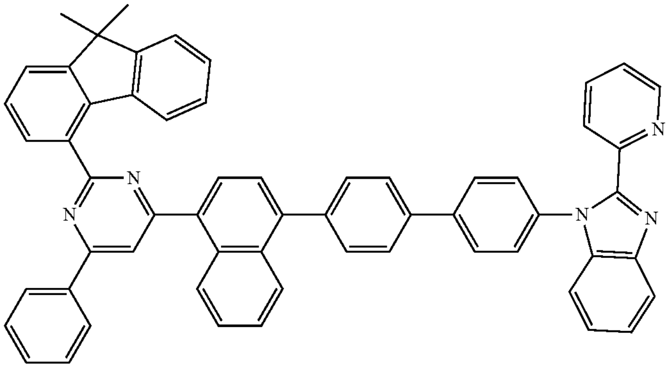
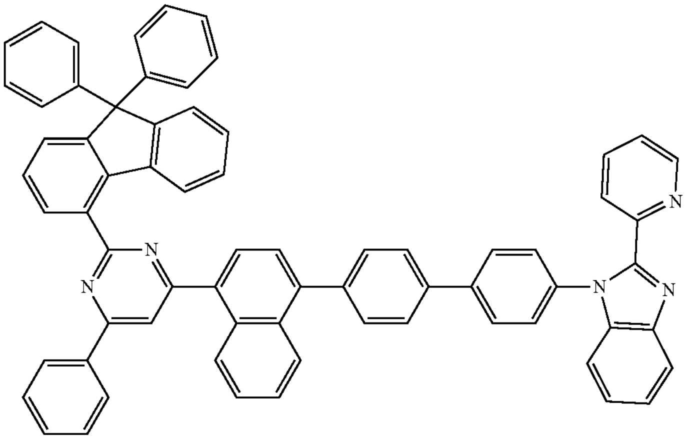
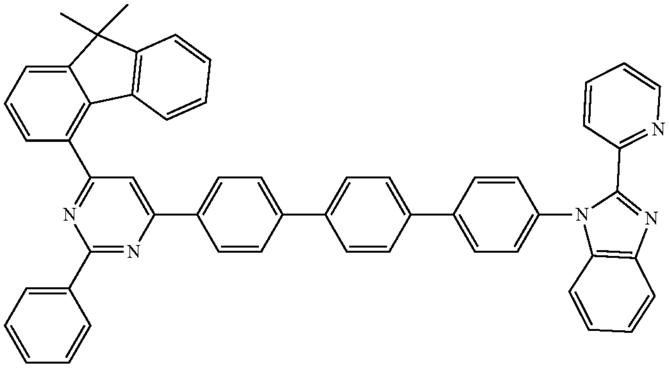

-continued

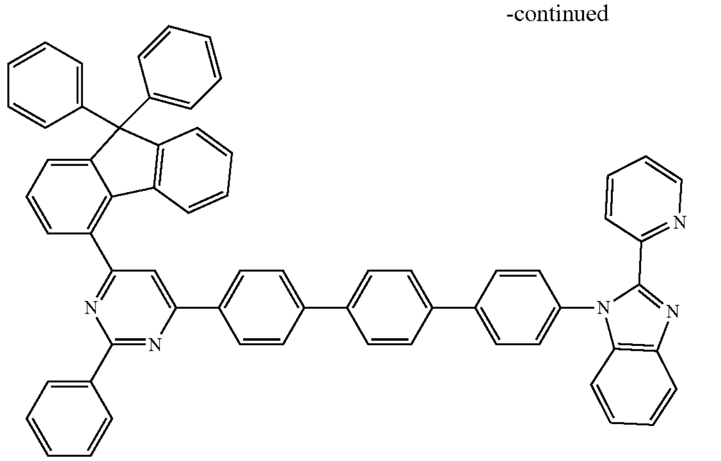

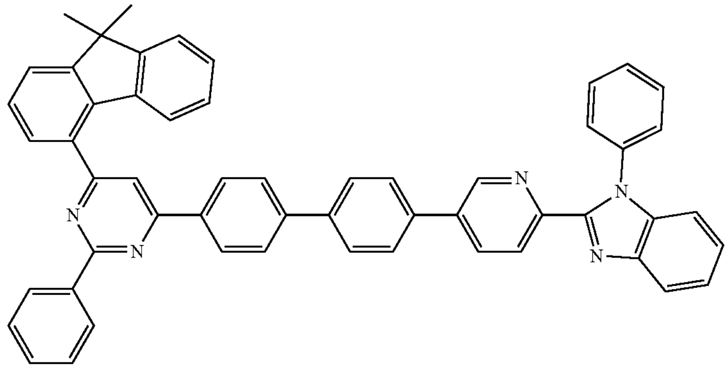

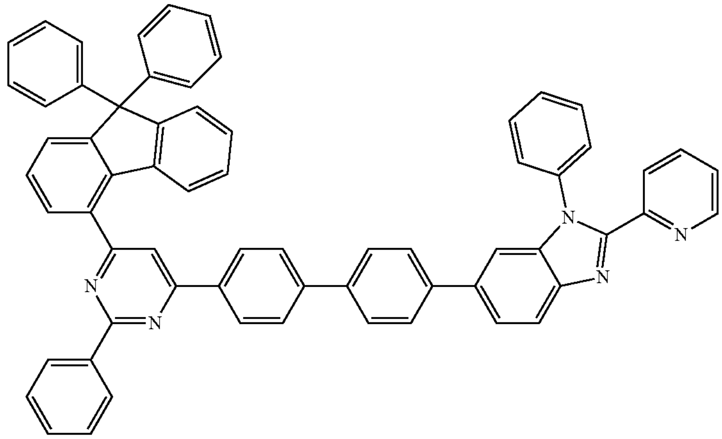

Synthesis of the Compounds of Formula (I)

The compounds of formula (I) can be for example prepared by the following process:

i) Preparation of Intermediate 1

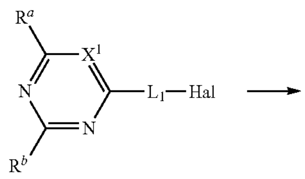

-continued

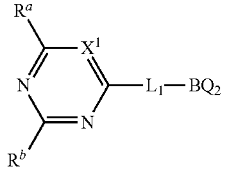

Intermediate 1 wherein

Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered substituted or unsubstituted ring, Hal is a halide, preferably selected from the group consisting of I, F, Cl and Br, or a pseudohalide, preferably selected from the group consisting of mesylate, triflate, tosylate and nonaflate.

Intermediate 1 is generally prepared from the corresponding halides in the presence of a borylation reagent:

Suitable borylation reagents are boronic acids or boronic esters, for example alkyl-, alkenyl-, alkynyl-, and aryl-boronic esters. Preferred borylation reagents have the general formula $Q_2BH$ or $Q_2B—BQ_2$, wherein Q is defined above. For example, Pinacolborane (Hbpin), Bis(pinacolato) diboron ($B_2Pin_2$), and bis(catecholato)diborane ($B_2Cat_2$). Further suitable borylation reagents are dioxaborolanes, for example 2-isopropoxy-4,4,5,5-tetramethyl-1,3,2-dioxaborolane.

The borylation can be carried out in the presence or in the absence of a catalyst.

In the case that the borylation is carried out in the absence of a catalyst, the halide is for example treated with an organolithium reagent followed by borylation with a borylation agent. Suitable borylation agents are mentioned above.

In the case that the borylation is carried out in the presence of a catalyst, preferred catalysts are Pd catalysts. Suitable Pd catalysts are for example Pd(0) complexes with bidentate ligands like dba (dibenzylideneacetone), or Pd(II) salts like $PdCl_2$ or $Pd(OAc)_2$ in combination with bidentate phosphine ligands such as dppf ((diphenylphosphino)ferrocene), dppp ((diphenylphosphino)propane), BINAP (2,2'-Bis(diphenylphosphino)-1,1'-binaphthyl), Xantphos (4,5-Bis(diphenylphosphino)-9,9-dimethylxanthene), DPEphos (Bis[(2-diphenylphosphino)phenyl] ether) or Josiphos, or in combination with monodentate phosphine-ligands like triphenylphosphine, tri-ortho-tolyl phosphine, tri-tert-butylphosphine, tricyclohexylphosphine, 2-Dicyclohexylphosphino-2',6'-dimethoxybiphenyl (SPhos), 2-Dicyclohexylphosphino-2',4,6'-triisopropylbiphenyl (XPhos), or N-heterocyclic carbenes such as 1,3-Bis(2,6-diisopropylphenyl)imidazol-2-ylidene (IPr), 1,3-Dimesitylimidazol-2-ylidene (Imes).

Josiphos:

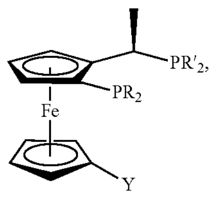

wherein R and R' are generally substituted or unsubstituted phenyl.

The residues, groups and indices $R^a$, $R^b$, $X_1$ and $L_1$ are defined above.

ii) Preparation of the Compounds of Formula (I)

a) Wherein m is 1 and n is 0

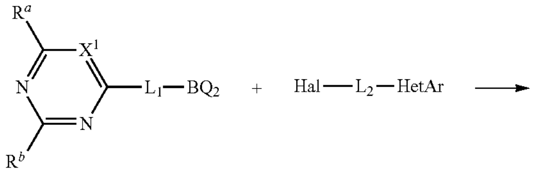

Intermediate 1

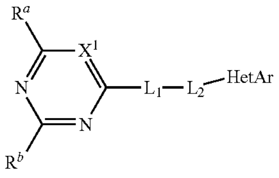

(I)

b) Wherein m is 0 and n is 1

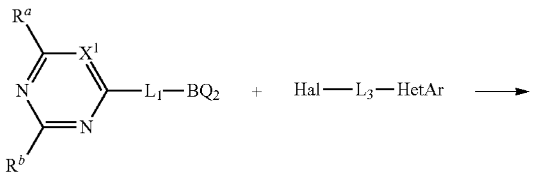

Intermediate 1

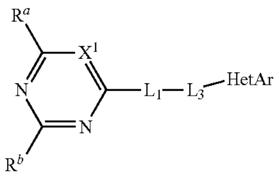

(I)

c) Wherein m is 1, 2 or 3 and n is 1, shown for m=1 as an example ci)

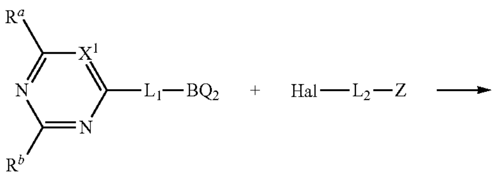

Intermediate 1

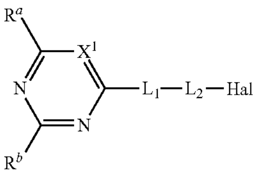

Intermediate 2

-continued cii)

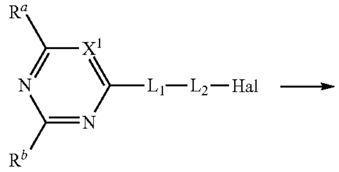

Intermediate 2

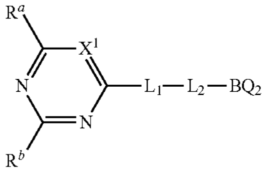

Intermediate 3 ciii)

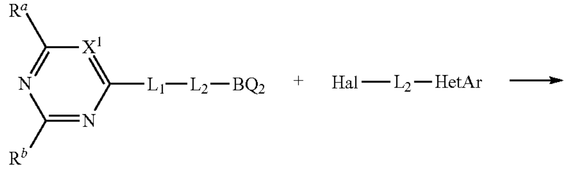

Intermediate 3

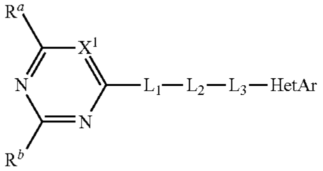

(I)

Wherein Z represents —$BQ_2$, wherein Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered substituted or unsubstituted ring, or —MgX, wherein X is halide, or —Li, preferably —$BQ_2$, wherein Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered substituted or unsubstituted ring, more preferably —$BQ_2$, wherein two alkyl groups Q or two alkoxy groups Q together may form a five or six membered substituted or unsubstituted ring, Hal is a halide, preferably selected from the group consisting of I, F, Cl and Br, or a pseudohalide, preferably selected from the group consisting of mesylate, triflate, tosylate and nonaflate.

The residues, groups and indices $R^a$, $R^b$, $X_1$, $L_1$, $L_2$, $L_3$ and HetAr are defined above.

The compounds Hal-$L_2$-HetAr, wherein HetAr is a group of formula (II), Hal-$L_3$-HetAr, wherein HerAr is a group of formula (IV) and Hal-HetAr, wherein HetAr is a group of formula (III) are for example prepared as follows:

x)

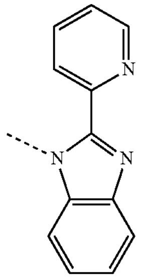

as HetAr and n=0:

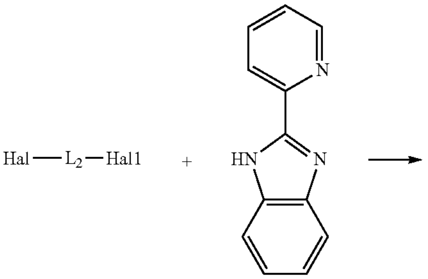

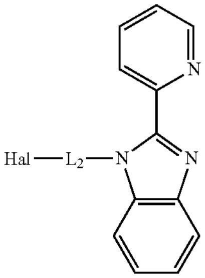

y)

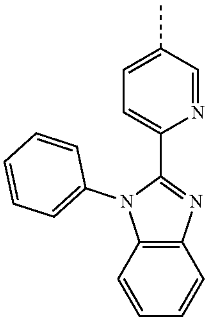

as -$L_3$-HetAr, i.e. n=1 and HetAr is a group of formula (IV):

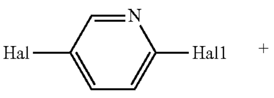

-continued

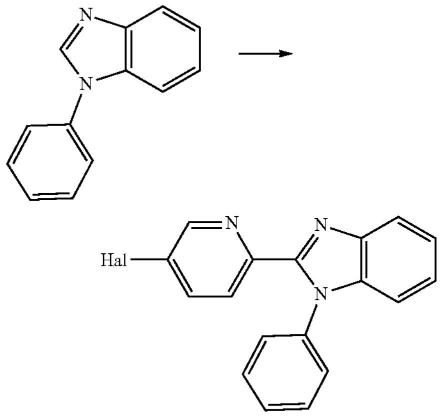

z)

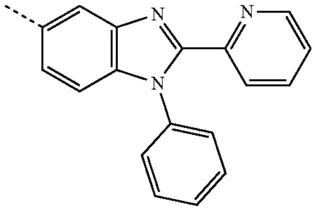

as HetAr, i.e. HetAr is a group of formula (III):

zi)

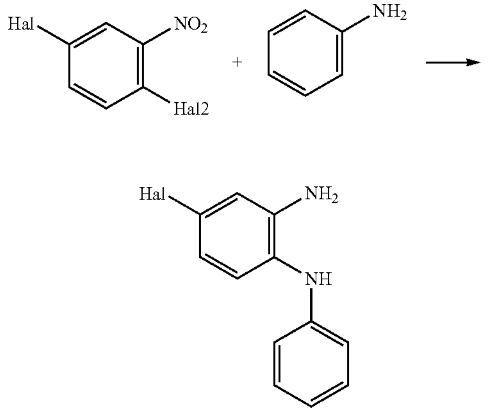

zii)

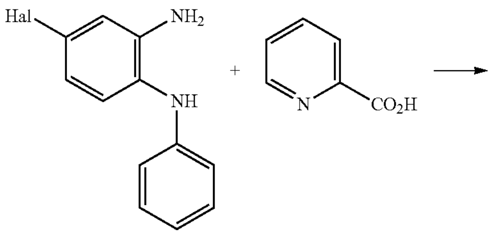

-continued

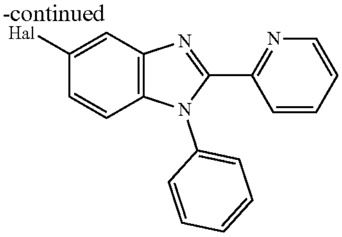

wherein

Hal, Hal1 and Hal2 each independently represent a halide, preferably selected from the group consisting of I, F, Cl and Br, or a pseudohalide, preferably selected from the group consisting of mesylate, triflate, tosylate and nonaflate.

Hal is most preferably Cl or Br;

Hal1 is most preferably I; and

Hal2 is most preferably F or Cl.

The residues, groups and indices $L_2$, $L_3$ and HetAr are defined above.

Details of the reaction steps and process conditions are mentioned in the examples of the present application. The production method of the compounds of formula (I) according to the present invention is not particularly limited and it is produced according to known methods, for example, by a Suzuki coupling as described in *Journal or American Chemistry Society,* 1999, 121, 9550 to 9561 or *Chemical Reviews,* 1995, 95, 2457 to 2483 or Kumada coupling described in *Org. Lett.,* 2010, 12, 2298-2301 or *Angew. Chem,* 2002, 114, 4218-4221 and references therein.

It has been found that the compounds of formula (1) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device (organic electroluminescence device) is used interchangeably with the term organic light-emitting diode (OLED) in the present application; i.e. both terms have the same meaning in the sense of the present application.

The present invention further relates to a material for an organic EL device comprising al least one compound of formula (I).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compound of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compound of formula (1).

The compounds of formula (I) being particularly suitable in OLEDs for use as charge and/or exciton-blocking material, i.e. as hole/exciton-blocking material, and/or charge-transporting material, i.e. hole-transporting material or electron-transporting material, preferably as electron-transporting material and/or hole-blocking material.

In the case of use of the inventive compounds of formula (I) in OLEDs, OLEDs having good overall properties, preferably a long lifetime, high efficiency and/or a low driving voltage are obtained.

Organic Electroluminescence Device

According to one aspect of the present invention, a material for an organic electroluminescence device, comprising at least one compound of formula (I) is provided.

According to another aspect of the invention, the following organic electroluminescence device is provided, comprising at least one compound of formula (I). The organic electroluminescence device generally comprises: a cathode, an anode, and one or more organic thin film layers comprising an emitting layer disposed between the cathode and the anode, wherein at least one layer of the organic thin film layers comprises at least one compound of formula (I).

In the present specification, regarding "one or more organic thin film layers disposed between the cathode and the anode", if only one organic layer is present between the cathode and the anode, it means the layer, and if plural organic layers are present between the cathode and the anode, it means at least one layer thereof.

According to another aspect of the invention, the use of a compound of formula (I) according to the present invention in an organic electroluminescence device is provided.

In one embodiment, the organic EL device has a hole-transporting layer between the anode and the emitting layer.

In one embodiment, the organic EL device has an electron-transporting layer between the cathode and the emitting layer.

In one embodiment, the organic EL device has a hole-blocking layer between the electron-transporting layer and the emitting layer.

Layer(s) Between The Emitting Layer and the Anode:

In the organic EL device according to the present invention, one or more organic thin film layers may be present between the emitting layer and the anode. If only one organic layer is present between the emitting layer and the anode, it means that layer, and if plural organic layers are present, it means at least one layer thereof. For example, if two or more organic layers are present between the emitting layer and the anode, an organic layer nearer to the emitting layer is called the "hole-transporting layer", and an organic layer nearer to the anode is called the "hole-injecting layer". Each of the "hole-transporting layer" and the "holeinjecting layer" may be a single layer or may be formed of two or more layers. One of these layers may be a single layer and the other may be formed of two or more layers.

Layer(s) Between The Emitting Layer and the Cathode:

Similarly, one or more organic thin film layers may be present between the emitting layer and the cathode, in the organic EL device according to the present invention (electron-transporting zone, at least including an electron-transporting layer and preferably also an electron-injecting layer and/or a hole-blocking layer). If only one organic layer is present between the emitting layer and the cathode it means that layer, and if plural organic layers are present, it means at least one layer thereof. For example, if two or more organic layers are present between the emitting layer and the cathode, an organic layer nearest to the emitting layer is called the "hole-blocking layer", an organic layer nearest to the "hole-blocking layer" is called the "electron-transporting layer", and an organic layer nearer to the cathode is called the "electron-injecting layer". Each of the "hole-blocking layer", "electron-transporting layer" and the "electron-injecting layer" may be a single layer or may be formed of two or more layers. One of these layers may be a single layer and the other may be formed of two or more layers.

The one or more organic thin film layers between the emitting layer and the cathode, preferably the "electron-transporting zone", preferably comprises a compound represented by formula (I).

Therefore, in a preferred embodiment, the organic thin film layers of the organic electroluminescence device comprise an electron-transporting zone provided between the emitting layer and the cathode, wherein the electron-transporting zone comprises at least one compound represented by formula (I). The compound represented by formula (I) preferably functions as "hole-blocking" material in the hole-blocking layer and/or "electron-transporting" material in the electron-transporting layer.

In an exemplary embodiment, the one or more organic thin film layers of the organic EL device of the present invention at least include the emitting layer and an electron-transporting zone. The electron-transporting zone is provided between the emitting layer and the cathode and at least includes an electron-transporting layer and preferably also an electron injecting layer and/or a hole-blocking layer. The electron-transporting zone may include the electron-injecting layer and an electron-transporting layer and may further include a hole-blocking layer and optionally a space layer. In addition to the above layers, the one or more organic thin film layers may be provided by layers applied in a known organic EL device such as a hole-injecting layer, a hole transporting layer and an electron-blocking layer. The one or more organic thin film layers may include an inorganic compound.

An explanation will be made on the layer configuration of the organic EL device according to one aspect of the invention.

An organic EL device according to one aspect of the invention comprises a cathode, an anode, and one or more organic thin film layers comprising an emitting layer disposed between the cathode and the anode. The organic layer comprises at least one layer composed of an organic compound. Alternatively, the organic layer is formed by laminating a plurality of layers composed of an organic compound. The organic layer may further comprise an inorganic compound in addition to the organic compound.

At least one of the organic layers is an emitting layer. The organic layer may be constituted, for example, as a single emitting layer, or may comprise other layers which can be adopted in the layer structure of the organic EL device. The layer that can be adopted in the layer structure of the organic EL device is not particularly limited, but examples thereof include a hole-transporting zone (a hole-transporting layer, a hole-injecting layer, an electron-blocking layer, an exciton-blocking layer, etc.), an emitting layer, a spacing layer, and an electron-transporting zone (electron-transporting layer, electron-injecting layer, hole-blocking layer, etc.) provided between the cathode and the emitting layer.

The organic EL device according to one aspect of the invention may be, for example, a fluorescent or phosphorescent monochromatic light emitting device or a fluorescent/phosphorescent hybrid white light emitting device.

Further, it may be a simple type device having a single emitting unit or a tandem type device having a plurality of emitting units.

The "emitting unit" in the specification is the smallest unit that comprises organic layers, in which at least one of the organic layers is an emitting layer and light is emitted by recombination of injected holes and electrons.

In addition, the emitting layer described in the present specification is an organic layer having an emitting function. The emitting layer is, for example, a phosphorescent emitting layer, a fluorescent emitting layer or the like, and may be a single layer or a stack of a plurality of layers.

The "emitting unit" may be a stacked type unit having a plurality of phosphorescent emitting layers and/or fluorescent emitting layers. In this case, for example, a spacing layer for preventing excitons generated in the phosphorescent emitting layer from diffusing into the fluorescent emitting layer may be provided between the respective light-emitting layers.

As the simple type organic EL device, a device configuration such as anode/emitting unit/cathode can be given.

Examples for Representative Layer Structures of the Emitting Unit are Shown Below.

The Layers in Parentheses are Provided Arbitrarily:

(a) (Hole-injecting layer/) Hole-transporting layer/Fluorescent emitting layer (/Electron-transporting layer/Electron-injecting layer)

(b) (Hole-injecting layer/) Hole-transporting layer/Phosphorescent emitting layer (/Electron-transporting layer/Electron-injecting layer)

(c) (Hole-injecting layer/) Hole-transporting layer/First fluorescent emitting layer/Second fluorescent emitting layer (/Electron-transporting layer/Electron-injecting layer)

(d) (Hole-injecting layer/) Hole-transporting layer/First phosphorescent layer/Second phosphorescent layer (/Electron-transporting layer/Electron-injecting layer)

(e) (Hole-injecting layer/) Hole-transporting layer/Phosphorescent emitting layer/Spacing layer/Fluorescent emitting layer (/Electron-transporting layer/Electron-injecting layer)

(f) (Hole-injecting layer/) Hole-transporting layer/First phosphorescent emitting layer/Second phosphorescent emitting layer/Spacing layer/Fluorescent emitting layer (/Electron-transporting layer/Electron-injecting layer)

(g) (Hole-injecting layer/) Hole-transporting layer/First phosphorescent layer/Spacing layer/Second phosphorescent emitting layer/Spacing layer/Fluorescent emitting layer (/Electron-transporting layer/Electron-injecting layer)

(h) (Hole-injecting layer/) Hole-transporting layer/Phosphorescent emitting layer/Spacing layer/First fluorescent emitting layer/Second fluorescent emitting layer (/Electron-transporting Layer/Electron-injecting Layer)

(i) (Hole-injecting layer/) Hole-transporting layer/Electron-blocking layer/Fluorescent emitting layer (/Electron-transporting layer/Electron-injecting layer)

(j) (Hole-injecting layer/) Hole-transporting layer/Electron-blocking layer/Phosphorescent emitting layer (/Electron-transporting layer/Electron-injecting layer)

(k) (Hole-injecting layer/) Hole-transporting layer/Exciton-blocking layer/Fluorescent emitting layer (/Electron-transporting layer/Electron-injecting layer)

(l) (Hole-injecting layer/) Hole-transporting layer/Exciton-blocking layer/Phosphorescent emitting layer (/Electron-transporting layer/Electron-injecting layer)

(m) (Hole-injecting layer/) First hole-transporting Layer/Second hole-transporting Layer/Fluorescent emitting layer (/Electron-transporting layer/electron-injecting Layer)

(n) (Hole-injecting layer/) First hole-transporting layer/Second hole-transporting layer/Fluorescent emitting layer (/First electron-transporting layer/Second electron-transporting layer/Electron-injection layer)

(o) (Hole-injecting layer/) First hole-transporting layer/Second hole-transporting layer/Phosphorescent emitting layer (/Electron-transporting layer/Electron-injecting Layer)

(p) (Hole-injecting layer/) First hole-transporting layer/Second hole-transporting layer/Phosphorescent emitting layer (/First electron-transporting Layer/Second electron-transporting layer/Electron-injecting layer)

(q) (Hole-injecting layer/) Hole-transporting layer/Fluorescent emitting layer/Hole-blocking layer (/Electron-transporting layer/Electron-injecting layer)

(r) (Hole-injecting layer/) Hole-transporting layer/Phosphorescent emitting layer/Hole-blocking layer (/Electron-transport layer/Electron-injecting layer)

(s) (Hole-injecting layer/) Hole-transporting layer/Fluorescent emitting layer/Exciton-blocking layer (/Electron-transporting layer/Electron-injecting layer)

(t) (Hole-injecting layer/) Hole-transporting layer/Phosphorescent emitting layer/Exciton-blocking layer (/Electron-transporting layer/Electron-injecting layer)

The layer structure of the organic EL device according to one aspect of the invention is not limited to the examples mentioned above.

For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be formed of a single layer or be formed of a plurality of layers.

The plurality of phosphorescent emitting layers and/or fluorescent emitting layers may be emitting layers that emit mutually different colors. For example, the emitting unit (f) may include a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve light emitting efficiency.

As a Representative Device Configuration of a Tandem Type Organic EL Device, for Example, a Device Configuration Such as Anode/First Emitting Unit/Intermediate Layer/Second Emitting Unit/Cathode can be Given:

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed from known materials.

The FIGURE shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole-injecting and transporting layer 6 or the like may be provided between the emitting layer 5 and the anode 3 and an electron-injecting layer 9 and an electron-transporting layer 8 and/or a hole-blocking layer 7 or the like (electron-transporting zone 11) may be provided between the emitting layer 5 and the cathode 4. An electron-blocking layer may be provided on the anode 3 side of the emitting layer 5. Due to such configuration, electrons or holes can be confined in the emitting layer 5, whereby possibility of generation of excitons in the emitting layer 5 can be improved.

Hereinbelow, an explanation will be made on function, materials, etc. of each layer constituting the organic EL device described in the present specification.

(Substrate)

The substrate is used as a support of the organic EL device. The substrate preferably has a light transmittance of 50% or more in the visible light region with a wavelength of 400 to 700 nm, and a smooth substrate is preferable. Examples of the material of the substrate include glass, like soda-lime glass, aluminosilicate glass, quartz glass, plastic and the like. As a substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like and having a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is also possible to use gold, silver, platinum, nickel, tungsten, chromium, molybdenum, iron, cobalt, copper, palladium, titanium, and nitrides of these metals (e.g. titanium oxide).

The anode is normally formed by depositing these materials on the substrate by a sputtering method. For example, indium oxide-zinc oxide can be formed by a sputtering method by using a target in which 1 to 10 mass % zinc oxide is added relative to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added relative to indium oxide. As other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, e.g. a metal, an alloy, a conductive compound and a mixture thereof. Specifically, a material having a small work function such as alkaline metals such as lithium and cesium; alkaline earth metals such as calcium and strontium; alloys containing these metals (for example, magnesium-silver and aluminum-lithium); rare earth metals such as europium and ytterbium; and an alloy containing rare earth metals.

(Hole-Transporting Layer)/(Hole-Injecting Layer/Electron-Blocking Layer)

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode. Said hole-injecting layer is generally used for stabilizing hole injection from anode to hole-transporting layer which is generally consist of organic materials. Organic material having good contact with anode or organic material with p-type doping is preferably used for the hole-injecting layer.

p-doping usually consists of one or more p-dopant materials and one or more matrix materials. Matrix materials preferably have shallower HOMO level and p-dopant preferably have deeper LUMO level to enhance the carrier density of the layer. Aryl or heteroaryl amine compounds are preferably used as the matrix materials. Specific examples for the matrix material are the same as that for hole-transporting layer which is explained at the later part. Specific examples for p-dopant are the below mentioned acceptor materials, preferably the quinone compounds with one or more electron withdrawing groups, such as $F_4$TCNQ, 1,2,3-Tris[(cyano) (4-cyano-2,3,5,6-tetrafluorophenyl) methylene]cyclopropane.

Acceptor materials, or fused aromatic hydrocarbon materials or fused heterocycles which have high planarity, are preferably used as p-dopant materials for the hole-injecting layer.

Specific examples for acceptor materials are, the quinone compounds with one or more electron withdrawing groups, such as $F_4$TCNQ(2,3,5,6-tetrafluoro-7,7,8,8-tetracyanoquinodimethane), and 1,2,3-tris[(cyano) (4-cyano-2,3,5,6-tetrafluorophenyl)methylene]cyclopropane; hexa-azatriphenylene compounds with one or more electron withdrawing groups, such as hexa-azatriphenylene-hexanitrile; aromatic hydrocarbon compounds with one or more electron withdrawing groups; and aryl boron compounds with one or more electron withdrawing groups.

The ratio of the p-type dopant is preferably less than 20% of molar ratio, more preferably less than 10%, such as 1%, 3%, or 5%, related to the matrix material.

The hole-transporting layer is generally used for injecting and transporting holes efficiently, and aromatic or heterocyclic amine compounds are preferably used. Specific examples for compounds for the hole-transporting layer are represented by the general formula (H),

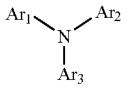
(H)

wherein $Ar_1$ to $Ar_3$ each independently represents substituted or unsubstituted aryl group having 5 to 50 carbon atoms or substituted or unsubstituted heterocyclic group having 5 to 50 ring atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1$ to $Ar^3$ may be bonded to each other to form a ring structure, such as a carbazole ring structure, or a acridane ring structure.

Preferably, at least one of $Ar_1$ to $Ar_3$ have additional one aryl or heterocyclic amine substituent, more preferably $Ar_1$ has an additional aryl amino substituent, at the case of that it is preferable that $Ar_1$ represents substituted or unsubstituted biphenylene group, substituted or unsubstituted fluorenylene group.

A second hole-transporting layer is preferably inserted between the first hole-transporting layer and the emitting layer to enhance device performance by blocking excess electrons or excitons.

Specific examples for second hole-transporting layer are the same as for the the first hole-transporting layer. It is preferred that second hole-transporting layer has higher triplet energy to block triplet excitons, such as bicarbazole compounds, biphenylamine compounds, triphenylenyl amine compounds, fluorenyl amine compounds, carbazole substituted arylamine compounds, dibenzofuran substituted arylamine compounds, and dibenzothiophene substituted arylamine compounds.

This second hole-transporting layer also called electron-blocking layer provided adjacent to the emitting layer has a function of preventing leakage of electrons from the emitting layer to the hole-transporting layer.

(Emitting Layer)

The emitting layer is a layer containing a substance having a high emitting property (emitter material or dopant material). As the dopant material, various materials can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called a fluorescent emitting layer. Further, a phosphorescent emitting compound is a compound capable of emitting light from the triplet excited state, and an emitting layer containing a phosphorescent emitting compound is called a phosphorescent emitting layer.

The emitting layer preferably comprises at least one dopant material and at least one host material that allows it to emit light efficiently. In some literatures, a dopant material is called a guest material, an emitter or an emitting material. In some literatures, a host material is called a matrix material.

A single emitting layer may comprise plural dopant materials and plural host materials. Further, plural emitting layers may be present.

In the present specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but does not mean that it cannot be used as a material for forming a fluorescent emitting layer. The same can be applied to the fluorescent host.

No specific restrictions are generally imposed on the content of the dopant material in a host in the emitting layer. A person skilled in the art generally knows the concentration of a phosphorescent dopant respectively a fluorescent dopant usually present in a suitable host. In respect of sufficient emission and concentration quenching, the content is preferably 0.5 to 70 mass %, more preferably 0.8 to 30 mass %, further preferably 1 to 30 mass %, still further preferably 1 to 20 mass. The remaining mass of the emitting layer is generally provided by one or more host materials.

(Fluorescent Dopant)

Suitable fluorescent dopants are generally known by a person skilled in the art. As a fluorescent dopant a fused polycyclic aromatic compound, a styrylamine compound, a fused ring amine compound, a boron-containing compound, a pyrrole compound, an indole compound, a carbazole compound can be given, for example. Among these, a fused ring amine compound, a boron-containing compound, carbazole compound is preferable.

As the fused ring amine compound, a diaminopyrene compound, a diaminochrysene compound, a diaminoanthracene compound, a diaminofluorene compound, a diaminofluorene compound with which one or more benzofuro skeletons are fused, or the like can be given.

As the boron-containing compound, a pyrromethene compound, a triphenylborane compound or the like can be given.

(Phosphorescent Dopant)

Suitable phosphorescent dopants are generally known by a person skilled in the art. As a phosphorescent dopant, a phosphorescent emitting heavy metal complex and a phosphorescent emitting rare earth metal complex can be given, for example. As the heavy metal complex, an iridium complex, an osmium complex, a platinum complex or the like can be given. The heavy metal complex is for example an ortho-metalated complex of a metal selected from iridium, osmium and platinum. Examples of rare earth metal complexes include terbium complexes, europium complexes and the like. Specifically, tris(acetylacetonate)(monophenanthroline)terbium(III) (abbreviation: $Tb(acac)_3(Phen)$), tris(1,3-diphenyl-1,3-propandionate) (monophenanthroline)europium(III) (abbreviation: $Eu(DBM)_3(Phen)$), tris[1-(2-thenoyl)-3,3,3-trifluoroacetonate](monophenanthroline)europium(III) (abbreviation: $Eu(TTA)_3(Phen)$) or the like can be given. These rare earth metal complexes are preferable as phosphorescent dopants since rare earth metal ions emit light due to electronic transition between different multiplicity.

As a blue phosphorescent dopant, an iridium complex, an osmium complex, a platinum complex, or the like can be given, for example. Specifically, bis[2-(4',6'-difluorophenyl)

pyridinate-N,C2']iridium(III) tetrakis(1-pyrazolyl)borate (abbreviation: FIr6), bis[2-(4',6'-difluorophenyl) pyridinato-N,C2']iridium(III) picolinate (abbreviation: $Ir(CF_3ppy)_2$ (pic)), bis[2-(4',6'-difluorophenyl)pyridinato-N,C2']iridium (III) acetylacetonate (abbreviation: FIracac) or the like can be given.

As a green phosphorescent dopant, an iridium complex or the like can be given, for example. Specifically, tris(2-phenylpyridinato-N,C2') iridium(III) (abbreviation: Ir(ppy) $_3$), bis(1,2-diphenyl-1H-benzimidazolato)iridium(III) acetylacetonate (abbreviation: $Ir(pbi)_2$(acac)), bis(benzo[h] quinolinato)iridium(III) acetylacetonate (abbreviation: $Ir(bzq)_2$(acac)) or the like can be given.

As a red phosphorescent dopant, an iridium complex, a platinum complex, a terbium complex, an europium complex or the like can be given. Specifically, bis[2-(2'-benzo [4,5-α]thienyl)pyridinato-N, C3']iridium(III) acetylacetonate (abbreviation: $Ir(btp)_2$(acac)), bis(1-phenylisoquinolinato-N,C2')iridium(III) acetylacetonate (abbreviation: $Ir(piq)_2$(acac)), (acetylacetonato)bis[2,3-bis (4-fluorophenyl)quinoxalinato]iridium(III) (abbreviation: $Ir(Fdpq)_2$(acac)), 2,3,7,8,12,13,17,18-octaethyl-21H,23H-porphyrin platinum(II) (abbreviation PtOEP) or the like can be given.

(Host Material)

As host material, metal complexes such as aluminum complexes, beryllium complexes and zinc complexes; heterocyclic compounds such as indole compounds, pyridine compounds, pyrimidine compounds, triazine compounds, quinoline compounds, isoquinoline compounds, quinazoline compounds, dibenzofuran compounds, dibenzothiophene compounds, oxadiazole compounds, benzimidazole compounds, phenanthroline compounds; fused polyaromatic hydrocarbon (PAH) compounds such as a naphthalene compound, a triphenylene compound, a carbazole compound, an anthracene compound, a phenanthrene compound, a pyrene compound, a chrysene compound, a naphthacene compound, a fluoranthene compound; and aromatic amine compound such as triarylamine compounds and fused polycyclic aromatic amine compounds can be given, for example. Plural types of host materials can be used in combination.

As a fluorescent host, a compound having a higher singlet energy level than a fluorescent dopant is preferable. For example, a heterocyclic compound, a fused aromatic compound or the like can be given. As a fused aromatic compound, an anthracene compound, a pyrene compound, a chrysene compound, a naphthacene compound or the like are preferable. An anthracene compound is preferentially used as blue fluorescent host.

As a phosphorescent host, a compound having a higher triplet energy level as compared with a phosphorescent dopant is preferable. For example, a metal complex, a heterocyclic compound, a fused aromatic compound or the like can be given. Among these, an indole compound, a carbazole compound, a pyridine compound, a pyrimidine compound, a triazine compound, a quinolone compound, an isoquinoline compound, a quinazoline compound, a dibenzofuran compound, a dibenzothiophene compound, a naphthalene compound, a triphenylene compound, a phenanthrene compound, a fluoranthene compound or the like can be given.

Preferred host materials are substituted or unsubstituted polyaromatic hydrocarbon (PAH) compounds, substituted or unsubstituted polyheteroaromatic compounds, substituted or unsubstituted anthracene compounds, or substituted or unsubstituted pyrene compounds, preferably substituted or unsubstituted anthracene compounds or substituted or unsubstituted pyrene compounds, more preferably substituted or unsubstituted anthracene compounds, most preferably anthracene compounds represented by formula (10) below.

(10)

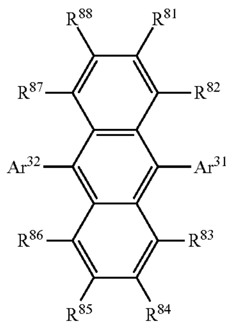

In the formula (10), $Ar^{31}$ and $Ar^{32}$ each independently represent a substituted or unsubstituted aryl group having 6 to 50 ring carbon atoms or a heterocyclic group having 5 to 50 ring atoms.

$R^{81}$ to $R^{88}$ each independently represent a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group.

In formula (10):

The aryl group having 6 to 50 ring carbon atoms is preferably an aryl group having 6 to 40 ring carbon atoms, more preferably an aryl group having 6 to 30 ring carbon atoms.

The heterocyclic group having 5 to 50 ring atoms is preferably a heterocyclic group having 5 to 40 ring atoms, more preferably a heterocyclic group having 5 to 30 ring atoms. More preferably, the heterocyclic group is a substituted or unsubstituted heteroaryl group having 5 to 30 ring atoms. Suitable substituted or unsubstituted heteroaryl groups are mentioned above.

The alkyl group having 1 to 50 carbon atoms is preferably an alkyl group having 1 to 30 carbon atoms, more preferably an alkyl group having 1 to 10 carbon atoms, further preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, further preferably an alkoxy group having 1 to 5 carbon atoms.

The aralkyl group having 7 to 50 carbon atoms is preferably an aralkyl group having 7 to 30 carbon atoms, more preferably an aralkyl group having 7 to 20 carbon atoms.

The aryloxy group having 6 to 50 ring carbon atoms is preferably an aryloxy group having 6 to 40 ring carbon atoms, more preferably an aryloxy group having 6 to 30 ring carbon atoms.

The arylthio group having 6 to 50 ring carbon atoms is preferably an arylthio group having 6 to 40 ring carbon atoms, more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, further preferably an alkoxycarbonyl group having 2 to 5 carbon atoms.

Examples of the halogen atom are a fluorine atom, a chlorine atom and a bromine atom.

$Ar^{31}$ and $Ar^{32}$ are preferably a substituted or unsubstituted aryl group having 6 to 50 ring carbon atoms.

(Electron-Transporting Zone)/(Electron-Transporting Layer/Electron-Injecting Layer/Hole-Blocking Layer)

The electron-transporting zone is an organic layer or a plurality of organic layers that is formed between the emitting layer and the cathode and has a function of transporting electrons from the cathode to the emitting layer. The electron-transporting zone therefore comprises at least one electron-transporting layer comprising an electron-transporting material. When the electron-transporting zone is formed of plural layers, an organic layer or an inorganic layer that is nearer to the cathode is often defined as the electron-injecting layer (see for example the FIGURE, wherein an electron-injecting layer 9, an electron-transporting layer and preferably a hole-blocking layer 7 form an electron-transporting zone 11). The electron-injecting layer has a function of injecting electrons from the cathode efficiently to the organic layer unit. Preferred electron-injecting materials are alkali metal, alkali metal compounds, alkali metal complexes, the alkaline earth metal complexes and compounds and rare earth metals or rare earth metal complexes and compounds. Suitable rare earth metals and rare earth metal compounds and complexes are mentioned below. Most preferred is ytterbium. In one embodiment of the present invention, the electron-injecting layer does not comprise Liq, preferably, the electron-injecting layer does not comprise alkali metal complexes or compounds.

According to one embodiment, it is therefore preferred that the electron-transporting zone comprises in addition to the electron-transporting layer one or more layer(s) like an electron-injecting layer to enhance efficiency and lifetime of the device, a hole-blocking layer or an exciton/triplet-blocking layer (layer 7 in the FIGURE).

In one preferred embodiment of the present invention, the compound of the formula (I) is present in the electron-transporting zone, as an electron-transporting material, an electron-injecting material, a hole-blocking material, an exciton-blocking material and/or a triplet-blocking material. More preferably, the compound of the formula (I) is present in the electron-transporting zone as an electron-transporting material and/or a hole-blocking material.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Li (work function: 2.9 eV), Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV), Mg (work function: 3.68 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali chalcogenide such as $Li_2O$, $Na_2O$, $Cs_2O$, $K_2O$, $Na_2S$ or $Na_2Se$, and an alkali halide such as LiF, NaF, CsF, KF, LiCl, KCl and NaCl. Among them, LiF, $Li_2O$ and NaF are preferable. Examples of the alkaline earth metal compound include BaO, SrO, CaO, BeO, BaS, CaSe and mixtures thereof such as $Ba_xSr_{1-x}O$ ($0<x<1$) and $Ba_xCa_{1-x}O$ ($0<x<1$). Alkaline earth metal halides are for example fluorides such as $CaF_2$, $BaF_2$, $SrF_2$, $MgF_2$ and $ReF_2$. Among them, BaO, SrO and CaO are preferable. Examples of the rare earth metal compounds include one or more oxides, nitrides, oxidized nitrides or halides, especially fluorides, containing at least one element selected from Yb, Sc, Y, Ce, Gd, Tb and the like, for example $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable. Further suitable dopants are one or more oxides, nitrides and oxidized nitrides of Al, Ga, In, Cd, Si, Ta, Sb and Zn and nitrides and oxidized nitrides of Ba, Ca, Sr, Yb, Li, Na and Mg.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, and azomethines.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

As the electron-transporting material used in the electron-transporting layer other than a compound of the formula (I), an aromatic heterocyclic compound having one or more hetero atoms in the molecule may preferably be used. In particular, a nitrogen containing heterocyclic compound is preferable.

According to one embodiment, it is preferable that the electron-transporting layer comprises a nitrogen containing heterocyclic metal chelate.

According to another embodiment, it is preferable that the electron-transporting layer comprises a substituted or unsubstituted nitrogen containing heterocyclic compound. Specific examples of preferred heterocyclic compounds for the electron-transporting layer are, 6-membered azine compounds; such as pyridine compounds, pyrimidine compounds, triazine compounds, pyrazine compounds, preferably pyrimidine compounds or triazine compounds; 6-membered fused azine compounds, such as quinolone compounds, isoquinoline compounds, quinoxaline compounds, quinazoline compounds, phenanthroline compounds, benzoquinoline compounds, benzoisoquinoline compounds, dibenzoquinoxaline compounds, preferably quinolone compounds, isoquinoline compounds, phenanthroline compounds; 5-membered heterocyclic compounds, such as imidazole compounds, oxazole compounds, oxadiazole compounds, triazole compounds, thiazole compounds, thiadiazole compounds; fused imidazole compounds, such as benzimidazole compounds, imidazopyridine compounds, naphthoimidazole compounds, benzimidazophenanthridine compounds, benzimidzobenzimidazole compounds, preferably benzimidazole compounds, imidazopyridine compounds or benzimidazophenanthridine compounds.

According to another embodiment, it is preferable the electron-transporting layer comprises a phosphine oxide compound represented as $Ar_{p1}Ar_{p2}Ar_{p3}P{=}0$. $Ar_{p1}$ to $Ar_{p3}$ are the substituents of phosphor atom and each independently represent substituted or unsubstituted above mentioned aryl group or substituted or unsubstituted above mentioned heterocyclic group.

According to another embodiment, it is preferable that the electron-transporting layer comprises aromatic hydrocarbon compounds. Specific examples of preferred aromatic hydrocarbon compounds for the electron-transporting layer are, oligo-phenylene compounds, naphthalene compounds, fluorene compounds, fluoranthenyl group, anthracene compounds, phenanthrene compounds, pyrene compounds, triphenylene compounds, benzanthracene compounds, chrysene compounds, benzphenanthrene compounds, naphthacene compounds, and benzochrysene compounds, preferably anthracene compounds, pyrene compounds and fluoranthene compounds.

A hole-blocking layer may be provided adjacent to the emitting layer, and has a function of preventing leakage of holes from the emitting layer to the electron-transporting layer. In order to improve hole-blocking capability, a material having a deep HOMO level is preferably used.

In a preferred embodiment, the organic electroluminescence device according to the present invention, comprises an electron-transporting zone, wherein the electron-transporting zone further comprises at least one of an electron-donating dopant and preferably at least one metal, metal complex or metal compound, wherein the at least one metal, metal complex or metal compound is preferably at least one selected from the group consisting of an alkali metal, an alkali metal compound, an alkali metal complex, an alkaline earth metal, an alkaline earth metal compound, an alkaline earth metal complex, a rare earth metal, a rare earth metal compound, and a rare earth metal complex. Suitable dopants are mentioned above.

More preferably, the at least one of an electron-donating dopant is at least one selected from the group consisting of an alkali metal, an alkali metal compound, an alkali metal complex, an alkaline earth metal, an alkaline earth metal compound, an alkaline earth metal complex, a rare earth metal, a rare earth metal compound, and a rare earth metal complex.

(Cathode)

For the cathode, a metal, an alloy, an electrically conductive compound, and a mixture thereof, each having a small work function (specifically, a work function of 3.8 eV or less) are preferably used. Specific examples of a material for the cathode include an alkali metal such as lithium and cesium; an alkaline earth metal such as magnesium, calcium, and strontium; an alloy containing these metals (for example, magnesium-silver, aluminum-lithium); a rare earth metal such as europium and ytterbium; and an alloy containing a rare earth metal or aluminum.

The cathode is usually formed by a vacuum vapor deposition or a sputtering method. Further, in the case of using a silver paste or the like, a coating method, an inkjet method, or the like can be employed.

Moreover, when the electron-injecting layer is provided, various electrically conductive materials such as aluminum, silver, ITO, graphene, indium oxide-tin oxide containing silicon or silicon oxide, selected independently from the work function, can be used to form a cathode. These electrically conductive materials are made into films using a sputtering method, an inkjet method, a spin coating method, or the like.

(Insulating Layer)

In the organic EL device, pixel defects based on leakage or a short circuit are easily generated since an electric field is applied to a thin film. In order to prevent this, it is preferred to insert an insulating thin layer between a pair of electrodes. Examples of materials used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture thereof may be used in the insulating layer, and a laminate of a plurality of layers that include these materials can be also used for the insulating layer.

(Spacing Layer)

A spacing layer is a layer for example provided between a fluorescent emitting layer and a phosphorescent emitting layer when a fluorescent emitting layer and a phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is for example provided between the emitting layers, the material used for the spacing layer is preferably a material having both electron-transporting capability and hole-transporting capability. In order to prevent diffusion of the triplet energy in adjacent phosphorescent emitting layers, it is preferred that the spacing layer have a triplet energy of 2.6 eV or more. As the material used for the spacing layer, the same materials as those used in the above-mentioned hole-transporting layer can be given.

(Triplet-Blocking Layer)

A triplet-blocking layer (exciton-blocking layer) may be provided adjacent to the emitting layer.

The triplet-blocking layer has a function of preventing triplet excitons generated in the emitting layer from diffusing into neighboring layers to trap the triplet excitons within the emitting layer, thereby suppressing energy deactivation of the triplet excitons on molecules other than the emitting dopant in the electron-transporting layer.

When the triplet-blocking layer is provided in a phosphorescent device, triplet energy of a phosphorescent dopant in the emitting layer is denoted as ET d and triplet energy of a compound used as the triplet-blocking layer is denoted as ET TB. In an energy relationship of ET d<ET TB, triplet excitons of the phosphorescent dopant are trapped (cannot be transferred to another molecule) to leave no alternative route for energy deactivation other than emission on the dopant, so that highly efficient emission can be expected. However, when an energy gap (ΔET=ET TB−ET d) is small even though the relationship of ET d<ET TB is satisfied, under actual environments for driving a device (i.e., at around the room temperature), it is considered that triplet excitons can be transferred to another molecule irrespective of the energy gap ΔET by absorbing heat energy around the device. Particularly, since the excitons of the phosphorescent device have longer lifetime than those of a fluorescent device, influence by heat absorption during transfer of the excitons is more likely to be given on the phosphorescent device relative to the fluorescent device. A larger energy gap ΔET relative to heat energy at the room temperature is preferable, more preferably 0.1 eV or more, further preferable at 0.2 eV or more. On the other hand, in the fluorescent device, the organic-EL-device material according to the exemplary embodiment is usable as the triplet-blocking layer in the TTF device structure described in International Publication WO2010/134350A1.

(Method for Forming a Layer)

The method for forming each layer of the organic EL device of the invention is not particularly limited unless otherwise specified. A known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, an inkjet method, and the like.

(Film Thickness)

The film thickness of each layer of the organic EL device of the invention is not particularly limited unless otherwise specified. If the film thickness is too small, defects such as pinholes are likely to occur to make it difficult to obtain a sufficient luminance. If the film thickness is too large, a high driving voltage is required to be applied, leading to a lowering in efficiency. In this respect, the film thickness is preferably 5 nm to 10 μm, and more preferably 10 nm to 0.2 μm.

(Electronic Apparatus (Electronic Equipment))

The present invention further relates to an electronic equipment (electronic apparatus) comprising the organic electroluminescence device according to the present application. Examples of the electronic apparatus include display parts such as an organic EL panel module; display devices of television sets, mobile phones, smart phones, and personal computer, and the like; and emitting devices of a lighting device and a vehicle lighting device.

It should be noted that the invention is not limited to the above exemplary embodiments but may include any modification and improvement as long as such modification and improvement are compatible with the invention.

The following examples are included for illustrative purposes only and do not limit the scope of the claims. Unless otherwise stated, all parts and percentages are by weight.

EXAMPLES

I Preparation Examples

Compound 1

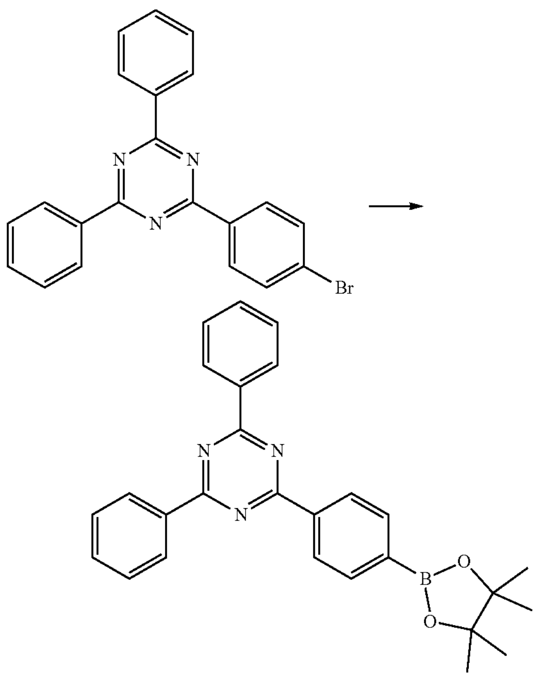

Intermediate 1

In a nitrogen flushed 1000 ml three-necked round-bottomed flask 2-(4-bromophenyl)-4,6-diphenyl-1,3,5-triazine (40 g, 103 mmol), bis(pinacolato)diboron (65.4 g, 258 mmol), [1,1'-bis(diphenylphosphino)ferrocene]dichloropalladium(II), complex with dichloromethane (4.2 g, 5.1 mmol), and potassium acetate (30.3 g, 309 mmol) were dissolved in 350 ml N,N-dimethylformamide under nitrogen. The reaction mixture was heated to 70° C. with an oil bath for 2 hours. After cooling down to room temperature, the reaction mixture was poured into water while stirring. The precipitate thus formed was collected by filtration. The precipitate was then suspended in methanol (1 L) and allowed to stir at room temperature for 2 hours. The precipitate was again collected by filtration and allowed to dry. The crude product was then dissolved in dichloromethane and filtered over a pad of silica, washing through with dichloromethane. After evaporation of the dichloromethane under reduced pressure, 40.6 g (91% yield) of a white solid was obtained which was used without further purification. The identification of Intermediate 1 was made by EST-MS (electrospray ionisation mass spectrometry) The results are shown below.

ESI-MS: calcd. for C27H26BN3O2=453, mass found=454 (M+1)

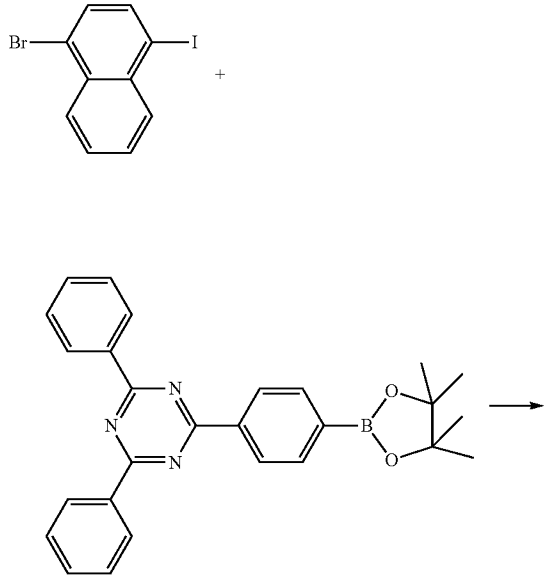

Intermediate 1

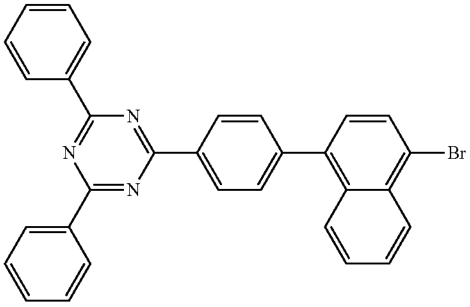

Intermediate 2

In a nitrogen flushed 500 ml three-necked round-bottomed flask, 1-bromo-4-iodonaphthalene (8.9 g, 26.7 mmol) was combined with Intermediate 1 (11 g, 25.4 mmol) and [1,1'-Bis(diphenylphosphino)ferrocene]dichloropalladium (II), complex with dichloromethane (1.1 g, 1.3 mmol) in 1,4-dioxane (160 mL) followed by the addition of 2M aqueous sodium carbonate (40 ml, 80 mmol). The reaction mixture was heated under reflux for 6 hours. The reaction was allowed to cool to room temperature and the precipitate that formed was collected by filtration. The crude product was suspended in a solution of water/methanol (1:1, 500 mL) and allowed to stir at room temperature for 1 hour. The precipitate was collected by filtration and washed with water and methanol and allowed to dry. The crude product was then stirred in acetone at room temperature and then collected by filtration. The product (12 g, 88%) thus obtained was used without further purification. The identification of Intermediate 2 was made by ESI-MS (electrospray ionisation mass spectrometry). The results are shown below.

ESI-MS: calcd. for C31H20BrN3=514, mass found=415 (M+1)

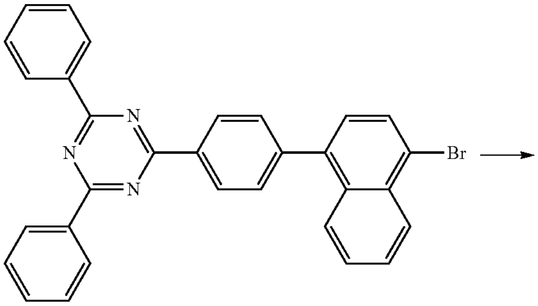

Intermediate 2

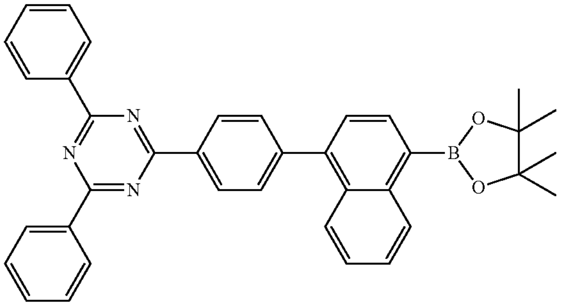

Intermediate 3

The procedure of the synthesis of Intermediate 1 was repeated except for intermediate 2 in place of 2-(4-bromophenyl)-4,6-diphenyl-1,3,5-triazine. The obtained Intermediate 3 (84% yield, white solid) was characterized by by ESI-MS (electrospray ionisation mass spectrometry). The results are shown below.

ESI-MS: calcd. for C37H32BN3O2=561, mass found=562 (M+1)

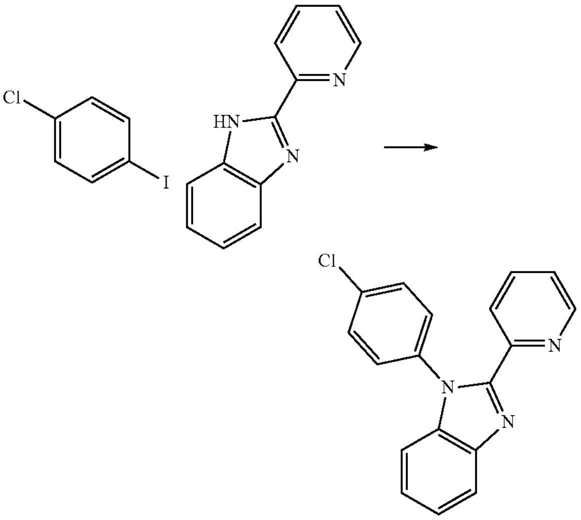

Intermediate 4

In a nitrogen flushed 500 mL 3 neck round bottom flask was added 1-chloro-4-iodobenzene (13.4 g, 56.3 mmol), 2-(pyridin-2-yl)-1H-benzo[d]imidazole (10 g, 51.2 mmol), copper(I) iodide (1.4 g, 7.7 mmol) and 1,10-phenanthroline (2.3 g, 12.8 mmol) followed by cesium carbonate (40 g, 123 mmol) and the mixture degassed under N2. N,N-dimethylformamide (anhydrous, 200 mL) was added and the resulting reaction mixture heated at an external temperature of 140° C. for 16 hours. The reaction was allowed to cool to room temperature and poured into a solution of 5% aqueous NH3 while stirring and the mixture was allowed to stir at room temperature for 1 hour. The precipitate was then collected by filtration. Further purification was carried out by chromatography on silica and the desired Intermediate 4 (13.9 g, 89%) was obtained as a white solid and used without further purification. Intermediate 4 was identified by ESI-MS. The results are shown below ESI-MS: calcd. for C18H12C1N3=306, mass found=306 (M+)

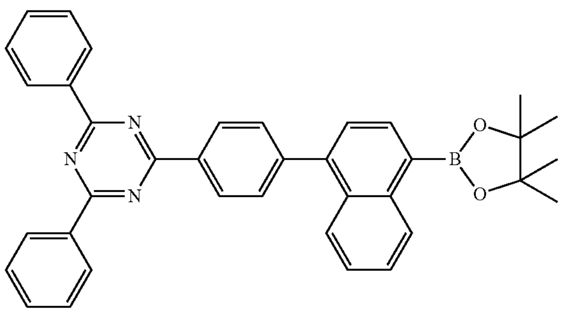

Intermediate 3

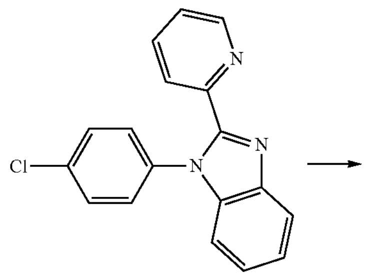

Intermediate 4

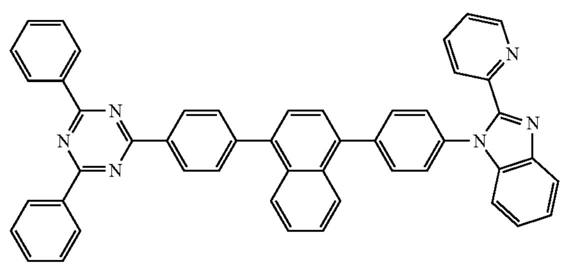

Compound 1

In a nitrogen flushed 250 ml three-necked round-bottomed flask, Intermediate 3 (3 g, 5.4 mmol) was combined with intermediate 4 (1.6 g, 5.4 mmol), palladium(II) acetate (30 mg g, 0.13 mmol), 2-Dicyclohexylphosphino-2',4',6'-triisopropylbiphenyl (0.25 g, 0.53 mmol) and cesium carbonate (4.3 g, 13.3 mmol). Dioxane (32 mL) and water (8 mL) was added to the reaction mixture and then heated at an oil bath temperature of 90° C. overnight. The reaction was then allowed to cool to room temperature and the solvent removed under reduced pressure. The crude residue was dissolved in dichloromethane and washed with saturated aqueous sodium hydrogen carbonate, followed by water and finally brine. The dichloromethane solution was then dried over anhydrous magnesium sulfate and filtered over a pad of silica gel washing through with dichloromethane. The silica was then washed with 10% methanol in DCM to elute the target compound. The solvent was evaporated under reduced pressure. The crude residue was then taken up in methanol and stirred at room temperature for 1 hour. The precipitate was isolated by filtration. Further purification was carried out by recrystallisation from xylene. The obtained Compound 1 (74% yield, white solid) was characterized by ESI-MS, maximum ultraviolet absorption wavelength (UV (PhMe) λ onset) in toluene, and maximum fluorescence wavelength (FL(PhMe, λ ex=330 nm) λ max) in toluene. The results are shown below. ESI-MS: calcd. for C49H32N6=705, mass found=705 (M+)

UV (PhMe) λ onset: 374 nm

FL (PhMe, λ ex=330 nm) max: 425 nm

Compound 2

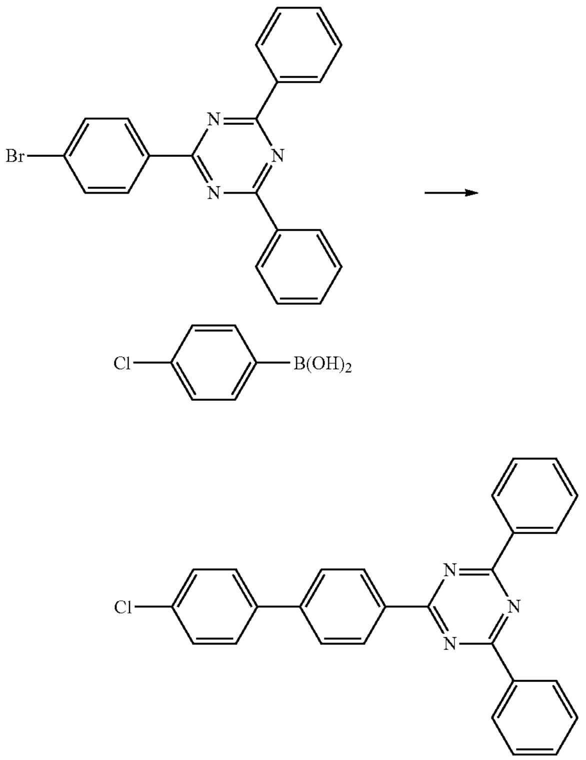

Intermediate 5

The procedure of the synthesis of Intermediate 2 was repeated except for using 2-(4-bromophenyl)-4,6-diphenyl-1,3,5-triazine in place of 1-bromo-4-iodonaphthalene and (4-chlorophenyl)boronic acid in place of Intermediate 1. The obtained Intermediate 5 (74% yield, white solid) was characterized by by ESI-MS (electrospray ionisation mass spectrometry). The results are shown below.

ESI-MS: calcd. for C32H20F3N303S=583, mass found=584 (M+1)

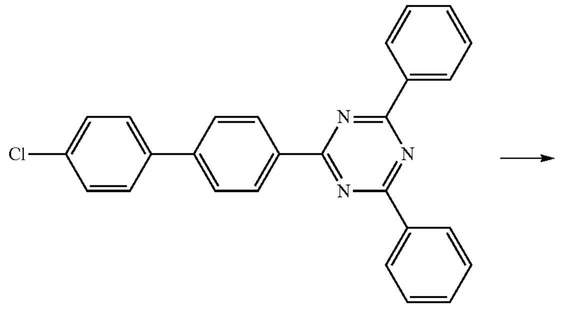

Intermediate 5

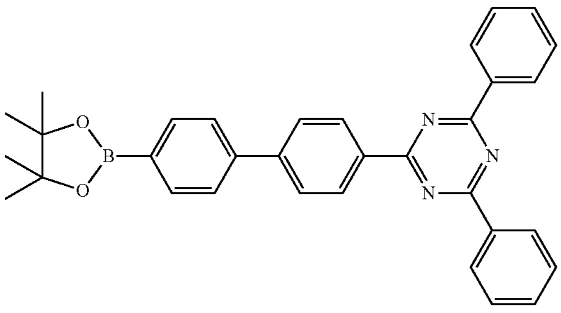

Intermediate 6

The procedure of the synthesis of Intermediate 1 was repeated except for using Intermediate 5 in place of 2-(4-bromophenyl)-4,6-diphenyl-1,3,5-triazine and palladium(II) acetate and [2-dicyclohexylphosphino-2',4',6'-triisopropyl-biphenyl] in place of [1,1'-bis(diphenylphosphino) ferrocene]dichloropalladium(II), complex with dichloromethane. The obtained Intermediate 6 (97% yield, white solid) was characterized by by ESI-MS (electrospray ionisation mass spectrometry). The results are shown below.

ESI-MS: calcd. for C33H30BN3O2=511, mass found=512 (M+1)

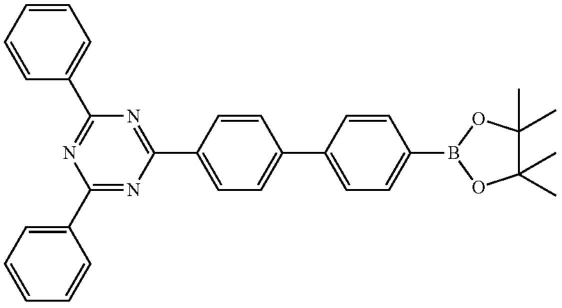

Intermediate 6

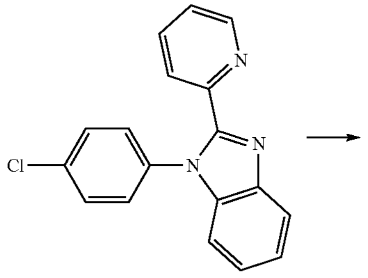

Intermediate 4

-continued

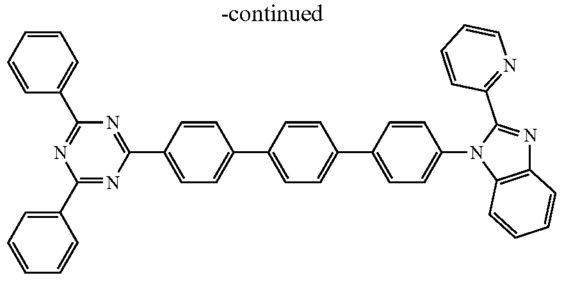

Compound 2

The procedure of the synthesis of Compound 1 was repeated except for Intermediate 6 in place of Intermediate 3. The obtained Compound 2 (98% yield, white solid) was characterized by ESI-MS, maximum ultraviolet absorption wavelength (UV(PhMe) λ onset) in toluene, and maximum fluorescence wavelength (FL(PhMe, λ ex=330 nm) λ max) in toluene. The results are shown below.

ESI-MS: calcd. for C45H30N6=655, mass found=655 (M+)

UV(PhMe) λ onset: 369 nm

FL(PhMe, λ ex=330 nm) λ max: 405 nm

Compound 3

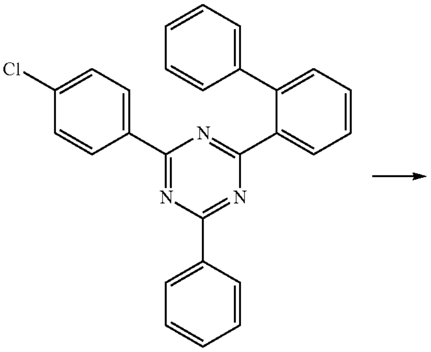

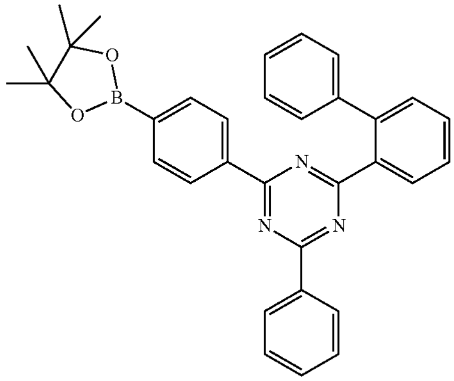

Intermediate 7

The procedure of the synthesis of Intermediate 1 was repeated except for using 2-([1,1'-biphenyl]-2-yl)-4-(4-chlorophenyl)-6-phenyl-1,3,5-triazine in place of 2-(4-bromophenyl)-4,6-diphenyl-1,3,5-triazine and palladium(II)acetate and [2-dicyclohexylphosphino-2',4',6'-triisopropylbiphenyl] in place of [1,1'-bis (diphenylphosphino)ferrocene]dichloropalladium(II), complex with dichloromethane. The obtained Intermediate 7

(76% yield, white solid) was characterized by by ESI-MS (electrospray ionisation mass spectrometry). The results are shown below.

ESI-MS: calcd. for C33H30BN302=511, mass found=512 (M+1)

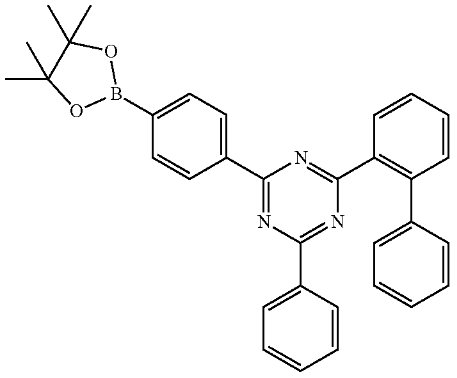

Intermediate 7

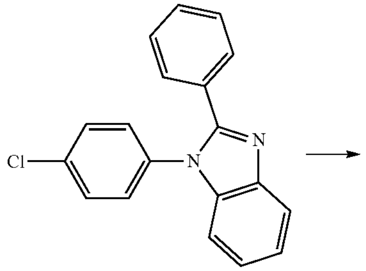

Intermediate 4

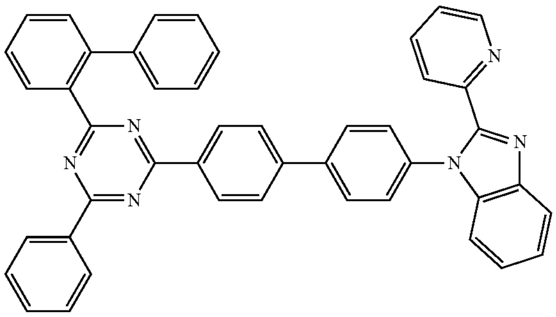

Compound 3

The procedure of the synthesis of Compound 1 was repeated except for Intermediate 7 in place of Intermediate 3. The obtained Compound 3 (91% yield, white solid) was characterized by ESI-MS, maximum ultraviolet absorption wavelength (UV(PhMe) λ onset) in toluene, and maximum fluorescence wavelength (FL(PhMe, λ ex=330 nm) λ max) in toluene. The results are shown below.

ESI-MS: calcd. for C45H30N6=655, mass found=655 (M+)

UV(PhMe) λ onset: 355 nm

FL(PhMe, λ ex=330 nm) λ max: 381 nm

Compound 4

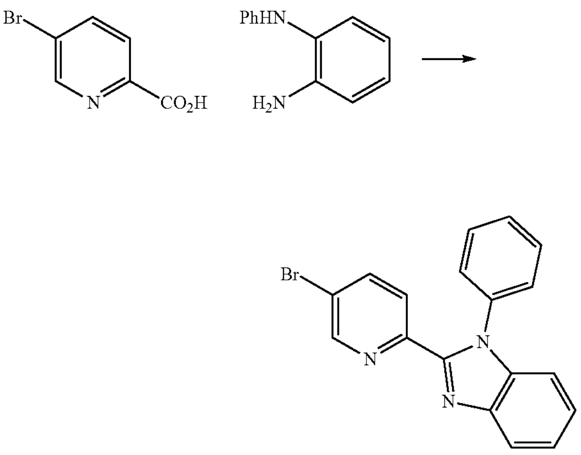

Intermediate

N-phenylbenzene-1,2-diamine (25 g, 136 mmol) was combined with 5-bromopicolinic acid (33 g, 163 mmol) in dichloromethane (500 mL) and the solution was cooled in an ice bath. 3-(((ethylimino)methylene)amino)-N,N-dimethyl-propan-1-amine hydrochloride (31.2 g, 163 mmol) was added portionwise maintaining the reaction temperature at 1-2° C. N-ethyl-N-isopropylpropan-2-amine (59 mL, 339 mmol) was then added and the reaction was allowed to warm to room temperature. After 2 hours, the reaction was worked up by washing the reaction solution with water. It was then dried over anhydrous magnesium sulphate and the solvent was evaporated. Methanol was added and the mixture was stirred at room temperature and the precipitate was then collected by filtration and dried in air. The precipitate was then added to Eaton's reagent (10 wt % phosphorus pentoxide solution in methanesulfonic acid, 420 mL) and the reaction mixture was heated at 70° C. for 16 hours. The reaction mixture was allowed to cool to room temperature and poured onto water (1.5 mL). The solution was neutralised by the addition of sodium hydroxide pellets. The precipitate that was formed was collected by filtration and allowed to dry in air. The crude product was then stirred in heptane for 1 hour at room temperature and the precipitate was collected by filtration and used without further purification. Intermediate 8 (36 g, 76% yield) was characterised by ESI-MS. The results are below.

ESI-MS: calcd. for C18H12BrN3=350, mass found=350 (M+)

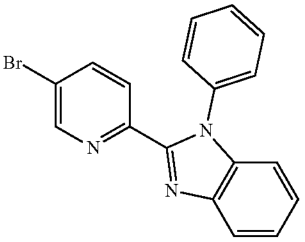

Intermediate 8

-continued

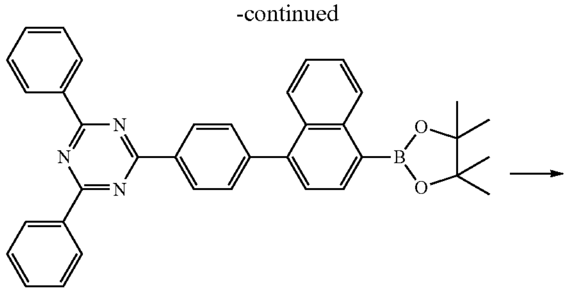

Intermediate 3

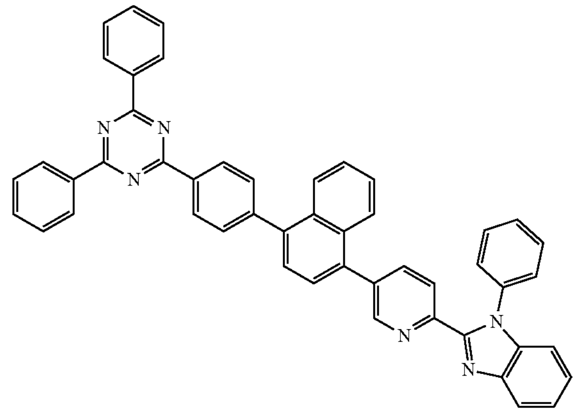

Compound 4

The procedure of the synthesis of Compound 1 was repeated except for Intermediate 8 in place of Intermediate 4. The obtained Compound 4 (70% yield, white solid) was characterized by ESI-MS, maximum ultraviolet absorption wavelength (UV(PhMe) λ onset) in toluene, and maximum fluorescence wavelength (FL(PhMe, λ ex=330 nm) λ max) in toluene. The results are shown below.

ESI-MS: calcd. for C49H32N6=705, mass found=705 (M+)

UV(PhMe) λ onset: 383 nm

FL(PhMe, λ ex=330 nm) λ max: 426 nm

Compound 5

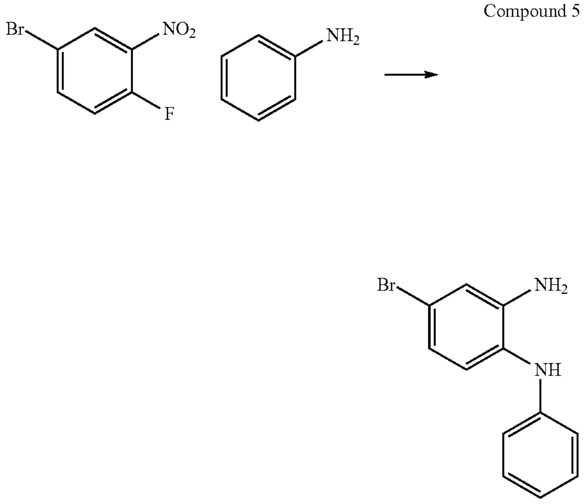

Intermediate 9

4-bromo-1-fluoro-2-nitrobenzene (13.3 mL, 107 mmol) was combined with aniline (10 mL, 107 mmol) in dioxane/water (200 mL, 1:1) and potassium carbonate (17.8 g, 129 mmol) was added. The resulting reaction mixture was heated under reflux for 16 hours. The reaction mixture was then cooled to room temperature and the reaction mixture was concentrated under reduced pressure. The crude material was dissolved in ethyl acetate and washed with water, dried over magnesium sulphate and the solvent was removed under reduced pressure. The crude product thus obtained was dissolved in THF/water (200 mL, 1:1) and zinc powder (31.7 g, 485 mmol) was added portionwise followed by ammonium chloride (52 g, 970 mmol) portionwise. The reaction mixture was allowed to stir at room temperature over night. The reaction mixture was then filtered and the mother liquor was diluted with ethyl acetate. The water was separated and the organic phase was then washed with saturated sodium bicarbonte and then brine, dried over anhydrous magnesium sulphate and the solvent was evaporated. Intermediate 9 (23.6 g, 80% yield) was obtained and used without further purification. Intermediate 9 was characterised by ESI-MS. The results are below.

ESI-MS: calcd. for C18H12BrN3=350, mass found=350 (M+)

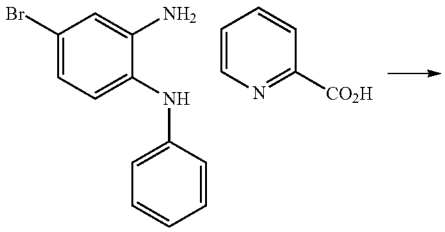

Intermediate 9

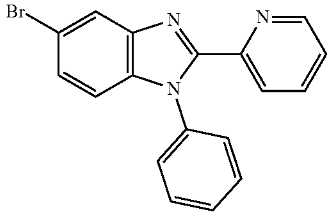

Intermediate 10

The procedure of the synthesis of Intermediate 8 was repeated except for using intermediate 9 in place of N-phenylbenzene-1,2-diamine and picolinic acid in place of 5-bromopicolinic acid.

The obtained Intermediate 10 (69% yield, brown gum) was characterized by by ESI-MS (electrospray ionisation mass spectrometry). The results are shown below.

ESI-MS: calcd. for C18H12BrN3=350, mass found=350 (M+)

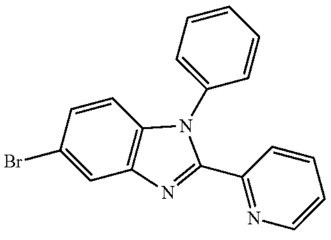

Intermediate 10

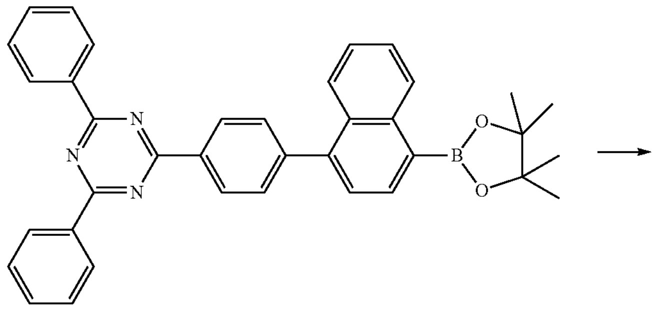

Intermediate 3

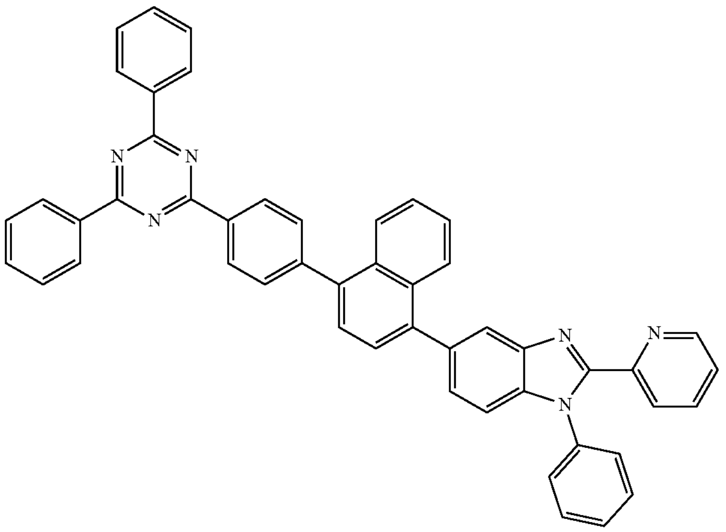

Compound 5

The procedure of the synthesis of Compound 1 was repeated except for Intermediate 10 in place of Intermediate 4. The obtained Compound 5 (49% yield, white solid) was characterized by ESI-MS, maximum ultraviolet absorption wavelength (UV(PhMe) λ onset) in toluene, and maximum fluorescence wavelength (EL(PhMe, λ ex=330 nm) λ max) in toluene. The results are shown below.

ESI-MS: calcd. for C49H32N6=705, mass found=705 (M+)

UV(PhMe) λ onset: 395 nm

FL(PhMe, λ ex=330 nm) λ max: 432 nm

Comparative Compound 1

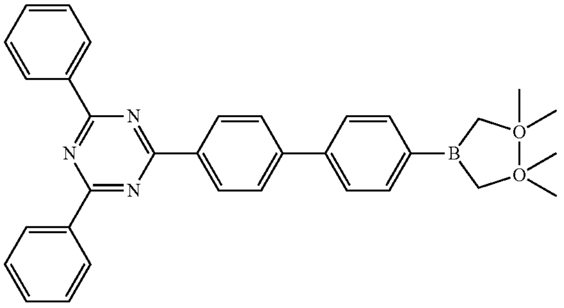

Intermediate 6

-continued

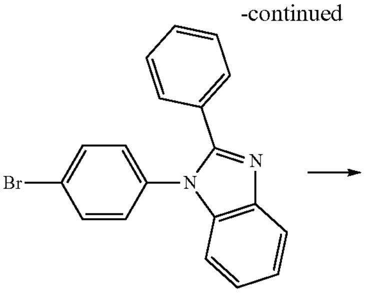

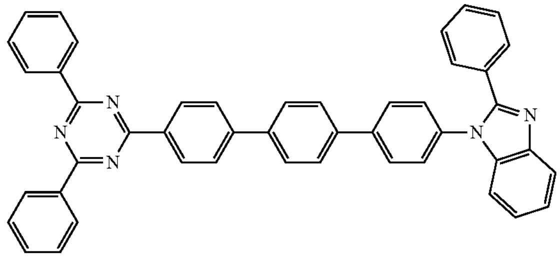

Comparative compound 1

The procedure of the synthesis of Compound 1 was repeated except for Intermediate 6 in place of Intermediate 3 and 1-(4-bromophenyl)-2-phenyl-1H-benzo[d]imidazole in place of Intermediate 4. The obtained Comparative compound 1 (97% yield, white solid) was characterized by ESI-MS, maximum ultraviolet absorption wavelength (UV (PhMe) λ onset) in toluene, and maximum fluorescence wavelength (FL(PhMe, λ ex=330 nm) λ max) in toluene. The results are shown below.

ESI-MS: calcd. for C46H31N5=654, mass found=654 (M+)

UV(PhMe) λ onset: 368 nm

FL(PhMe, λ ex=330 nm) λ max: 403 nm

II Application Examples

Application Example 1

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 5 nm-thick Compound HB was applied as an hole-blocking layer and 25 nm of Compound 1 as electron transporting layer. Finally, 1 nm-thick Yb was deposited as an electron injection layer and 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 mA/$cm^2$. The device results are shown in Table 1.

Compound HI

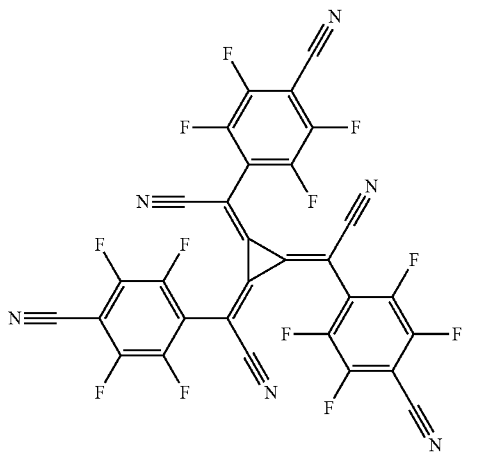

-continued

Compound HT

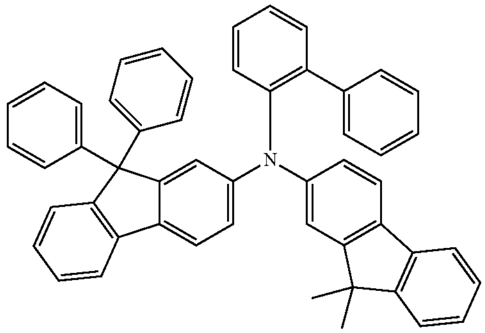

Compound EB

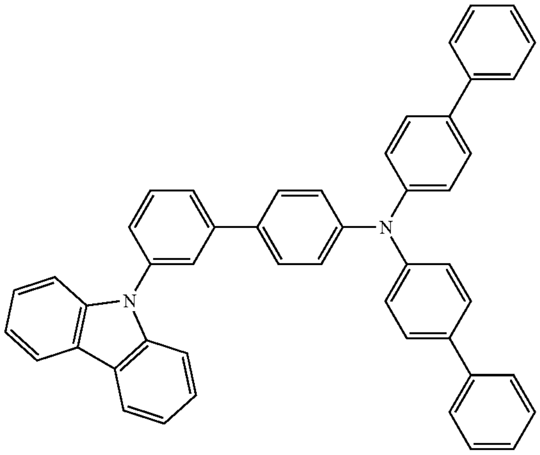

Compound BD-1

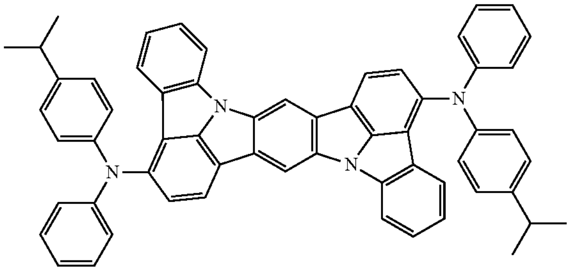

Compound BH-1

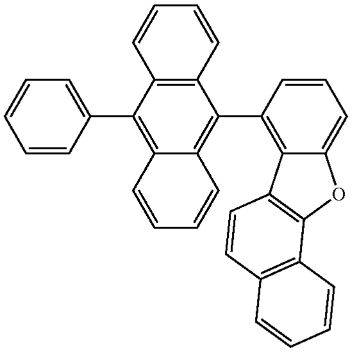

-continued

Compound HB

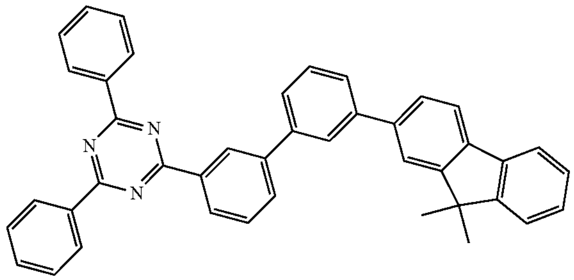

Compound 1

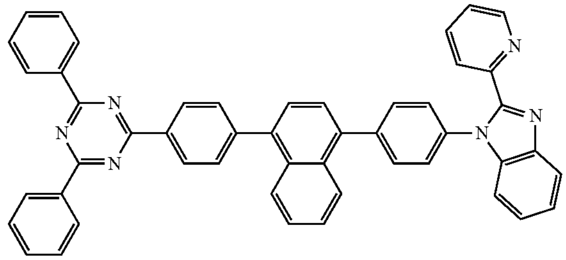

Compound 2

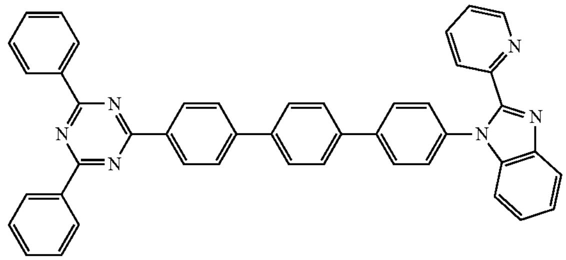

Compound 3

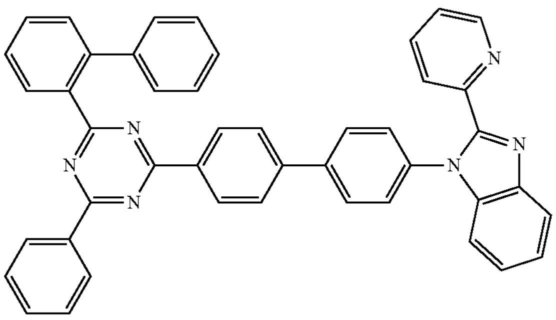

Comparative Compound 1

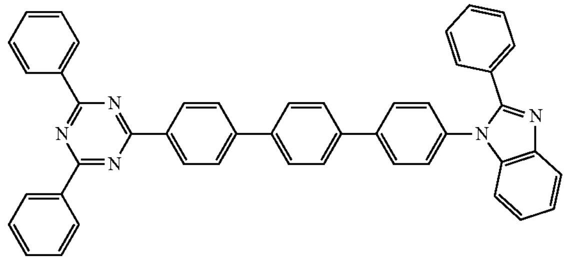

Application Example 2

Application Example 1 was repeated except for using the Compound 2 in place of Compound 1 in the electron transporting layer.

Application Example 3

Application Example 1 was repeated except for using the Compound 3 in place of Compound 1 in the electron transporting layer.

Comparative Application Example 1

Application Example 1 was repeated except for using the Comparative Compound 1 in place of Compound 1 in the electron transporting layer.

TABLE 1

| Appl. Ex. | ET | Voltage, (V) | EQE (%) |
|---|---|---|---|
| Appl. Ex. 1 | Compound 1 | 3.3 | 9.5 |
| Appl. Ex. 2 | Compound 2 | 3.4 | 9.0 |
| Appl. Ex. 3 | Compound 3 | 3.3 | 9.4 |
| Comp. Appl. Ex. 1 | Comparative compound 1 | 3.8 | 8.1 |

These results demonstrate that the voltage, efficiency and lifetime are improved in the case that the inventive Compounds are used instead of the Comparative Compounds as the electron transporting material without Liq-doping in an OLED device with Yb as electron injecting layer.

Application Example 4

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 5 nm-thick Compound HB was applied as an hole-blocking layer and and 25 nm of Compound 1 as electron transporting layer. Finally, 1 nm-thick LiF was deposited as an electron injection layer and 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 $mA/cm^2$. The device results are shown in Table 2.

Application Example 5

Application Example 4 was repeated except for using the Compound 2 in place of Compound 1 in the electron transporting layer.

Application Example 6

Application Example 4 was repeated except for using the Compound 3 in place of Compound 1 in the electron transporting layer.

Comparative Application Example 2

Application Example 4 was repeated except for using the Comparative Compound 1 in place of Compound 1 in the electron transporting layer.

TABLE 2

| Appl. Ex. | ET | Voltage, (V) | EQE (%) |
|---|---|---|---|
| Appl. Ex. 4 | Compound 1 | 3.3 | 9.6 |
| Appl. Ex. 5 | Compound 2 | 3.4 | 9.1 |
| Appl. Ex. 6 | Compound 3 | 3.3 | 9.5 |
| Comp. Appl. Ex. 2 | Comparative compound 1 | 3.6 | 8.3 |

Application Example 7

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 5 nm-thick Compound HB was applied as an hole-blocking layer and 20 nm of mixture of 50% by weight of Compound 1 and lithiumquinolate (Liq) as electron-transporting layer. Finally, 1 nm-thick Yb was deposited as an electron injection layer and 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 mA/cm$^2$. The device results are shown in Table 3.

Application Example 8

Application Example 8 was repeated except for using the Compound 3 in place of Compound 1 in the electron transporting layer.

Comparative Application Example 3

Application Example 7 was repeated except for using the Comparative Compound 1 in place of Compound 1 in the electron transporting layer.

TABLE 3

| Appl. Ex. | ET | Voltage, (V) | EQE (%) |
|---|---|---|---|
| Appl. Ex. 7 | Compound 1 | 3.3 | 9.7 |
| Appl. Ex. 8 | Compound 3 | 3.3 | 9.3 |
| Comp. Appl. Ex. 3 | Comparative compound 1 | 3.4 | 9.0 |

What is claimed is:

1. A compound of formula (I):

(I)

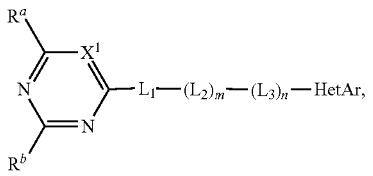

wherein

—$L_1$-$(L_2)_m$- is:

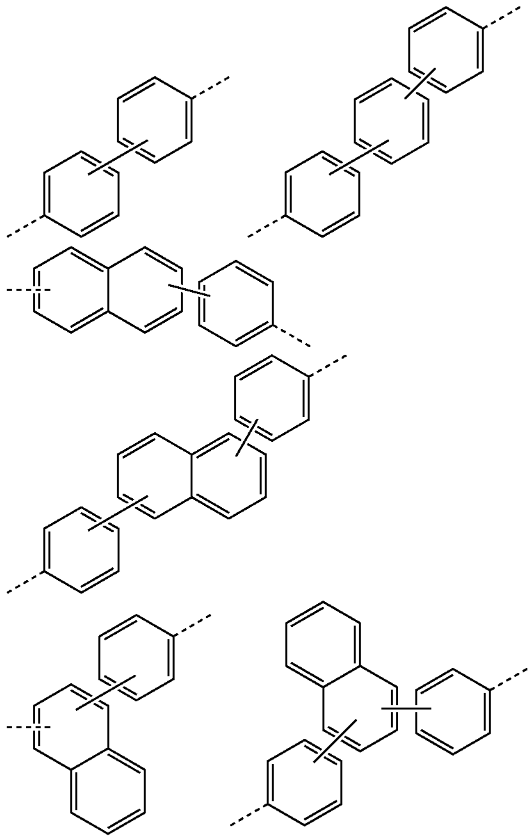

-continued

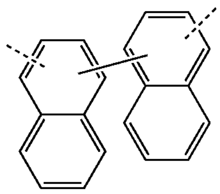

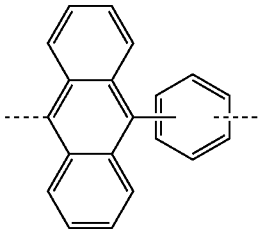

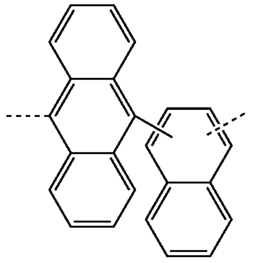

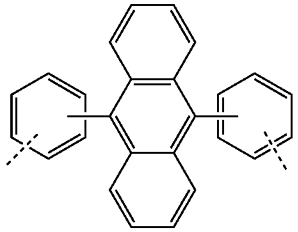

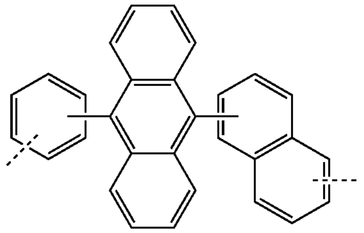

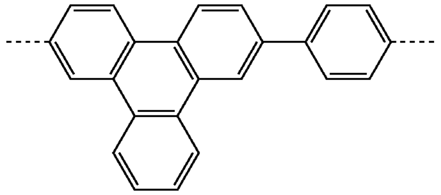

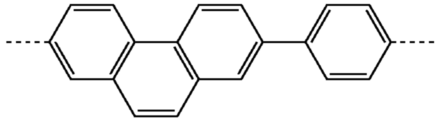

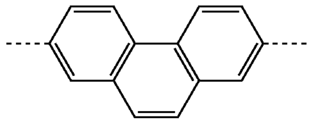

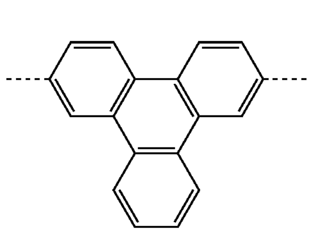

$L_3$ is a group of a formula

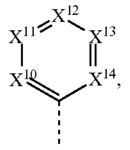

wherein $X^{10}$ is N or $CR^{10}$, $X^{11}$ is N or $CR^{11}$, $X^{12}$ is N or $CR^{12}$, $X^{13}$ is N or $CR^{13}$, $X^{14}$ is N or $CR^{14}$;

wherein at least one of $X^{10}$, $X^{11}$, $X^{12}$, $X^{13}$ and $X^{14}$ is N; and one of $X^{10}$, $X^{11}$, $X^{12}$, $X^{13}$ and $X^{14}$;

C----, $R^a$ and $R^b$ are each independently an unsubstituted aromatic hydrocarbon group comprising 6 to 30 ring atoms, n is 0 or 1, $X^1$ is N, HetAr has formula (II) or (III):

(II)

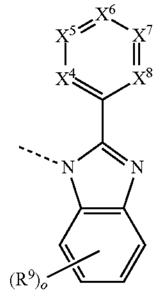

(III)

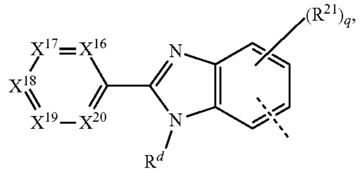

or, if n is 1, HetAr has formula (II), (III), or (IV):

(IV)

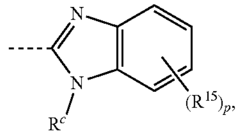

$X^4$ is N or $CR^4$, $X^5$ is N or $CR^5$, $X^6$ is N or $CR^6$, $X^7$ is N or $CR^7$, $X^8$ is N or $CR^8$, wherein at least one of $X^4$, $X^5$, $X^6$, $X^7$, and $X^8$ is N, $X^{16}$ is N or $CR^{16}$, $X^{17}$ is N or $CR^{17}$, $X^{18}$ is N or $CR^{18}$, $X^{19}$ is N or $CR^{19}$, $X^{20}$ is N or $CR^{20}$, wherein at least one of $X^{16}$, $X^{17}$, $X^{18}$, $X^{19}$, and $X^{20}$ is N, o and p are each independently 0, 1, 2, 3, or 4, q is 0, 1, 2, or 3 and $R^1$, $R^4$, $R^3$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently hydrogen, an unsubstituted or substituted aromatic hydrocarbon group comprising 6 to 30 ring atoms or an unsubstituted or substituted heteroaromatic group comprising 3 to 30 ring atoms, an unsubstituted or substituted alkyl group comprising 1 to 25 carbon atoms, an unsubstituted or substituted cycloalkyl group comprising 3 to 18 ring carbon atoms or CN, or two adjacent groups $R^9$, two adjacent groups $R^{15}$, or two adjacent groups $R^{21}$ and/or two adjacent groups selected from $R^4$, $R^5$, $R^6$, $R^7$, $R^8$, $R^{16}$, $R^{17}$, $R^{18}$, $R^{19}$, and $R^{20}$ form together a substituted or unsubstituted carbocyclic or heterocyclic ring, ring;

$R^c$ and $R^d$ are each independently an unsubstituted or substituted aromatic hydrocarbon group comprising 6 to 30 ring atoms or an unsubstituted or substituted heteroaromatic group comprising 3 to 30 ring atoms, an unsubstituted or substituted alkyl group comprising 1 to 25 carbon atoms, an unsubstituted or substituted cycloalkyl group comprising 3 to 18 ring carbon atoms, and a dotted line is a bonding site.

2. The compound according to of claim 1, wherein $-(L_3)_n$-HetAr has formula (IIa), (IIb), (IIc), (IIIa), (IIIb), (IIIc), (IVa), (IVb), or (IVc):

(IIa)

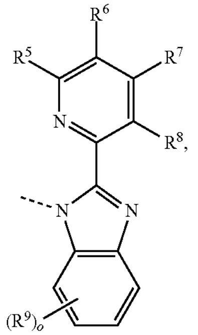

(IIb)

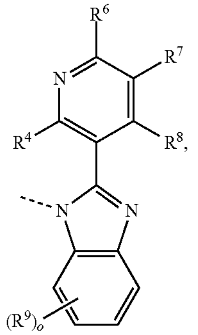

-continued (IIc)

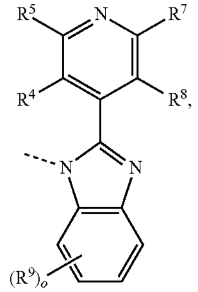

(IIIa)

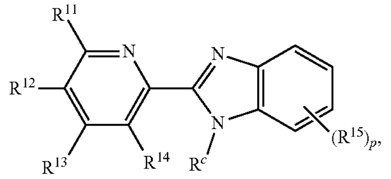

(IIIb)

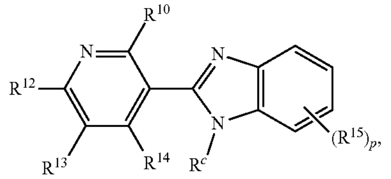

(IIIc)

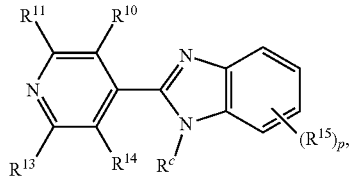

(IVa)

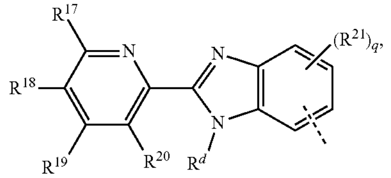

(IVb)

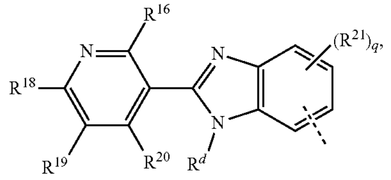

(IVc)

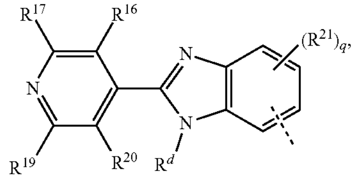

wherein one of one of $R^1$, $R^{12}$, $R^{13}$ and $R^{14}$ in formula (IIIa), one of one of $R^{10}$, $R^{12}$, $R^{13}$, and $R^{14}$ in formula (IIIb) and one of one of $R^{10}$, $R^1$, $R^{13}$, and $R^{14}$ in formula (IIIc) is a bonding site.

3. The compound of claim 1, wherein o, p, and q are 0.

4. The compound of claim 1, wherein $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are hydrogen.

5. The compound of claim 1, wherein $R^a$ and $R^b$ are each independently an unsubstituted aromatic hydrocarbon group comprising 6 to 18 ring atoms.

6. The compound of claim 1, wherein $R^c$ and $R^d$ are each independently an unsubstituted or substituted aromatic hydrocarbon group comprising 6 to 18 ring atoms.

7. The compound of claim 1, wherein n is 0.

8. A material for an organic electroluminescence device, comprising:

the compound of claim 1.

9. An organic electroluminescence device, comprising:

a cathode;

an anode; and an organic thin film layer comprising an emitting layer disposed between the cathode and the anode, wherein at least one layer of the organic thin film layer comprises the compound of claim 1.

10. The device of claim 9, wherein the organic thin film layer further comprises an electron-transporting zone provided between the emitting layer and the cathode.

11. The device of claim 10, wherein the electron-transporting zone comprises an electron-transporting layer provided between the emitting layer and the cathode.

12. The device of claim 10, wherein the electron-transporting zone further comprises a metal, a metal complex, and/or a metal compound.

13. Electronic An electronic equipment, comprising:

the organic electroluminescence device of claim 9.

14. Use of a-A method of making an organic electroluminescence device, the method comprising:

combining the compound of claim 1 and the organic electroluminescence device.

15. The compound of claim 1, wherein $-L_1-(L_2)_m-$ is:

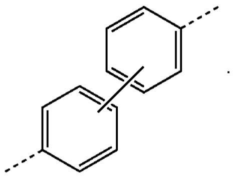

16. The compound of claim 1, wherein $-L_1-(L_2)_m-$ is:

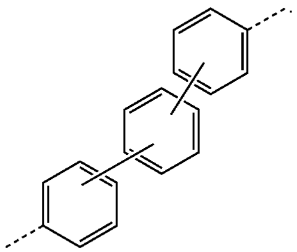

17. The compound of claim 1, wherein $-L_1-(L_2)_m-$ is:

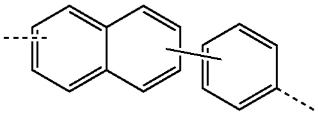

or

-continued

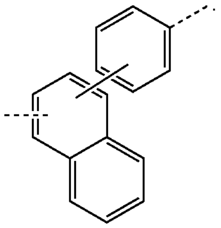

18. The compound of claim 1, wherein $-L_1-(L_2)_m-$ is:

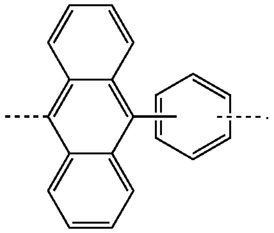

19. The compound of claim 1, wherein $-L_1-(L_2)_m-$ is:

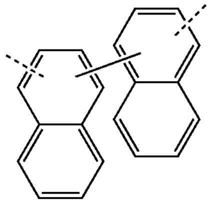

or

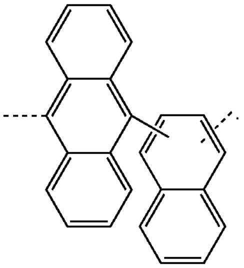

20. The compound of claim 1, wherein $-L_1-(L_2)_m-$ is:

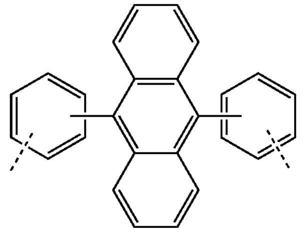

or

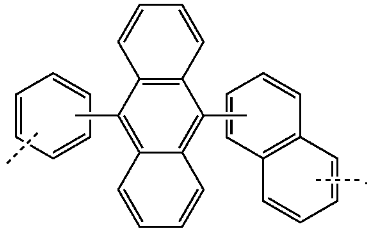

* * * * *